(12) United States Patent
Furuya et al.

(10) Patent No.: US 8,686,158 B2
(45) Date of Patent: Apr. 1, 2014

(54) HIGH-VALENT PALLADIUM FLUORIDE COMPLEXES AND USES THEREOF

(75) Inventors: Takeru Furuya, Cambridge, MA (US);
David Powers, Cambridge, MA (US);
Tobias Ritter, Cambridge, MA (US)

(73) Assignee: President and Fellows of Harvard College, Cambridge, MA (US)

(*) Notice: Subject to any disclaimer, the term of this patent is extended or adjusted under 35 U.S.C. 154(b) by 168 days.

(21) Appl. No.: 12/996,274

(22) PCT Filed: Jun. 5, 2009

(86) PCT No.: PCT/US2009/046401
§ 371 (c)(1),
(2), (4) Date: May 10, 2011

(87) PCT Pub. No.: WO2009/149347
PCT Pub. Date: Dec. 10, 2009

(65) Prior Publication Data
US 2011/0212936 A1    Sep. 1, 2011

Related U.S. Application Data

(60) Provisional application No. 61/059,142, filed on Jun. 5, 2008.

(51) Int. Cl.
*C07F 15/00* (2006.01)

(52) U.S. Cl.
CPC .................................. *C07F 15/006* (2013.01)
USPC .......................................................... 548/101

(58) Field of Classification Search
CPC .................................................... C07F 15/006
USPC .......................................................... 548/101
See application file for complete search history.

(56) References Cited

U.S. PATENT DOCUMENTS

| | | | |
|---|---|---|---|
| 3,137,701 A | 6/1964 | Ayer | |
| 3,641,153 A | 2/1972 | Kyburz et al. | |
| 3,972,936 A | 8/1976 | Christy | |
| 3,991,103 A | 11/1976 | Barton et al. | |
| 4,236,008 A | 11/1980 | Henderson | |
| 4,402,956 A | 9/1983 | Silvestrini et al. | |
| 4,487,773 A | 12/1984 | Temple, Jr. et al. | |
| 6,069,110 A | 5/2000 | Klaui et al. | |
| 6,127,583 A | 10/2000 | Sonoda et al. | |
| 7,108,846 B1 | 9/2006 | Marchand et al. | |
| 7,115,249 B2 | 10/2006 | Luthra et al. | |
| 2005/0085474 A1 | 4/2005 | Ebenbeck et al. | |
| 2005/0137421 A1 | 6/2005 | Walsh et al. | |
| 2006/0083677 A1 | 4/2006 | Brady et al. | |
| 2007/0092441 A1 | 4/2007 | Wadsworth et al. | |
| 2009/0247517 A1 | 10/2009 | Liu et al. | |
| 2011/0054175 A1 | 3/2011 | Ritter et al. | |
| 2011/0312903 A1 | 12/2011 | Ritter et al. | |
| 2012/0095217 A1 | 4/2012 | Ritter et al. | |
| 2012/0149900 A1 | 6/2012 | Ritter et al. | |
| 2012/0316120 A1 | 12/2012 | Ritter | |
| 2012/0316341 A1 | 12/2012 | Ritter et al. | |

FOREIGN PATENT DOCUMENTS

| | | |
|---|---|---|
| DE | 23 60 940 A1 | 4/1975 |
| EP | 0 915 094 A1 | 5/1999 |
| GB | 1 177 525 A | 1/1970 |
| JP | 63-166159 A | 7/1988 |
| WO | WO 2005/063254 A2 | 7/2005 |
| WO | WO 2005/117872 A2 | 12/2005 |
| WO | WO 2008/081477 A1 | 7/2008 |
| WO | WO 2009/033751 A2 | 3/2009 |
| WO | WO 2009/100014 A1 | 8/2009 |
| WO | WO 2009/141053 A1 | 11/2009 |
| WO | WO 2009/149347 A1 | 12/2009 |
| WO | WO 2010/059943 A2 | 5/2010 |
| WO | WO 2010/081034 A2 | 7/2010 |
| WO | WO 2010/081036 A2 | 7/2010 |
| WO | WO 2011/006088 A2 | 1/2011 |
| WO | WO 2012/024604 A2 | 2/2012 |
| WO | WO 2012/054782 A2 | 4/2012 |
| WO | WO 2012/142162 A2 | 10/2012 |

OTHER PUBLICATIONS

Espinet et al. "(CN)-chelate, N,N'-bridged dimeric palladium complexes derived from hydrazones PhC(R):NN'HPh. X-ray structure of [Pd(o-C6H4C(R):NNPh)L]2 [R=Me, L=P(OMe)3]" Inorganic Chemistry, 1989, vol. 28, pp. 4207-4211.*
Extended European Search Report for EP 09759505.2, mailed Jan. 20, 2012.
International Search Report and Written Opinion for PCT/US2009/046401, mailed Sep. 22, 2009.
International Preliminary Report on Patentability for PCT/US2009/046401, mailed Dec. 16, 2010.
International Search Report and Written Opinion for PCT/US2009/032855, mailed Jun. 8, 2009.
International Preliminary Report on Patentability for PCT/US2009/032855, mailed Aug. 12, 2010.
Invitation to Pay Additional Fees for PCT/US2010/041561, mailed Sep. 28, 2010.
International Search Report and Written Opinion for PCT/US2010/041561, mailed Jun. 15, 2011.
International Preliminary Report on Patentability for PCT/US2010/041561, mailed Jan. 19, 2012.
Extended European Search Report for EP 10729595.8, mailed May 22, 2013.
International Search Report and Written Opinion for PCT/US2010/020544, mailed Oct. 7, 2010.
International Preliminary Report on Patentability for PCT/US2010/020544, mailed Jul. 21, 2011.

(Continued)

*Primary Examiner* — Joseph Kosack
(74) *Attorney, Agent, or Firm* — Wolf, Greenfield & Sacks, P.C.; C. Hunter Baker

(57) ABSTRACT

The present invention provides novel high-valent palladium fluoride complexes. The complexes typically include multidentate ligands that stabilize the octahedral coordination sphere of the palladium(IV) atom. These complexes are useful in fluorinating organic compounds, in particular aryl-containing compounds. The invention is particularly useful for fluorinating compounds with $^{19}F$ for PET imaging.

29 Claims, 9 Drawing Sheets

(56) References Cited

OTHER PUBLICATIONS

Extended European Search Report for EP 09828291.6, mailed May 18, 2012.
International Search Report and Written Opinion for PCT/US2009/065339, mailed Jul. 12, 2010.
International Preliminary Report on Patentability for PCT/US2009/065339, mailed Jun. 3, 2011.
International Search Report and Written Opinion for PCT/US2011/048451, mailed Mar. 22, 2012.
International Preliminary Report on Patentability for PCT/US2011/048451, mailed Mar. 7, 2013.
International Search Report and Written Opinion for PCT/US2012/033125, mailed Nov. 9, 2012.
International Preliminary Report on Patentability for PCT/US2012/033125, mailed Oct. 24, 2013.
Extended European Search Report for EP 10729593.3, mailed May 3, 2012.
International Search Report and Written Opinion for PCT/US2010/020540, mailed Oct. 6, 2010.
International Preliminary Report on Patentability for PCT/US2010/020540, mailed Jul. 21, 2011.
International Search Report and Written Opinion for PCT/US2011/057176, mailed May 3, 2012.
International Preliminary Report on Patentability for PCT/US2011/057176, mailed May 2, 2013.
Office Communication, mailed Sep. 18, 2012, for U.S. Appl. No. 12/865,703.
Office Communication, mailed Jan. 28, 2013, for U.S. Appl. No. 12/865,703.
Office Communication, mailed Jul. 24, 2013, for U.S. Appl. No. 13/130,033.
[No Author Listed] PubChem Compound Summary titled "Dadle" (Jul. 28, 2006) [Retrieved from the Internet Sep. 14, 2010: <http://pubchem.ncbi.nim.nih.gov/summary/summary.cgi?cid=6917707&loc=ec_rcs]. 4 pages.
[No Author Listed] PubChem Compound Summary titled "Enkephalin, Leucine" (Mar. 25, 2005) [Retrieved from the Internet Sep. 14, 2010: <http://pubchem.ncbi.nim.nih.gov/summary/summary.cgi?cid=3903&loc=ec_rcs Sep. 14, 2010>]. 5 pages.
Adams et al., Nucleophilic routes to selectively fluorinated aromatics. Chem Soc Rev. 1999;28:225-31.
Ahmed et al., Boronic acids as inhibitors of steroid sulfatase. Bioorg Med Chem. Dec. 15, 2006;14(24):8564-73. Epub Sep. 14, 2006.
Alvarez-Corral et al., Silver-mediated synthesis of heterocycles. Chem Rev. Aug. 2008;108(8):3174-98. doi: 10.1021/cr0783611. Epub Jul. 17, 2008.
Andrae et al., Energy-adjustedab initio pseudopotentials for the second and third row transition elements. Theor Chem Acta. 1990;77(2):123-41.
Andrae et al., Energy-adjustedab initio pseudopotentials for the second and third row transition elements: Molecular test for M2 (M=Ag, Au) and MH (M=Ru, Os). Theor Chim Acta. 1991;78(4):247-66.
Avdeef et al., Octanol-, chloroform-, and propylene glycol dipelargonat-water partitioning of morphine-6-glucuronide and other related opiates. J Med Chem. Oct. 25, 1996;39(22):4377-81.
Balz et al., Ober aromatische Fluorverbindungen, I.: Ein neues Verfahren zu ihrer Darstellung. Ber Deut Chem Ges. 1927;60:1186-90.
Becke, Density-functional thermochemistry. III. The role of exact exchange. J Chem Phys. 1993;98(7): 5648-52.
Berge et al., Pharmaceutical Salts. J. Pharmaceutical Sciences 1977;66:1-19.
Bergman et al., Fluorine-18-labeled fluorine gas for synthesis of tracer molecules. Nucl Med Biol. Oct. 1997;24(7):677-83.
Berry et al., An octahedral coordination complex of iron(VI). Science. Jun. 30, 2006;312(5782):1937-41. Epub Jun. 1, 2006.
Billingsley et al., Palladium-catalyzed borylation of aryl chlorides: scope, applications, and computational studies. Angew Chem. 2007;119(28):5455-59.

Black et al., Observations on the mechanism of halogen-bridge cleavage by unidentate ligands in square planar palladium and platinum complexes. Australian Journal of Chemistry. 1994;47(2):217-227.
Bohm et al., Fluorine in medicinal chemistry. Chembiochem. May 3, 2004;5(5):637-43.
Brown et al., Transition-metal-mediated reactions for C(sp2)-F bond construction: the state of play. Angew Chem Int Ed Engl. 2009;48(46):8610-4. doi: 10.1002/anie.200902121.
Buzzi et al., The antimigraine drug, sumatriptan (GR43175), selectively blocks neurogenic plasma extravasation from blood vessels in dura mater. Br J Pharmacol. Jan. 1990;99(1):202-6.
Campbell et al., Synthesis and structure of solution-stable one-dimensional palladium wires. Nat Chem. Nov. 13, 2011;3(12):949-53. doi: 10.1038/nchem.1197.
Cámpora et al., Redox Behavior of an Organometallic Palladium(II)/Palladium(IV) System. A New Method for the Synthesis of Cationic Palladium(IV) Complexes. Organometallics. 2005;24(15):3624-3628.
Canty et al., Carbon—Oxygen Bond Formation at Metal(IV) Centers: Reactivity of Palladium(IIi) and Platinum(II) Complexes of the [2,6-(Dimethylaminomethyl)phenyl-N,C,N]- (Pincer) Ligand toward Iodomethane and Dibenzoyl Peroxide; Structural Studies of M(II) and M(IV) Complexes. Organometallics. 2004;23(23):5432-5439.
Canty et al., Synthesis and Characterization of Ambient Temperature Stable Organopalladium(IV) Complexes, Including Aryl-, .eta.1-Allyl-, Ethylpalladium(IV), and Pallada(IV)cyclopentane Complexes. Structures of the Poly(pyrazol-1-yl)borate Complexes PdMe3{(pz)3BH} and PdMe3{(pz)4B } and Three Polymorphs of PdMe2Et{(pz)3BH}. Organometallics. 1995;14(1):199-206.
Canty et al., Synthesis of halogeno, pseudohalogeno, and carboxylatopalladium(IV) complexes by halogen exchange. Crystal structure of azido(2,2'-bipyridyl)- benzylpalladium(II), formed on reductive elimination of ethane from Pd(N3)Me2(CH2Ph)(bpy). J Organometallic Chem. 1992;433(1-2):213-22.
Chan et al., Palladium(II)—catalyzed selective monofluorination of benzoic acids using a practical auxiliary: a weak-coordination approach. Angew Chem Int Ed Engl. Sep. 19, 2011;50(39):9081-4. doi: 10.1002/anie.201102985. Epub Jul. 11, 2011.
Chuang et al., A dinuclear palladium catalyst for a-hydroxylation of carbonyls with O2. J Am Chem Soc. Feb. 16, 2011;133(6):1760-2. doi: 10.1021/ja108396k. Epub Jan. 19, 2011.
Chung et al., Segmental spinal nerve ligation model of neuropathic pain. Methods Mol Med. 2004;99:35-45.
Constaninou et al., Xenon difluoride exchanges fluoride under mild conditions: a simple preparation of [(18)F]xenon difluoride for PET and mechanistic studies. J Am Chem Soc. Feb. 28, 2001;123(8):1780-1.
Cope et al., Electrophilic aromatttic substitution reactions by platinum(II) and palladium(II) chlorides on N,N-dimethylbenzylamines J Am Chem Soc. 1968;90(4):909-913.
Couturier et al., Fluorinated tracers for imaging cancer with positron emission tomography. Eur J Nucl Med Mol Imaging. Aug. 2004;31(8):1182-206. Epub Jul. 6, 2004.
Czarnik, Encoding methods for combinatorial chemistry. Curr Opin Chem Biol. Jun. 1997;1(1):60-6.
Danielson et al., Use of 19F NMR to probe protein structure and conformational changes. Annu Rev Biophys Biomol Struct. 1996;25:163-95.
Dick et al., A highly selective catalytic method for the oxidative functionalization of C-H bonds. J Am Chem Soc. Mar. 3, 2004;126(8):2300-1.
Dick et al., Carbon—Nitrogen Bond-Forming Reactions of Palladacycles with Hypervalent Iodine Reagents. Organometallics. 2007;26(6):1365-1370.
Dick et al., Unusually stable palladium(IV) complexes: detailed mechanistic investigation of C-O bond-forming reductive elimination. J Am Chem Soc. Sep. 21, 2005;127(37):12790-1.
Edwards et al., In vitro and in vivo studies of neutral cyclometallated complexes against murine leukemias. Canadian Journal of Chemistry. 2005;83(6-7):980-989.

(56) References Cited

OTHER PUBLICATIONS

Ehlers et al., A set of f-polarization functions for pseudo-potential basis sets of the transition metals Sc Cu, Y Ag and La Au. Chem Phys Lett. 1993;208(1-2):111-14.

Ernst et al., Presynaptic dopaminergic deficits in Lesch-Nyhan disease. n. Engl J Med. Jun. 13, 1996;334(24):1568-72.

Espinet et al., (CN)-chelate, N,N'-bridged dimeric palladium complexes derived from hydrazones PhC(R):Nn'HPh. X-ray structure of [Pd(o-C6H4C(R):NNPh)L]2 [R=Me, L 32 P(OMe)3]. Inorg Chem., 1989;28(23):4207-4211.

Evans, The determination of the paramagnetic susceptibility of substances in solution by nuclear magnetic resonance. J Chem Soc. 1959;2003-2005.

Fier et al., Copper-mediated fluorination of aryl iodides. J Am Chem Soc. Jul. 4, 2012;134(26):10795-8. doi: 10.1021/ja304410x. Epub Jun. 22, 2012.

Fier et al., Copper-mediated fluorination of arylboronate esters. Identification of a copper(III) fluoride complex. J Am Chem Soc. Feb. 20, 2013;135(7):2552-9. doi: 10.1021/ja310909q. Epub Feb. 5, 2013.

Folgado et al., Fluxionality in hexacoordinated copper(II) complexes with 2,2':6',2"-terpyridine (terpy) and related ligands: structural and spectroscopic investigations. Inorg Chem. 1990;29(11):2035-2042.

Ford et al., Regioselectivity in metallation reactions of 2-(2'-naphthyl)pyridine: 1'-versus 3'-reactivity in mercuration and palladation reactions. Crystal structure of chloro(pyridine) [2-(2—pyridiny)naphthyl-C3,N]palladium. J Organometallic Chem. 1995;493(1-2):215-20.

Fraser et al., Molecular Fluoro Palladium Complexes. J Am Chem Soc. 1997;119(20):4769-70.

Fulmer et al., NMR Chemical Shifts of Trace Impurities: Common Laboratory Solvents, Organics, and Gases in Deuterated Solvents Relevant to the Organometallic Chemist. Organometallics. 2010;29(9):2176-2179.

Furuya et al., Carbon-Fluorine Bond Formation for the Synthesis of Aryl Fluorides. Synthesis. 2010;11:1804-1821.

Furuya et al., Carbon-fluorine bond formation. Curr Opin Drug Discov Devel. Nov. 2008;11(6):803-19.

Furuya et al., Carbon-fluorine reductive elimination from a high-valent palladium fluoride. J Am Chem Soc. Aug. 6, 2008;130(31):10060-1. doi: 10.1021/ja803187x. Epub Jul. 11, 2008.

Furuya et al., Catalysis for fluorination and trifluoromethylation. Nature. May 26, 2011;473(7348):470-7. doi: 10.1038/nature10108.

Furuya et al., Fluorination of boronic acids mediated by silver(I) triflate. Org Lett. Jul. 2, 2009;11(13):2860-3. doi: 10.1021/ol901113t.

Furuya et al., Mechanism of C-F reductive elimination from palladium(IV) fluorides. J Am Chem Soc. Mar. 24, 2010;132(11):3793-807. doi: 10.1021/ja909371t.

Furuya et al., Palladium-mediated fluorination of arylboronic acids. Angew Chem Int Ed Engl. 2008;47(32):5993-6. doi: 10.1002/anie.200802164.

Furuya et al., Silver-mediated fluorination of functionalized aryl stannanes. J Am Chem Soc. Feb. 11, 2009;131(5):1662-3. doi: 10.1021/ja8086664.

Gay et al., Lithiations of .alpha.- and .beta.-(dimethylaminomethyl)naphthalenes with nbutyllithium and condensations with benzophenone. Some related results. J Am Chem Soc. 1967;89(10):2297-2303.

Gilicinski et al., On the relative power of electrophilic fluorinating reagents of the N F class. J Fluor Chem. 1992;59(1):157-162.

Grushin et al., Ar—F Reductive Elimination from Palladium(II) Revisited. Organometallics. 2007;26(20):4997-5002.

Grushin et al., Facile Ar-CF3 bond formation at Pd. Strikingly different outcomes of reductive elimination from [(Ph3P)2Pd(CF3)Ph] and [(Xantphos)Pd(CF3)Ph]. J Am Chem Soc. Oct. 4, 2006;128(39):12644-5.

Grushin et al., Is fluoride bonded to two Pd acceptors still basic? Three CH2C12 molecules encapsulating a Pd2(mu-F)2 square and new implications for catalysis. Angew Chem Int Ed Engl. Dec. 2, 2002;41(23):4476-9.

Grushin et al., Palladium Fluoride Complexes: One More Step toward Metal-Mediated C—F Bond Formation. Chemistry—A European Journal. 2002;8(5):1006-14.

Gullick et al., Catalytic asymmetric heterogeneous aziridination of styrene using Cu2+-exchanged zeolite Y: effect of the counter-cation on enantioselectivity and on the reaction profile. New J Chem. 2004;28:1470-1478.

Hariharan et al., The influence of polarization functions on molecular orbital hydrogenation energies. Theor Chim Acta. 1973;28(3):213-22.

Hartwell et al., The formation of palladium(II)—and platinum(II)—carbon bonds by proton abstraction from benzo[h]quinoline and 8-methylquinoline. J Chem Soc D. 1970:912.

Harvey et al., A new general synthesis of polycyclic aromatic compounds based on enamine chemistry. J Org Chem. 1991;56(3):1210-1217.

Henriksen et al., Recent development and potential use of μ- and κ-opioid receptor ligands in positron emission tomography studies. Drug Dev Res. 2006;67(12):890-904.

Henriksen et al., Syntheses, biological evaluation, and molecular modeling of 18F-labeled 4-anilidopiperidines as mu-opioid receptor imaging agents. J Med Chem. Dec. 1, 2005;48(24):7720-32.

Huang et al., Silver-mediated trifluoromethoxylation of aryl stannanes and arylboronic acids. J Am Chem Soc. Aug. 31, 2011;133(34):13308-10. doi: 10.1021/ja204861a. Epub Aug. 9, 2011

Hull et al., Palladium-catalyzed fluorination of carbon-hydrogen bonds. J Am Chem Soc. Jun. 7, 2006;128(22):7134-5.

Ishiyama et al., Mild iridium-catalyzed borylation of arenes. High turnover numbers, room temperature reactions, and isolation of a potential intermediate. J Am Chem Soc. Jan. 23, 2002;124(3):390-1.

Jasim et al., Contrasting Reactivity of Fluoropyridines at Palladium and Platinum: C—F Oxidative Addition at Palladium, P—C and C—F Activation at Platinum. Organometallics 2004;23(26):6140-49.

Jeschke, The Unique Role of Fluorine in the Design of Active Ingredients for Modern Crop Protection. ChemBioChem. 2004;5(5):570-589.

Jones et al., Systemic gabapentin and S(+)-3-isobutyl-gamma-aminobutyric acid block secondary hyperalgesia. Brain Res. Nov. 9, 1998;810(1-2):93-9.

Julia et al., Orientation de la palladation du noyau naphtalenique dans les α et β dimethylaminomethyl naphtalenes. J Organometallic Chem. 1975;102(2):239-43.

Jun et al., The effect of intrathecal gabapentin and 3-isobutyl gamma-aminobutyric acid on the hyperalgesia observed after thermal injury in the rat. Anesth Analg. Feb. 1998;86(2):348-54.

Jung et al., Organic Chemistry on Solid Supports. Angew Chem Int Ed Engl. 1996;35(1):17-42.

Kamlet et al., Application of palladium-mediated (18)F-fluorination to PET radiotracer development: overcoming hurdles to translation. PLoS One. 2013;8(3):e59187. doi: 10.1371/journal.pone.0059187. Epub Mar. 12, 2013.

Kaspi et al., Xenon difluoride induced aryl iodide reductive elimination: a simple access to difluoropalladium(II) complexes. Inorg Chem. Jan. 7, 2008;47(1):5-7. Epub Dec. 4, 2007.

Khusnutdinova et al., The aerobic oxidation of a Pd(II) dimethyl complex leads to selective ethane elimination from a Pd(III) intermediate. J Am Chem Soc. Feb. 1, 2012;134(4):2414-22. doi: 10.1021/ja210841f. Epub Jan. 20, 2012.

Kilbourn et al., Fluorine-18 labeling of proteins. J Nucl Med. Apr. 1987;28(4):462-70.

Kim et al., An experimental model for peripheral neuropathy produced by segmental spinal nerve ligation in the rat. Pain. Sep. 1992;50(3):355-63.

Kirk, Fluorination in Medicinal Chemistry: Methods, Strategies, and Recent Developments. Org Process Res Dev. 2008;12(2):305-321.

Laali et al., N-(trifluoromethylsulfonyl)aryloxytrifluoromethylsulfoximines [ArO-SO(CF3)=NTf] and N-aryltriflimides Ar-N(Tf)2 by thermal and photolytic dediazoniation of [ArN2] [BF4] in [BMIM] [Tf2N] ionic liquid: exploiting the ambident nucleophilic character of a "nonnucleophilic" anion. J Org Chem. Aug. 31, 2007;72(18):6758-62. Epub Aug. 1, 2007.

(56) References Cited

OTHER PUBLICATIONS

Lanci et al., Oxidatively induced reductive elimination from ((t)Bu2bpy)Pd(Me)2: palladium(IV) intermediates in a one-electron oxidation reaction. J Am Chem Soc. Nov. 4, 2009;131(43):15618-20. doi: 10.1021/ja905816q.

Lasne et al., Chemistry of beta(+)-emitting compounds based on fluorine-18. In: Contrast Agents II. 2002;222:201-58.

Lee et al., A fluoride-derived electrophilic late-stage fluorination reagent for PET imaging. Science. Nov. 4, 2011;334(6056):639-42. doi: 10.1126/science.1212625.

Lee et al., Nickel-mediated oxidative fluorination for PET with aqueous [18F] fluoride. J Am Chem Soc. Oct. 24, 2012;134(42):17456-8. doi: 10.1021/ja3084797. Epub Oct. 12, 2012.

Li et al., Synthesis and local anesthetic activity of fluoro-substituted imipramine and its analogues. Bioorg Med Chem Lett. Jul. 1, 2007;17(13):3733-5. Epub Apr. 10, 2007.

Liang et al., Introduction of fluorine and fluorine-containing functional groups. Angew Chem Int Ed Engl. Aug. 5, 2013;52(32):8214-64. doi: 10.1002/anie.201206566. Epub Jul. 19, 2013.

Liu et al., Oxidative aliphatic C-H fluorination with fluoride ion catalyzed by a manganese porphyrin. Science. Sep. 14, 2012;337(6100):1322-5. doi: 10.1126/science.1222327.

Liu et al., Synthesis and properties of 12-fluororetinal and 12-fluororhodopsin. Model system for fluorine-19 NMR studies of visual pigments. J Am Chem Soc. 1981;103(24):7195-201.

Lockner et al., Practical Radical Cyclizations with Arylboronic Acids and Trifluoroborates. Org. Lett. 2011;13(20):5628-5631.

Lovey et al., Fluorinated retinoic acids and their analogs. 3. Synthesis and biological activity of aromatic 6-fluoro analogs. J Med Chem. 1982;25(1):71-75.

Mack et al., Effect of Chelate Ring Expansion on Jahn—Teller Distortion and Jahn—Teller Dynamics in Copper(II) Complexes. Inorg Chem. 2012;51(14):7851-7858.

Maeda et al., Amino Acids and Peptides. X. : Leu-Enkephalin Analogues Containing a Fluorinated Aromatic Amino Acid. Chem Pharm Bull. 1989;37(3):826-28.

Maimone et al., Evidence for in situ catalyst modification during the Pd-catalyzed conversion of aryl triflates to aryl fluorides. J Am Chem Soc. Nov. 16, 2011;133(45):18106-9. doi: 10.1021/ja208461k. Epub Oct. 21, 2011.

Makleit et al., Synthesis and chemical transformation of halogen-containing morphine derivatives. Magyar Kemikusok Lapja. 1997;52(6):282-89.

Marshall et al., Single-Crystal X-ray and Solution 13C NMR Study of Fluoro(p-nitrophenyl)bis(triphenylphosphine)palladium(II). Are There Effects of Through-Conjugation? Organometallics. 1998;17(24):5427-30.

Matthews et al., Equilibrium acidities of carbon acids. VI. Establishment of an absolute scale of acidities in dimethyl sulfoxide solution. J Am Chem Soc. 1975;97(24):7006-7014.

Mazzotti et al., Palladium(III)—Catalyzed Fluorination of Arylboronic Acid Derivatives. J Am Chem Soc. Sep. 25, 2013;135(38):14012-5. doi: 10.1021/ja405919z. Epub Sep. 16, 2013.

Mcgaraughty et al., Effects of A-317491, a novel and selective P2X3/P2X2/3 receptor antagonist, on neuropathic, inflammatory and chemogenic nociception following intrathecal and intraplantar administration. Br J Pharmacol. Dec. 2003;140(8):1381-8. Epub Nov. 17, 2003.

Mcmurtrey et al., Pd-catalyzed C-H fluorination with nucleophilic fluoride. Pd-catalyzed C-H fluorination with nucleophilic fluoride. Org Lett. Aug. 17, 2012;14(16):4094-7. doi: 10.1021/ol301739f. Epub Jul. 30, 2012.

Mendoza-Espinosa et al., Synthesis of 4- and 4,5-Functionalized Imidazol-2-ylidenes from a Single 4,5-Unsubstituted Imidazol-2-ylidene. J Am Chem Soc. 2010;132(21):7264-7265.

Miao et al., PET of EGFR Expression with an [18]F-Labeled Affibody Molecule. J Nucl Med. 2012;53:1110-1118 (10.2967/jnumed.111.100842).

Miller et al., Synthesis of 11C, 18F, 15O, and 13N radiolabels for positron emission tomography. Angew Chem Int Ed Engl. 2008;47(47):8998-9033. doi: 10.1002/anie.200800222.

Mirica et al., Structure and electronic properties of Pd(III) complexes. Coord Chem Rev. 2013;257(2):299-314.

Muller et al., Fluorine in pharmaceuticals: looking beyond intuition. Science. Sep. 28, 2007;317(5846):1881-6.

Muller et al., The rhodium(II)—catalyzed aziridination of olefins with {[(4-nitropheny)sulfonyl]imino}phenyl-lambda3-iodane. Canadian J of Chem. 1998;76(6):738-750.

Murphy et al., One-pot synthesis of arylboronic acids and aryl trifluoroborates by Ir-catalyzed borylation of arenes. Org Lett. Mar. 1, 2007;9(5):757-60. Epub Feb. 3, 2007.

Murphy et al., Organometallic Fluorides: Compounds Containing Carbonminus signMetalminus signFluorine Fragments of d-Block Metals. Chem Rev. Dec. 18, 1997;97(8):3425-3468.

Nagakura et al., Allodynia and hyperalgesia in adjuvant-induced arthritic rats: time course of progression and efficacy of analgesics. J Pharmacol Exp Ther. Aug. 2003;306(2):490-7. Epub May 1, 2003.

Nesterenko et al., Quantum-Chemical Study of the Mechanism and Regioselectivity of Transannular Cyclization of Dienes of the Bicyclo[3.3.1]nonane Series Treated with Bromosuccinimide and F-TEDA-BF. Theor Exp Chem. 2002;38:156-61.

Niedenzu et al., Boron-nitrogen compounds. 99. Studies on B-(pyrazol-1-yl)pyrazaboles. Inorg Chem. 1984;23(23):3713-3716.

Noel et al., Accelerating palladium-catalyzed C-F bond formation: use of a microflow packed-bed reactor. Angew Chem Int Ed Engl. Sep. 12, 2011;50(38):8900-3. doi: 10.1002/anie.201104652. Epub Aug. 11, 2011.

Nozaki-Taguchi et al., A novel model of primary and secondary hyperalgesia after mild thermal injury in the rat. Neurosci Lett. Sep. 18, 1998;254(1):25-8.

Nyffeler et al., Selectfluor: Mechanistic Insight and Applications. Angew Chem Int Ed Engl. 2004;44(2):192-212.

Onishi et al., Palladium Polypyrazolylborate Complexes Containing A Pd—C Bond. Chem Lett. 1976:955-58.

Ortiz et al., A Convenient Synthesis of Methyl- and Isopropyl-Benzyl Ethers Using Silver(II) Oxide as Reagent. Synth Commun. 1993;23(6):749-56.

Pangborn et al., Safe and Convenient Procedure for Solvent Purification. Organometallics. 1996;15(5):1518-1520.

Park et al., Metabolism of fluorine-containing drugs. Annu Rev Pharmacol Toxicol. 2001;41:443-70.

Pawlikowski et al., Alkyl carbon-nitrogen reductive elimination from platinum(IV)-sulfonamide complexes. J Am Chem Soc. Aug. 29, 2007;129(34):10382-93. Epub Aug. 2, 2007.

Perdew et al., Accurate and simple analytic representation of the electron-gas correlation energy. Phys Rev B Condens Matter. Jun. 15, 1992;45(23):13244-13249.

Pérez et al., Thermal Study of [Pd(2-Phpy)Cl(L)] Complexes (L=pyridines and amines). Journal of Thermal Analysis and Calorimetry. 2001;66(2):361-370.

Phelps, Positron emission tomography provides molecular imaging of biological processes. Proc Natl Acad Sci U S A. Aug. 1, 2000;97(16):9226-33.

Powers et al., Bimetallic palladium catalysis: direct observation of Pd(III)-Pd(III) intermediates. J Am Chem Soc. Dec. 2, 2009;131(47):17050-1. doi: 10.1021/ja906935c.

Powers et al., Bimetallic Pd(III) complexes in palladium-catalysed carbon—heteroatom bond formation. Nat Chem. Jul. 2009;1(4):302-9.

Powers et al., Bimetallic redox synergy in oxidative palladium catalysis. Acc Chem Res. Jun. 19, 2012;45(6):840-50. doi: 10.1021/ar2001974. Epub Oct. 27, 2011.

Powers et al., Bimetallic reductive elimination from dinuclear Pd(III) complexes. J Am Chem Soc. Oct. 13, 2010;132(40):14092-103. doi: 10.1021/ja1036644.

Powers et al., Connecting binuclear Pd(III) and mononuclear Pd(IV) chemistry by Pd-Pd bond cleavage. J Am Chem Soc. Jul. 25, 2012;134(29):12002-9. doi: 10.1021/ja304401u. Epub Jul. 17, 2012.

Powers et al., On the mechanism of palladium-catalyzed aromatic C-H oxidation. J Am Chem Soc. Oct. 20, 2010;132(41):14530-6. doi: 10.1021/ja1054274.

(56) References Cited

OTHER PUBLICATIONS

Powers et al., Palladium(III) in Synthesis and Catalysis. Top Organomet Chem. Jan. 1, 2011;503:129-156.
Privalov et al., Theoretical Studies of the Mechanism of Aerobic Alcohol Oxidation with Palladium Catalyst Systems. Organometallics.2005;24(5):885-893.
Rebstock et al., Synthesis and deprotonation of 2-(pyridyl)phenols and 2-(pyridyl)anilines. Org Biomol Chem. Sep. 7, 2003;1(17):3064-8.
Reed et al., Intermolecular interactions from a natural bond orbital, donor-acceptor viewpoint. Chem Rev. 1988;88(6):899-926.
Roe et al., Structure and Solution Dynamics of [(Ph3P)2Pd(Ph)(Fhf)]. Organometallics. 2000;19(22):4575-82.
Ryabov et al., Synthesis by ligand exchange, structural characterization, and aqueous chemistry of ortho-palladated oximes. Inorg Chem. 1992;31(14):3083-3090.
Sandford, Elemental fluorine in organic chemistry (1997-2006). J Fluorine Chem. 2007;128:90-104.
Sasaki et al., Solid phase synthesis and opioid receptor binding activities of [D-Ala2, D-Leu5]enkephalin analogs containing a fluorinated aromatic amino acid. Chem Pharm Bull (Tokyo). Nov. 1990;38(11):3162-3.
Serguchev et al., Transannular additions of selectfluor and xenon difluoride: regioselectivity and mechanism. J Phys Org Chem. 2011;24(5):407-13.
Sheldrick, A short history of SHELX. Acta Cryst Sect A. 2008;A64:112-122.
Singh et al., Recent highlights in electrophilic fluorination with 1-chloromethyl-4-fluoro-1,4-diazoniabicyclo[2.2.2]octane bis(tetrafluoroborate). Acc Chem Res. Jan. 2004;37(1):31-44.
Sladojevich et al., Late-stage deoxyfluorination of alcohols with PhenoFluor. J Am Chem Soc. Feb. 20, 2013;135(7):2470-3. doi: 10.1021/ja3125405. Epub Feb. 11, 2013.
Still et al., Rapid chromatographic technique for preparative separations with moderate resolution. J Org Chem. 1978;43(14):2923-2925.
Strassman et al., Sensitization of meningeal sensory neurons and the origin of headaches. Nature. Dec. 12, 1996;384(6609):560-4.
Sun et al., Room-temperature nucleophilic aromatic fluorination: experimental and theoretical studies. Angew Chem Int Ed Engl. Apr. 21, 2006;45(17):2720-5.
Szostak et al., Electron transfer reduction of carboxylic acids using SmI2-H2O-Et3N. Org Lett. Feb. 3, 2012;14(3):840-3. doi: 10.1021/ol203361k. Epub Jan. 24, 2012.
Tang et al., Deoxyfluorination of phenols. J Am Chem Soc. Aug. 3, 2011;133(30):11482-4. doi: 10.1021/ja2048072. Epub Jul. 12, 2011.
Tang et al., Silver-catalyzed late-stage fluorination. J Am Chem Soc. Sep. 1, 2010;132(34):121504. doi: 10.1021/ja105834t.
Tang et al., Silver-mediated fluorination of aryl silanes. Tetrahedron. Jun. 17, 2011;67(24):4449-4454.
Taylor et al., Catalytic asymmetric heterogeneous aziridination of styrene using CuHY: effect of nitrene donor on enantioselectivity. J Chem Soc Perkin Trans 2. 2001:1714-1723.
Teare et al., Synthesis and reactivity of [18F]N-fluorobenzenesulfonimide. Chem Commun (Camb). Jun. 21, 2007;2007(23):2330-2.
Thordarson, Determining association constants from titration experiments in supramolecular chemistry. Chem Soc Rev. Mar. 2011;40(3):1305-23. doi: 10.1039/c0cs00062k. Epub Dec. 1, 2010.
Ting et al., Arylfluoroborates and alkylfluorosilicates as potential PET imaging agents: high-yielding aqueous biomolecular 18F-labeling. J Am Chem Soc. Sep. 28, 2005;127(38):13094-5.
Tius et al., The reaction of XeF2 with trialkylvinylstannanes: Scope and some mechanistic observations. Tetrahedron. 1995;51(14):3997-4010.
Tredwell et al., Electrophilic fluorination of organosilanes. Org Biomol Chem. Jan. 7, 2006;4(1):26-32. Epub Nov. 23, 2005.
Trofimenko, Recent advances in poly(pyrazolyl)borate (scorpionate) chemistry. Chem Rev. 1993;93(3):943-980.
Trofimenko, Boron-pyrazole chemistry. II. Poly(1-pyrazolyl)-borates. J Am Chem Soc. 1967;89(13):3170-3177.
Trofimenko, Polypyrazolylborates, a new class of ligands. Acc Chem Res. 1971;4(1):17-22.
Valenzano et al., Pharmacological and pharmacokinetic characterization of the cannabinoid receptor 2 agonist, GW405833, utilizing rodent models of acute and chronic pain, anxiety, ataxia and catalepsy. Neuropharmacology. Apr. 2005;48(5):658-72.
Vasdev et al., On the preparation of fluorine-18 labelled XeF(2) and chemical exchange between fluoride ion and XeF(2). J Am Chem Soc. Oct. 30, 2002;124(43):12863-8.
Vincente et al., Synthesis of Tris- and Tetrakis(pyrazol-1-yl)borate Gold(III) Complexes. Crystal Structures of [Au{κ2-N,N'-BH(Pz)3 } Cl2] (pz=Pyrazol-1-yl) and [Au{κ2-N,N'-B(Pz)4 } (κ2-C,N-C6H4CH2NMe2-2)]ClO4.CHCl3. Inorg Chem. 2002;41(7):1870-1875.
Walker et al., The VR1 antagonist capsazepine reverses mechanical hyperalgesia in models of inflammatory and neuropathic pain. J Pharmacol Exp Ther. Jan. 2003;304(1):56-62.
Wang et al., Versatile Pd(OTf)2 x 2 H2O-catalyzed ortho-fluorination using NMP as a promoter. J Am Chem Soc. Jun. 10, 2009;131(22):7520-1. doi: 10.1021/ja901352k.
Watson et al., Formation of ArF from LPdAr(F): catalytic conversion of aryl triflates to aryl fluorides. Science. Sep. 25, 2009;325(5948):1661-4. doi: 10.1126/science.1178239. Epub Aug. 13, 2009.
Weiss et al., Electrostatic Activation of Hypervalent Organo-Iodine Compounds: Bis(onio)-Substituted Aryliodine(III) Salts. Angew Chem Int Ed. 1994;33(8):891-93.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Woo et al., Direct conversion of pyranose anomeric OH→F→R in the artemisinin family of antimalarial trioxanes. Tetrahedron Lett. 1998;39(12):1533-36.
Xanthos et al., Animal Models of Chronic Pain: Chronic post-ischemia pain: a novel animal model of Complex Regional Pain Syndrome Type I produced by prolonged hindpaw ischemia and reperfusion in the rat. J Pain. 2004;5:S1. Abstract B01.
Yahav et al., Synthesis of the Elusive (R3P)2MF2 (M=Pd, Pt) Complexes. J Am Chem Soc. 2003;125(45):13634-35.
Yahav-Levi et al., Competitive aryl-iodide vs aryl-aryl reductive elimination reactions in Pt(IV) complexes: experimental and theoretical studies. J Am Chem Soc. Jan. 16, 2008;130(2):724-31.
Yaksh et al., An automated flinch detecting system for use in the formalin nociceptive bioassay. J Appl Physiol (1985). Jun. 2001;90(6):2386-402.
Yamada et al., Synthesis and Reaction of New Type I—N. Ylide, N-Tosyliminoiodinane. Chem Lett. 1975;4(4):361-62.
Yandulov et al., Aryl-fluoride reductive elimination from Pd(II): feasibility assessment from theory and experiment. J Am Chem Soc. Feb. 7, 2007;129(5):1342-58.
Ye et al., Mild copper-mediated fluorination of aryl stannanes and aryl trifluoroborates. J Am Chem Soc. Mar. 27, 2013;135(12):4648-51. doi: 10.1021/ja400300g. Epub Mar. 13, 2013.
Zhang et al., Interception of the radicals produced in electrophilic fluorination with radical traps (Tempo, Dmpo) studied by electrospray ionization mass spectrometry. Rapid Commun Mass Spectrom. 2006;20(12):1877-82.
Zhang et al., Investigation of radical cation in electrophilic fluorination by ESI-MS. Org Lett. Sep. 1, 2005;7(18):3877-80.

* cited by examiner

13C NMR spectrum of 2

11B NMR spectrum of 3

11B NMR spectrum of 7

19F NMR spectrum of 7

31P NMR spectrum of 7

HIGH-VALENT PALLADIUM FLUORIDE COMPLEXES AND USES THEREOF

RELATED APPLICATIONS

The present application is a 371 U.S. National Phase of International Application No. PCT/US2009/046401, filed Jun. 5, 2009, published as International Publication No. WO 2009/149347 on Dec. 10, 2009, which claims priority under 35 U.S.C. §119 from U.S. provisional application Ser. No. 61/059,142 filed Jun. 5, 2008, the entire contents of which is incorporated by reference.

BACKGROUND OF THE INVENTION

The regioselective fluorination of organic compounds is an important challenge in the synthesis of pharmaceuticals and agrochemicals (see, for example, Muller et al., *Science* 2007, 317, 1881-1886; Park et al., *Annual Review of Pharmacology and Toxicology* 2001, 41, 443-470; Bohm et al., *ChemBioChem* 2004, 5, 637-643; and Jeschke, *ChemBioChem.* 2004, 5, 570-589).

Syntheses of simple fluoroarenes currently rely on the pyrolysis of diazonium tetrafluoroborates (Balz, G.; Schiemann, G. *Ber. Deut. Chem. Ges.* 1927, 60, 1186-1190), direct fluorination using highly reactive, elemental fluorine (Sandford, J. *Fluorine Chem.* 2007, 128, 90-104), or nucleophilic aromatic substitution reactions of electron-poor aromatic systems by displacement of other halogens or nitro groups (Sun et al., *Angew. Chem., Int. Ed.* 2006, 45, 2720-2725; Adams et al., *Chem. Soc. Rev.* 1999, 28, 225-231). The reductive elimination of arylfluorides from palladium(II) fluoride complexes is an attractive potential alternative that has been investigated by Grushin (Grushin, *Chem.—Eur. J.* 2002, 8, 1006-1014) over the past decade and more recently by Yandulov. A single substrate-p-fluoronitrobenzene—has been prepared successfully in 10% yield in the Yandulov study from a stoichiometric palladium fluoride complex (Yandulov et al., *J. Am. Chem. Soc.* 2007, 129, 1342-1358). Directed electrophilic fluorination of phenylpyridine derivatives and related structures using catalytic palladium(II) acetate and N-fluoropyridinium salts has been reported by Sanford in 2006 (Hull et al., *J. Am. Chem. Soc.* 2006, 128, 7134-7135). Taking advantage of the directing effect of a pyridine substituent, proximal carbon-hydrogen bonds can be fluorinated using microwave irradiation at high temperatures (100-150° C., 1-4 h, 33-75% yield). However, the fact that there is an absence in the literature of any general, functional-group-tolerant fluorination reaction methodology reflects the difficulty of forming carbon-fluorine bonds.

The use of $^{18}$F-labelled organic compounds for positron-emission tomography (PET) requires the controlled, efficient introduction of fluorine into functionalized molecules (see, for example, Couturier et al., *Eur. J. Nucl. Med. Mol. Imaging.* 2004, 31, 1182-1206; Lasne et al., "Chemistry of beta(+)-emitting compounds based on fluorine-18" In *Contrast Agents II,* 2002; Vol. 222, pp 201-258; and Phelps, *Proc. Natl. Acad. Sci. U.S.A.* 2000, 97, 9226-9233). PET has been used to measure presynaptic accumulation of $^{18}$F-fluorodopa tracer in the dopaminergic regions of the brain (see, for example, Ernst et al., "Presynaptic Dopaminergic Deficits in Lesch-Nyhan Disease" *New England Journal of Medicine* (1996) 334:1568-1572), but fluorination of other organic compounds has been difficult due to lack of an appropriate fluorination method.

Despite the utility of fluorinated organic compounds in multiple pharmaceutical, diagnostic, and agrochemical applications, C—F bond formation remains a challenging organic transformation with no broadly applicable solutions.

SUMMARY OF THE INVENTION

While high-valent palladium complexes may be intermediates in the transformations described above, none have been reported to date. Although discrete high-valent palladium fluorides are potential intermediates, electrophilic palladium-carbon bond cleavage is a mechanistic alternative which has not been ruled out. While hundreds of early transition metal fluorides have been structurally characterized (Murphy et al., *Chem. Rev.* 97:3425-3468, 1997; which is incorporated herein by reference), only eight palladium complexes with terminal fluoride ligands can be found in the Cambridge Structural Database, none of which contain a palladium center in an oxidation state other than +2 (Fraser et al., *J. Am. Chem. Soc.* 119:4769-4770, 1997; Marshall et al., *Organometallics,* 17:5427-5430, 1998; Roe et al., *Organometallics,* 19: 4575-4582, 2000; Grushin et al., *Angew. Chem. Int. Ed.,* 41:4476-4479, 2002; Yahav et al., *J. Am. Chem. Soc.* 125: 13634-13635, 2003; Jasim et al., *Organometallics,* 23:6140-6149, 2004; each of which is incorporated herein by reference).

The present invention provides novel high-valent palladium fluoride complexes and method of using these complexes in the fluorination of organic compounds. The inventive system is particularly useful in preparing $^{18}$F-labeled compounds for PET imaging. The complexes are typically palladium(IV) fluoride complexes as described herein. The complexes include two fixed ligands that stabilize the high-valent palladium complex. In certain embodiments, one of the ligands is a bidentate ligand, and the other ligand is a tridentate ligand. The inventive system was envisioned due to the limited nature of nucleophilic F$^-$ chemistry. The inventive system relies on the transfer of electrophilic F$^+$, which is analogous to the commercially available fluorinating reagent, Selectflour® (N-chloromethyl-N'-fluorotriethylenediammonium bis(tetrafluoroborate)).

In one aspect, the invention features a palladium complex of formula (I):

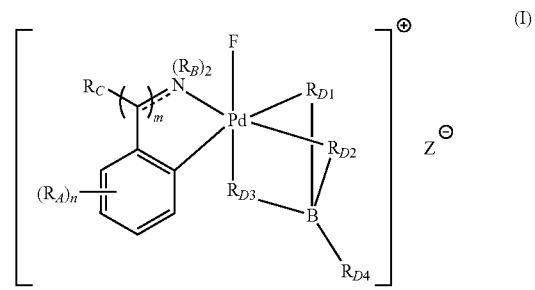

wherein:
the dashed line represents the presence or absence of a bond;
Pd has a valency of +4;
n is an integer between 0 and 4, inclusive;
m is an integer between 0 and 3, inclusive;
each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two RA may be taken together to form a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring;

$R_{D1}$, $R_{D2}$, $R_{D3}$, and $R_{D4}$ are each independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl;

$Z^-$ is an anion such as halide, acetate, tosylate, azide, tetrafluoroborate, tetraphenylborate, tetrakis(pentafluorophenyl)borate, $[B[3,5-(CF_3)_2C_6H_3]_4]^-$, hexafluorophosphate, phosphate, sulfate, perchlorate, trifluoromethanesulfonate or hexafluoroantimonate; and F comprises $^{18}$F or $^{19}$F.

In some embodiments, $R_C$ is hydrogen. In some embodiments, $R_C$ is methyl.

In some embodiments, n is 0. In some embodiments, n is 1. In some embodiments, n is 2.

In some embodiments, two $R_A$ are taken together to form an aryl ring (e.g., a phenyl ring).

In some embodiments, m is 1. In some embodiments, m is 2.

In some embodiments, at least one $R_B$ is hydrogen. In some embodiments, both $R_B$ are hydrogen. In some embodiments, at least one $R_B$ is $C_1$-$C_6$ alkyl. In some embodiments, both $R_B$ are methyl.

In some embodiments, $R_B$ and $R_C$ are taken together form a heterocyclic ring. In some embodiments, $R_B$ and $R_C$ taken together form a heteroaryl ring (e.g., a pyridyl ring).

In some embodiments, $R_A$ and $R_C$ are taken together form an aryl ring (e.g., a phenyl ring).

In some embodiments, the dashed line represents the absence of a bond. In some embodiments, the dashed line represents the presence of a bond.

In some embodiments, $R_{D1}$, $R_{D2}$, $R_{D3}$ and $R_{D4}$ are each a 5-membered heteroaryl ring. In some embodiments, $R_{D1}$, $R_{D2}$, $R_{D3}$ and $R_{D4}$ are each a pyrazolyl ring (e.g., an unsubstituted pyrazolyl ring).

In some embodiments, $R_{D1}$, $R_{D2}$ and $R_{D3}$ are each a 5-membered heteroaryl ring, and $R_{D4}$ is an alkyl group. In some embodiments, $R_{D1}$, $R_{D2}$ and $R_{D3}$ are each a pyrazolyl ring, and $R_{D4}$ is a tert-butyl group. In some embodiments, $R_{D1}$, $R_{D2}$ and $R_{D3}$ are each a pyrazolyl ring, and $R_{D4}$ is an n-butyl group.

In some embodiments, $R_{D1}$, $R_{D2}$ and $R_{D3}$ are each a 5-membered heteroaryl ring, and $R_{D4}$ is an aryl group. In some embodiments, $R_{D1}$, $R_{D2}$ and $R_{D3}$ are each a pyrazolyl ring, and $R_{D4}$ is a phenyl ring.

In some embodiments, $R_{D1}$ and $R_{D2}$ are each a 5-membered heteroaryl ring, $R_{D3}$ is an alkoxy group and $R_{D4}$ is an alkyl group. In some embodiments, $R_{D1}$ and $R_{D2}$ are each a pyrazolyl ring, $R_{D3}$ is an isopropoxy group and $R_{D4}$ is a tert-butyl group. In some embodiments, $R_{D1}$ and $R_{D2}$ are each a pyrazolyl ring, $R_{D3}$ is an isopropoxy group and $R_{D4}$ is an n-butyl group.

In some embodiments, $R_{D1}$ and $R_{D2}$ are each a 5-membered heteroaryl ring, $R_{D3}$ is an alkoxy group and $R_{D4}$ is an aryl group. In some embodiments, $R_{D1}$ and $R_{D2}$ are each a pyrazolyl ring, $R_{D3}$ is an isopropoxy group and $R_{D4}$ is a phenyl ring.

In some embodiments, the anion is trifluoromethanesulfonate. In some embodiments, the anion is hexafluorophosphate. In some embodiments, the anion is a halide.

In some embodiments, the complex has the following formula:

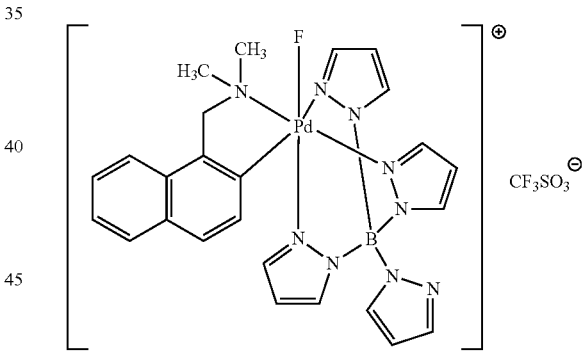

In some embodiments, the complex has the following formula:

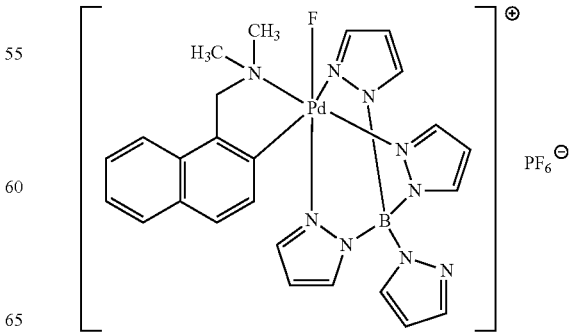

In one aspect, the invention features a method of fluorinating an organic compound, the method comprising mixing a palladium complex of formula (I) with a substrate under conditions sufficient to fluorinate the substrate, thereby providing a fluorinated organic compound.

In some embodiments, the fluorinated organic compound comprises $^{18}F$ or $^{19}F$.

In some embodiments, the substrate is an organic compound comprising an enol silyl ether, and the fluorinated organic compound is an α-fluorinated ketone. In some embodiments, the substrate is a palladium(II) aryl complex, and the fluorinated organic compound is a fluorinated aryl compound. In some embodiments, the substrate is an arylsilver complex, and the fluorinated organic compound is a fluorinated aryl compound.

In some embodiments, the method further comprises a solvent. In some embodiments, the solvent is a polar aprotic solvent (e.g., methylene chloride, dichloroethane or tetrahydrofuran). In some embodiments, the solvent is a nonpolar solvent (e.g., benzene).

In some embodiments, the method further comprises an inert atmosphere. In some embodiments, the reaction is performed under anhydrous conditions. In some embodiments, the reaction comprises a source of energy. In some embodiments, the reaction comprises heat.

In some embodiments, the fluorinated organic compound comprises an aryl group. In some embodiments, the fluorinated organic compound is an imaging agent (e.g., a PET imaging agent). In some embodiments, the fluorinated organic compound is a pharmaceutically acceptable compound or a prodrug thereof.

In one aspect, the invention features a method of storing a palladium complex of formula (I), the method comprising maintaining the palladium complex in a sealed container for at least 12 hours.

In some embodiments, the sealed container is a vial. In some embodiments, the sealed container is an ampule. In some embodiments, the sealed container is substantially free of dioxygen. In some embodiments, the sealed container contains an inert gas.

In one aspect, the invention features a composition comprising a palladium complex of formula (I) and an additional component.

In some embodiments, the component is a substrate. In some embodiments, the substrate is an organic compound comprising an enol silyl ether. In some embodiments, the substrate is a palladium(II) aryl complex. In some embodiments, the substrate is an arylsilver complex.

In some embodiments, the component is a reagent. In some embodiments, the composition comprises a plurality of reagents.

In some embodiments, the component is a solvent. In some embodiments, the solvent is a polar aprotic solvent (e.g., methylene chloride, dichloroethane or tetrahydrofuran). In some embodiments, the solvent is a nonpolar solvent (e.g., benzene).

In one aspect, the invention features a kit comprising a palladium complex of formula (I) and a container.

In some embodiments, the container is a vial. In some embodiments, the container is a sealed ampule. In some embodiments, the container is substantially free of dioxygen. In some embodiments, the container contains an inert gas.

In some embodiments, the kit further comprises instructions for use of the palladium complex. In some embodiments, the kit further comprises a reagent.

In some embodiments, the kit further comprises a substrate. In some embodiments, the substrate is an organic compound comprising an enol silyl ether. In some embodiments, the substrate is a palladium(II) aryl complex. In some embodiments, the substrate is an arylsilver complex.

In one aspect, the invention features a palladium complex of formula (II):

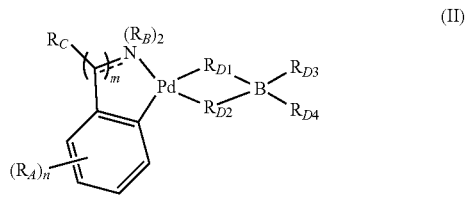

(II)

wherein
the dashed line represents the presence or absence of a bond;
Pd has a valency of +2;
n is an integer between 0 and 4, inclusive;
m is an integer between 0 and 3, inclusive;
each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to form a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; wherein $R_C$ and $R_B$ may be taken together to fawn a substituted or unsubstituted heterocyclic or heteroaryl ring; and wherein $R_C$ and $R_A$ may be taken together to form a substituted or unsubstituted carbocyclic, heterocyclic, aryl or heteroaryl ring; and $R_{D1}$, $R_{D2}$, $R_{D3}$, and $R_{D4}$ are each independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl;

In some embodiments, $R_C$ is hydrogen. In some embodiments, $R_C$ is methyl.

In some embodiments, n is 0. In some embodiments, n is 1. In some embodiments, n is 2.

In some embodiments, two $R_A$ are taken together to form an aryl ring (e.g., a phenyl ring).

In some embodiments, m is 1. In some embodiments, m is 2.

In some embodiments, at least one $R_B$ is hydrogen. In some embodiments, both $R_B$ are hydrogen. In some embodiments, at least one $R_B$ is $C_1$-$C_6$ alkyl (e.g., methyl).

In some embodiments, $R_B$ and $R_C$ are taken together form a heterocyclic ring. In some embodiments, $R_B$ and $R_C$ taken together form a heteroaryl ring (e.g., a pyridyl ring).

In some embodiments, $R_A$ and $R_C$ are taken together form an aryl ring (e.g., a phenyl ring).

In some embodiments, the dashed line represents the absence of a bond. In some embodiments, the dashed line represents the presence of a bond.

In some embodiments, $R_{D1}$, $R_{D2}$, $R_{D3}$ and $R_{D4}$ are each a 5-membered heteroaryl ring. In some embodiments, $R_{D1}$, $R_{D2}$, $R_{D3}$ and $R_{D4}$ are each a pyrazolyl ring (e.g., an unsubstituted pyrazolyl ring).

In some embodiments, $R_{D1}$, $R_{D2}$ and $R_{D3}$ are each a 5-membered heteroaryl ring, and $R_{D4}$ is an alkyl group. In some embodiments, $R_{D1}$, $R_{D2}$ and $R_{D3}$ are each a pyrazolyl ring, and $R_{D4}$ is a tert-butyl group. In some embodiments, $R_{D1}$, $R_{D2}$ and $R_{D3}$ are each a pyrazolyl ring, and $R_{D4}$ is an n-butyl group.

In some embodiments, $R_{D1}$, $R_{D2}$ and $R_{D3}$ are each a 5-membered heteroaryl ring, and $R_{D4}$ is an aryl group. In some embodiments, $R_{D1}$, $R_{D2}$ and $R_{D3}$ are each a pyrazolyl ring, and $R_{D4}$ is a phenyl ring.

In some embodiments, $R_{D1}$ and $R_{D2}$ are each a 5-membered heteroaryl ring, $R_{D3}$ is an alkoxy group and $R_{D4}$ is an alkyl group. In some embodiments, $R_{D1}$ and $R_{D2}$ are each a pyrazolyl ring, $R_{D3}$ is an isopropoxy group and $R_{D4}$ is a tert-butyl group. In some embodiments, $R_{D1}$ and $R_{D2}$ are each a pyrazolyl ring, $R_{D3}$ is an isopropoxy group and $R_{D4}$ is an n-butyl group.

In some embodiments, $R_{D1}$ and $R_{D2}$ are each a 5-membered heteroaryl ring, $R_{D3}$ is an alkoxy group and $R_{D4}$ is an aryl group. In some embodiments, $R_{D1}$ and $R_{D2}$ are each a pyrazolyl ring, $R_{D3}$ is an isopropoxy group and $R_{D4}$ is a phenyl ring.

In some embodiments, the palladium complex has the following formula:

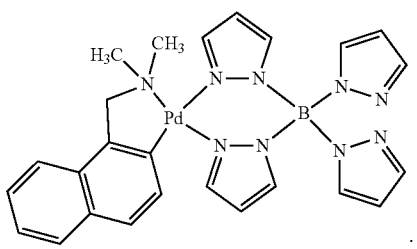

In one aspect, the invention features a method of fluorinating an organic compound, the method comprising reacting a palladium complex of formula (II) with a fluorinating agent and a substrate, under conditions sufficient to fluorinate the substrate, thereby providing a fluorinated organic compound.

In some embodiments, the substrate is an organic compound comprising an enol silyl ether, and the fluorinated organic compound is an α-fluorinated ketone. In some embodiments, the substrate is a palladium(II) aryl complex, and the fluorinated organic compound is a fluorinated aryl compound. In some embodiments, the substrate is an arylsilver complex, and the fluorinated organic compound is a fluorinated aryl compound.

In some embodiments, the fluorinating agent comprises $^{18}F$ or $^{19}F$. In some embodiments, the fluorinating agent is N-chloromethyl-N'-fluorotriethylenediammonium bis(tetrafluoroborate) (Selectfluor®). In some embodiments, the fluorinating agent is $XeF_2$. In some embodiments, the fluorinating agent is N-fluoropyridinium trifluoromethanesulfonate. In some embodiments, the fluorinating agent is N-fluoro-2,4,6-trimethylpyridinium hexafluorophosphate.

In some embodiments, the method further comprises a solvent. In some embodiments, the solvent is a polar aprotic solvent (e.g., methylene chloride, dichloroethane or tetrahydrofuran). In some embodiments, the solvent is a nonpolar solvent (e.g., benzene).

In some embodiments, the method further comprises an inert atmosphere. In some embodiments, the reaction is performed under anhydrous conditions. In some embodiments, the reaction comprises a source of energy. In some embodiments, the reaction comprises heat.

In some embodiments, the palladium complex of formula (II) is combined with the fluorinating agent prior to the addition of the substrate.

In some embodiments, the method proceeds via an intermediate palladium complex of formula (I). In some embodiments, the intermediate palladium complex is isolated.

In some embodiments, the fluorinated organic compound is an imaging agent (e.g., a PET imaging agent). In some embodiments, the fluorinated organic compound is a pharmaceutically acceptable compound or a prodrug thereof.

In one aspect, the invention features a method of making a fluorinated Pd(IV) complex, the method comprising reacting a palladium complex of formula (II) with a fluorinating agent, to provide the fluorinated Pd(IV) complex.

In some embodiments, the fluorinating agent comprises $^{18}F$ or $^{19}F$. In some embodiments, the fluorinating agent is N-chloromethyl-N'-fluorotriethylenediammonium bis(tetrafluoroborate) (Selectfluor®). In some embodiments, the fluorinating agent is $XeF_2$. In some embodiments, the fluorinating agent is N-fluoropyridinium trifluoromethanesulfonate. In some embodiments, the fluorinating agent is N-fluoro-2,4,6-trimethylpyridinium hexafluorophosphate.

In some embodiments, the method further comprises a solvent. In some embodiments, the solvent is a polar aprotic solvent (e.g., methylene chloride, dichloroethane or tetrahydrofuran). In some embodiments, the solvent is a nonpolar solvent (e.g., benzene).

In some embodiments, the method further comprises an inert atmosphere. In some embodiments, the reaction is performed under anhydrous conditions. In some embodiments, the reaction comprises a source of energy. In some embodiments, the reaction comprises heat.

In one aspect, the invention features a method of storing a palladium complex of formula (II), the method comprising maintaining the palladium complex in a sealed container for at least 12 hours.

In some embodiments, the sealed container is a vial. In some embodiments, the sealed container is an ampule. In some embodiments, the sealed container is substantially free of dioxygen. In some embodiments, the sealed container contains an inert gas.

In one aspect, the invention features a composition comprising a palladium complex of formula (II) and an additional component.

In some embodiments, the component is a fluorinating agent. In some embodiments, the fluorinating agent comprises $^{18}F$ or $^{19}F$. In some embodiments, the fluorinating agent is N-chloromethyl-N'-fluorotriethylenediammonium bis(tetrafluoroborate) (Selectfluor®). In some embodiments, the fluorinating agent is $XeF_2$. In some embodiments, the fluorinating agent is N-fluoropyridinium trifluoromethanesulfonate. In some embodiments, the fluorinating agent is N-fluoro-2,4,6-trimethylpyridinium hexafluorophosphate.

In some embodiments, the component is a substrate. In some embodiments, the substrate is an organic compound comprising an enol silyl ether. In some embodiments, the substrate is a palladium(II) aryl complex. In some embodiments, the substrate is an arylsilver complex.

In some embodiments, the component is a reagent. In some embodiments, the composition comprises a plurality of reagents.

In some embodiments, the component is a solvent. In some embodiments, the solvent is a polar aprotic solvent (e.g., methylene chloride, dichloroethane or tetrahydrofuran). In some embodiments, the solvent is a nonpolar solvent (e.g., benzene).

In one aspect, the invention features a kit comprising a palladium complex of formula (II) and a container.

In some embodiments, the container is a vial. In some embodiments, the container is a sealed ampule. In some embodiments, the container is substantially free of dioxygen. In some embodiments, the container contains an inert gas.

In some embodiments, the kit further comprises instructions for use of the palladium complex.

In some embodiments, the kit further comprises a reagent. In some embodiments, the reagent is a fluorinating agent. In some embodiments, the fluorinating agent comprises $^{18}F$ or $^{19}F$. In some embodiments, the fluorinating agent is N-chloromethyl-N'-fluorotriethylenediammonium bis(tetrafluoroborate) (Selectfluor®). In some embodiments, the fluorinating agent is $XeF_2$. In some embodiments, the fluorinating agent is N-fluoropyridinium trifluoromethanesulfonate. In some embodiments, the fluorinating agent is N-fluoro-2,4,6-trimethylpyridinium hexafluorophosphate.

In some embodiments, the kit further comprises a substrate. In some embodiments, the substrate is an organic compound comprising an enol silyl ether. In some embodiments, the substrate is a palladium(II) aryl complex. In some embodiments, the substrate is a arylsilver complex.

In one aspect, the invention features a method of preparing a palladium fluoride complex of formula:

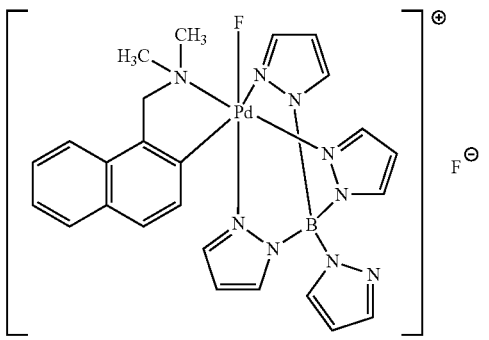

the method comprising steps of:
reacting a palladium chloride complex of formula:

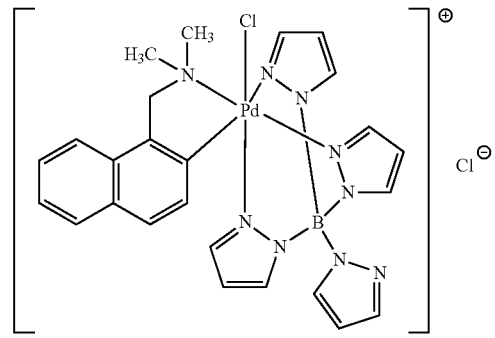

with nucleophilic F⁻ under suitable conditions to yield a complex of formula:

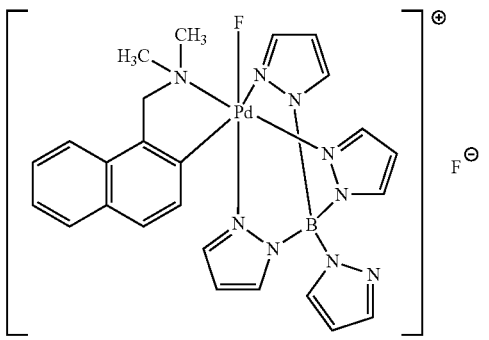

In some embodiments, the nucleophilic F⁻ is provided by AgF. In some embodiments, the nucleophilic F⁻ is $^{18}F^-$.

This application refers to various issued patents, published patent applications, journal articles, and other publications, all of which are incorporated herein by reference.

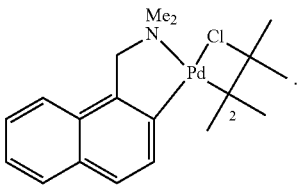

Figure 4:
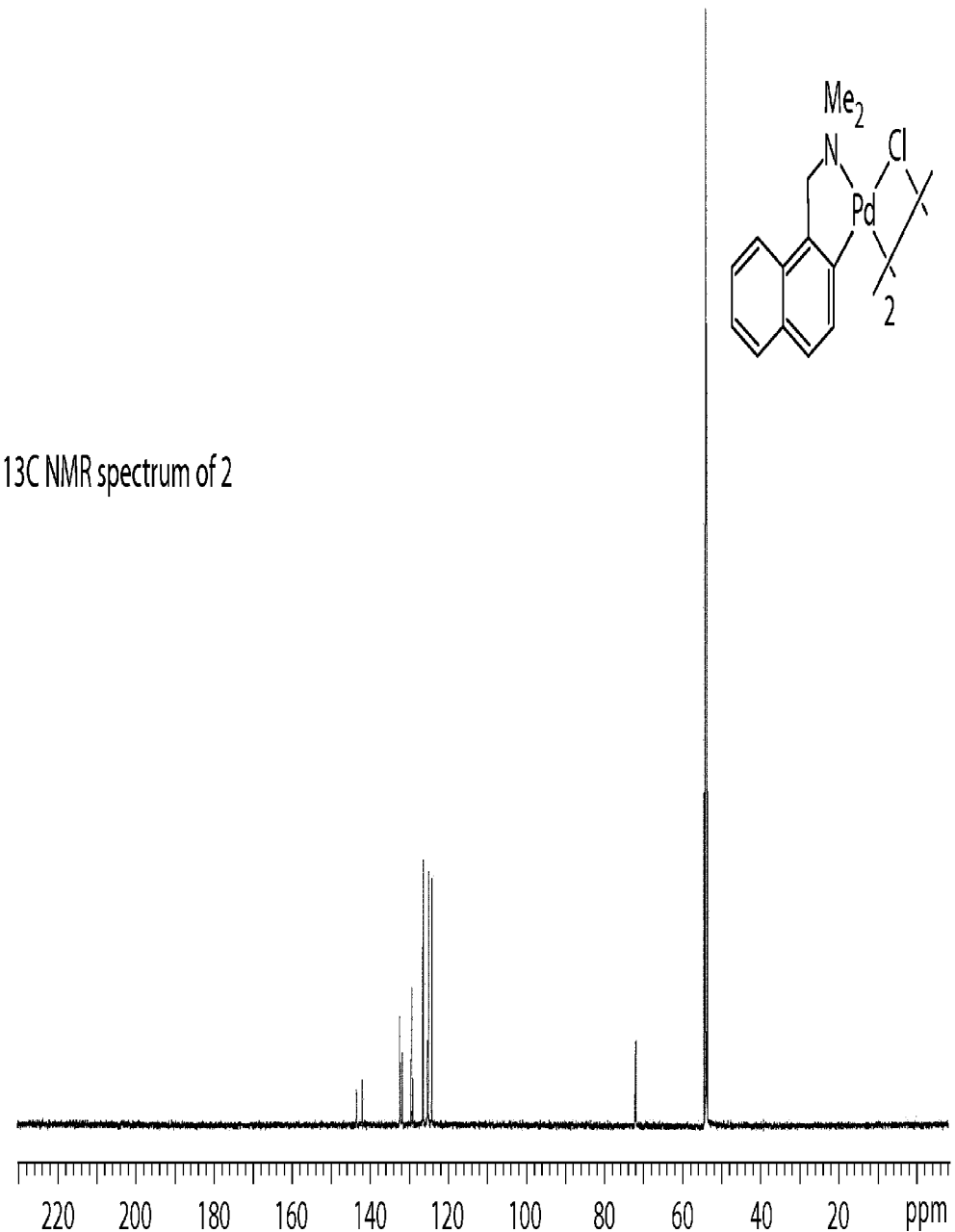

FIG. 4 is a $^{13}$C NMR spectrum of the palladium(II) chloride dimer:

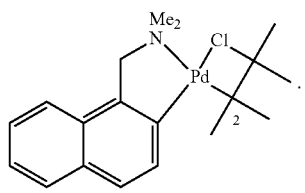

Figure 5:
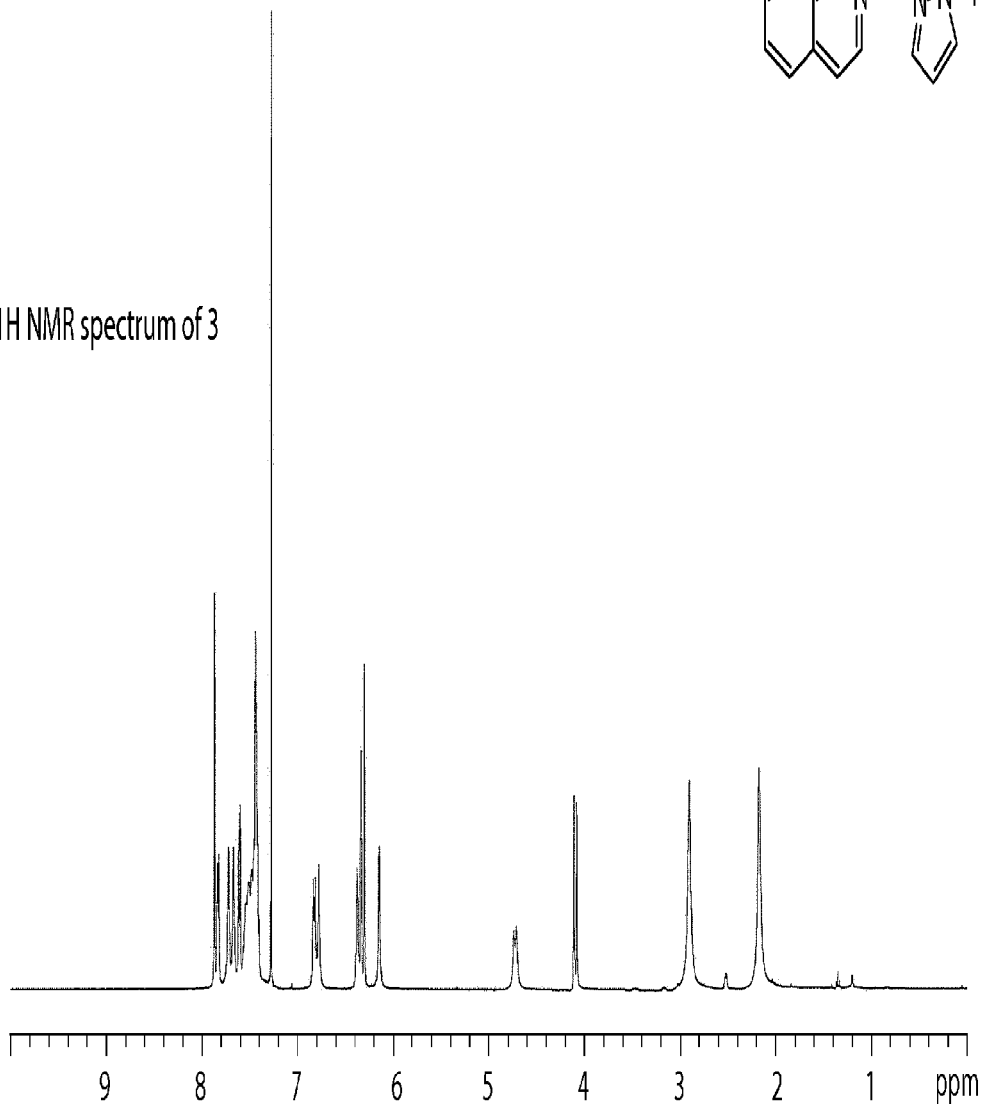

FIG. 5 is $^{1}$H NMR spectrum of the palladium(II) borate:

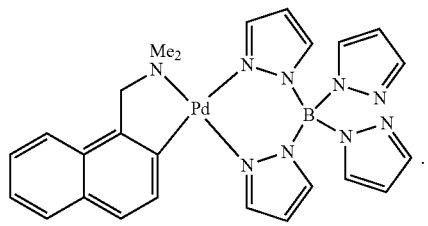

Figure 6:
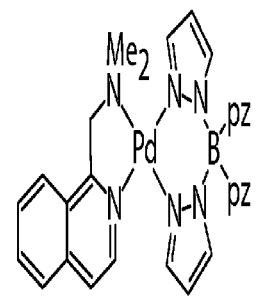
Figure 6:
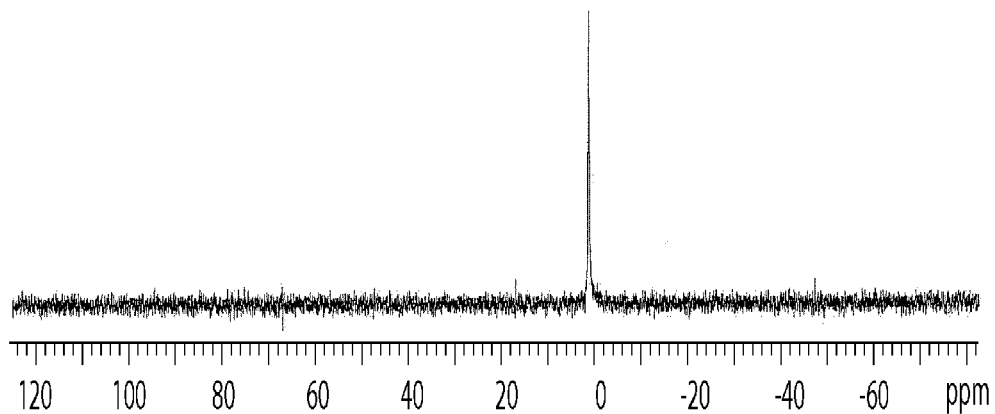

FIG. 6 is $^{11}$B NMR spectrum of the palladium(II) borate:

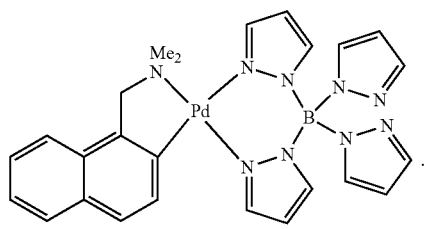

Figure 7:
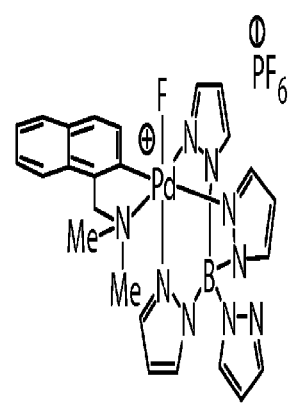
Figure 7:
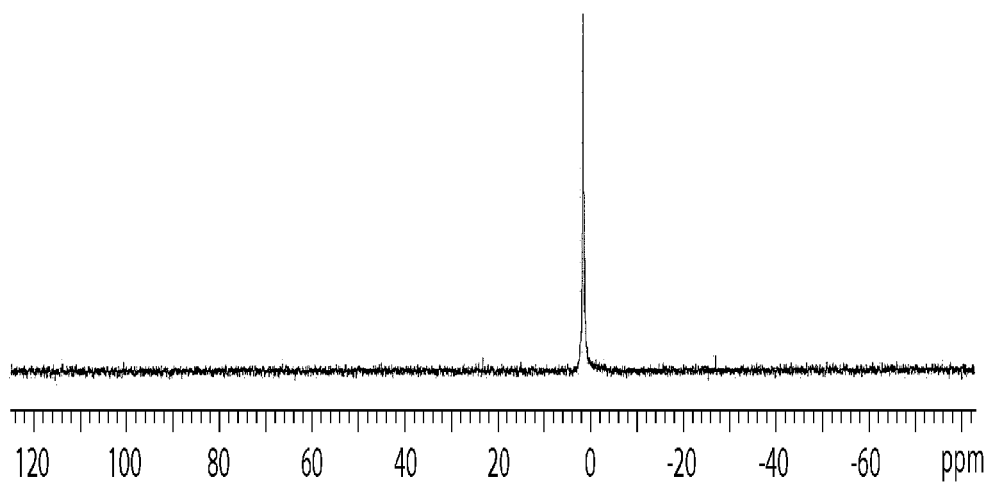

FIG. 7 is $^{11}$B NMR spectrum of the palladium(IV) fluoride complex:

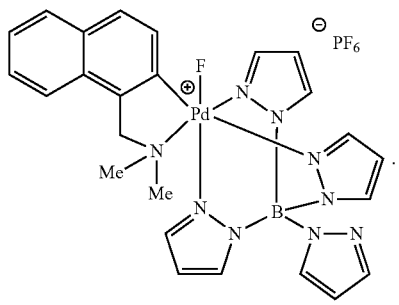

Figure 8:
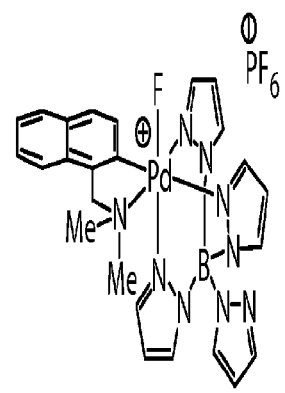
Figure 8:
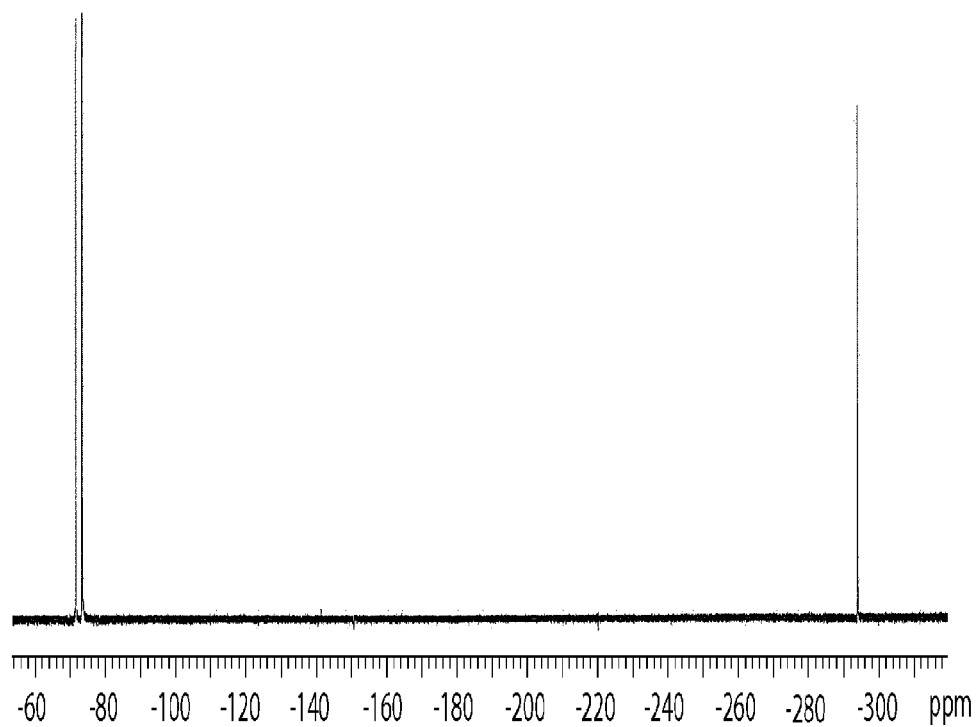

FIG. 8 is $^{19}$F NMR spectrum of the palladium(IV) fluoride complex:

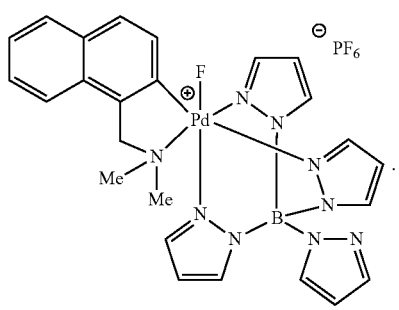

Figure 9:
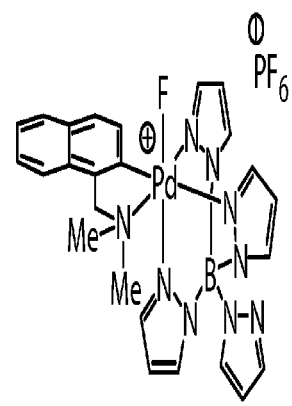
Figure 9:
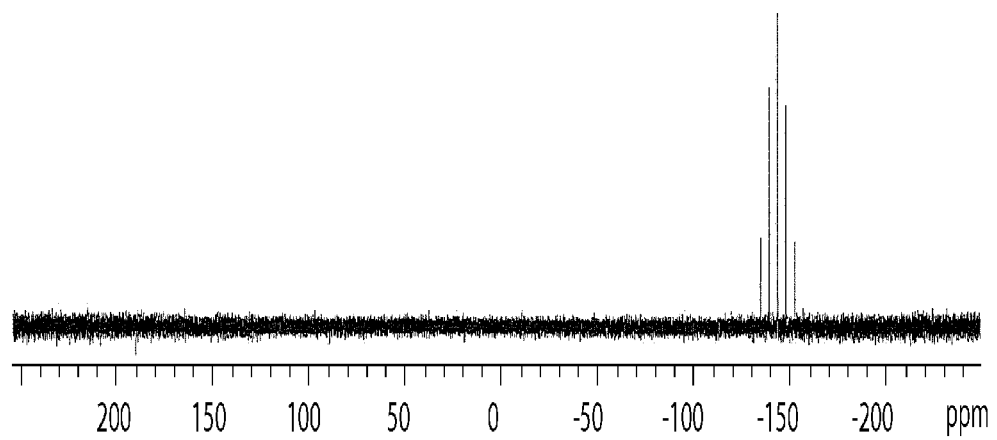

FIG. 9 is $^{31}$P NMR spectrum of the palladium(IV) fluoride complex:

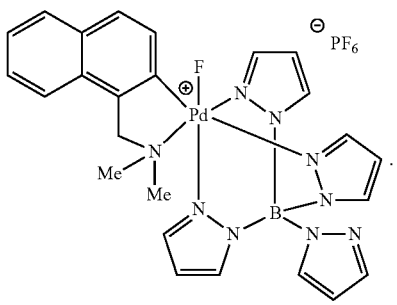

DEFINITIONS

Definitions of specific functional groups and chemical terms are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

Certain compounds of the present invention can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N.Y., 1962); Wilen, *Tables of Resolving Agents and Optical Resolutions* p. 268 (E. L. Eliel, Ed., Univ. of Notre Dame Press, Notre Dame, Ind. 1972).

As used herein, a "bond" refers to a single bond.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-10 carbon atoms. In certain embodiments, aliphatic groups contain 1-8 carbon atoms, 1-7 carbon atoms, 1-6 carbon atoms, 1-5 carbon atoms, 1-4 carbon atoms, 1-3 carbon atoms, or 1-2 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more double or triple bonds.

The terms "carbocyclyl" and "carbocyclic" refer to saturated or partially unsaturated cyclic aliphatic monocyclic or bicyclic ring systems, as described herein, having from 3 to 10 members, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In certain embodiments, the cycloalkyl has 3-6 carbons. The terms "cycloaliphatic", "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring.

The term "alkyl," as used herein, refers to saturated, straight- or branched-chain hydrocarbon radicals derived from an aliphatic moiety containing between one and six carbon atoms by removal of a single hydrogen atom. In certain embodiments, the alkyl group employed in the invention contains 1-10 carbon atoms. In certain embodiments, the alkyl group employed contains 1-8 carbon atoms, 1-7 carbon atoms, 1-6 carbon atoms, 1-5 carbon atoms, 1-4 carbon atoms, 1-3 carbon atoms, or 1-2 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, the alkenyl group employed in the invention contains 2-10 carbon atoms. In certain embodiments, the alkenyl group employed in the invention contains 2-8 carbon atoms, 2-7 carbon atoms, 2-6 carbon atoms, 2-5 carbon atoms, 2-4 carbon atoms, 2-3 carbon atoms or 2 carbon atoms. Alkenyl groups include, for example, ethenyl, propenyl, butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, the alkynyl group employed in the invention contains 2-10 carbon atoms. In certain embodiments, the alkynyl group employed in the invention contains 2-8 carbon atoms, 2-7 carbon atoms, 2-6 carbon atoms, 2-5 carbon atoms, 2-4 carbon atoms, 2-3 carbon atoms or 2 carbon atoms. Representative alkynyl groups include, but are not limited to, ethynyl, 2-propynyl (propargyl), 1-propynyl, and the like.

The term "aryl" refers to monocyclic, bicyclic or tricyclic aromatic ring system having a total of five to 14 ring members, wherein at least one ring in the system is aromatic and wherein each ring in the system contains three to seven ring members. The term "aryl" may be used interchangeably with the term "aryl ring". In certain embodiments of the present invention, "aryl" refers to a monocyclic or polycyclic aromatic ring system which includes, but is not limited to, phenyl, biphenyl, naphthyl, anthracyl, phenanthrenyl, phenalenyl, and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The term "heteroaryl" refers to a monocyclic, bicyclic or tricyclic aromatic ring system having 5 to 14 ring atoms, wherein the ring atoms include carbon atoms and from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring" any of which terms include rings that are optionally substituted.

As used herein, the terms "heterocyclyl" and "heterocyclic ring" are used interchangeably and refer to a monocyclic, bicyclic or tricyclic nonaromatic ring system that is either saturated or partially unsaturated, and having, in addition to carbon atoms, one to five heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", and "heterocyclyl ring", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R'$; —$(CH_2)_{0-4}OR'$; —O—$(CH_2)_{0-4}C(O)OR'$; —$(CH_2)_{0-4}$—$CH(OR')_2$; —$(CH_2)_{0-4}SR'$; —$(CH_2)_{0-4}Ph$, which may be substituted with R'; —$(CH_2)_{0-4}O(CH_2)_{0-1}Ph$ which may be substituted with R'; —CH=CHPh, which may be substituted with R'; —$NO_2$; —CN; —$N_3$; —$(CH_2)_{0-4}N(R')_2$; —$(CH_2)_{0-4}N(R')C(O)R'$; —N(R')C(S)R'; —$(CH_2)_{0-4}N(R')C(O)NR'_2$; —N(R')C(S)NR'$_2$; —$(CH_2)_{0-4}N(R')C(O)OR'$; —N(R')N(R')C(O)R'; —N(R')N(R')C(O)NR'$_2$; —N(R')N(R')C(O)OR'; —$(CH_2)_{0-4}C(O)R°$; —C(S)R°; —$(CH_2)_{0-4}C(O)OR'$; —$(CH_2)_{0-4}C(O)SR'$; —$(CH_2)_{0-4}C(O)OSiR'_3$; —$(CH_2)_{0-4}OC(O)R'$; —OC(O)$(CH_2)_{0-4}SR$—, SC(S)SR'; —$(CH_2)_{0-4}SC(O)R'$; —$(CH_2)_{0-4}C(O)NR'_2$; —C(S)NR'$_2$; —C(S)SR'; —SC(S)SR', —$(CH_2)_{0-4}OC(O)NR'_2$; —C(O)N(OR')R'; —C(O)C(O)R'; —C(O)CH$_2$C(O)R'; —C(NOR')R'; —$(CH_2)_{0-4}SSR'$; —$(CH_2)_{0-4}S(O)_2R'$; —$(CH_2)_{0-4}S(O)_2OR'$; —$(CH_2)_{0-4}OS(O)_2R'$; —S(O)$_2$NR'$_2$; —$(CH_2)_{0-4}S(O)R'$; —N(R')S(O)$_2$NR'$_2$; —N(R')S(O)$_2$R'; —N(OR')R'; —C(NH)NR'$_2$; —P(O)$_2$R'; —P(O)R'$_2$; —OP(O)R'$_2$; —OP(O)(OR')$_2$; SiR'$_3$; —$(C_{1-4}$ straight or branched alkylene)O—N(R')$_2$; or —$(C_{1-4}$ straight or branched alkylene)C(O)O—N(R')$_2$, wherein each R' may be substituted as defined below and is independently hydrogen, $C_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R', taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R' (or the ring formed by taking two independent occurrences of R' together with their intervening atoms), are independently halogen, —$(CH_2)_{0-2}R''$, -(haloR''), —$(CH_2)_{0-2}OH$, —$(CH_2)_{0-2}OR''$, —$(CH_2)_{0-2}CH(OR'')_2$; —O(haloR''), —CN, —$N_3$, —$(CH_2)_{0-2}C(O)R''$, —$(CH_2)_{0-2}C(O)OH$, —$(CH_2)_{0-2}C(O)OR''$, —$(CH_2)_{0-2}SR''$, —$(CH_2)_{0-2}SH$, —$(CH_2)_{0-2}NH_2$, —$(CH_2)_{0-2}NHR''$, —$(CH_2)_{0-2}NR''_2$, —$NO_2$, —SiR'$_3$, —OSiR'$_3$, —C(O)SR'', —$(C_{1-4}$ straight or branched alkylene)C(O)OR'', or —SSR'' wherein each R'' is unsubstituted or where preceded by "halo" is substituted only with one or more halogens, and is independently selected from $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R' include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R'', -(haloR''), —OH, —OR'', —O(haloR''), —CN, —C(O)OH, —C(O)OR'', —NH$_2$, —NHR'', —NR''$_2$, or —NO$_2$, wherein each R'' is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R'', —(haloR''), —OH, —OR'', —O(haloR''), —CN, —C(O)OH, —C(O)OR'', —NH$_2$, —NHR'', —NR''$_2$, or —NO$_2$, wherein each R'' is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

An "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenyl)-pethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4 methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydropyranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, dimethoxybenzyl, o-nitrobenzyl, p-nitrobenzyl, p-halobenzyl, 2,6-dichlorobenzyl, p-cyanobenzyl, p-phenylbenzyl, 2-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro 4 methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro 4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene)derivative (TIPDS), tetra-t-butoxydisiloxane-1,3-diylidene derivative (TBDS), cyclic carbonates, cyclic boronates, ethyl boronate, and phenyl boronate.

A "pharmaceutically acceptable form thereof" includes any pharmaceutically acceptable salts, isomers, and/or polymorphs of a palladium complex, or any pharmaceutically acceptable salts, prodrugs and/or isomers of an organic compound, as described below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+$ $(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. The compounds of the invention readily undergo dehydration to form oligomeric anhydrides by dehydration of the boronic acid moiety to form dimers, trimers, and tetramers, and mixtures thereof. These oligomeric species hydrolyze under physiological conditions to reform the boronic acid. As such, the oligomeric anhydrides are contemplated as a "prodrug" of the compounds of the present invention, and may be used in the treatment of disorder and/or conditions a wherein the inhibition of FAAH provides a therapeutic effect.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

As used herein, "polymorph" refers to a crystalline complex or compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

As used herein "coordinated" means the organic compound is associated with the palladium atom.

DETAILED DESCRIPTION OF CERTAIN EMBODIMENTS OF THE INVENTION

The present invention provides novel high-valent palladium fluoride complexes. The complexes have terminal fluoride ligands, and the palladium center has an oxidation state greater than +2. In certain embodiments, the palladium center has an oxidation state of +4.

The ligands surrounding the complex stabilize the octahedral coordination sphere, thus disfavoring reductive elimination and other reductive pathways. These complexes are useful in transferring a eletrophilic $F^+$ to an organic compound. In particular, the inventive complexes are useful in labelling a compound with $^{18}F$ for positron emission tomography (PET). Also described herein are compositions, reaction mixtures and kits comprising the palladium complexes. Also described herein are methods for fluorinating organic compounds using a palladium complex, e.g., a palladium complex described herein.

High-Valent Palladium Complexes

The present invention provides novel high-valent palladium fluoride complexes. In certain embodiments, the complex is a Pd (IV) complex. Typically, the complex comprises one or more bidentate or tridentate ligands. Such ligands, particularly "scorpionate ligands," are thought to stabilize the octahedral coordination sphere of the palladium(IV) center and thus prevent reductive elimination or other reductive pathways from an octahedral $d^6$ palladium(IV) to a square planar $d^8$ palladium(II).

In certain embodiments, the inventive high-valent palladium fluoride complex is of the formula:

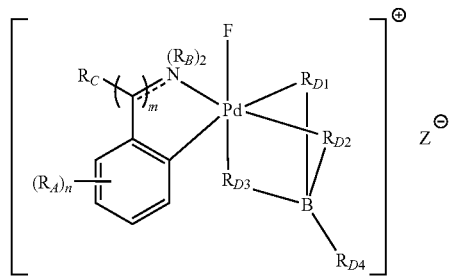

wherein:
the dashed line represents the presence or absence of a bond;
Pd has a valency of +4;
n is an integer between 0 and 4, inclusive;
m is an integer between 0 and 3, inclusive;
each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —SCN; —SW; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to form a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring;

$R_{D1}$, $R_{D2}$, $R_{D3}$, and $R_{D4}$ are each independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl;

$Z^-$ is an anion such as halide, acetate, tosylate, azide, tetrafluoroborate, tetraphenylborate, tetrakis(pentafluorophenyl)borate, $[B[3,5-(CF_3)_2C_6H_3]_4]^-$, hexafluorophosphate, phosphate, sulfate, perchlorate, trifluoromethanesulfonate or hexafluoroantimonate; and F comprises $^{18}F$ or $^{19}F$.

In certain embodiments, the inventive high-valent palladium fluoride complex is of the formula:

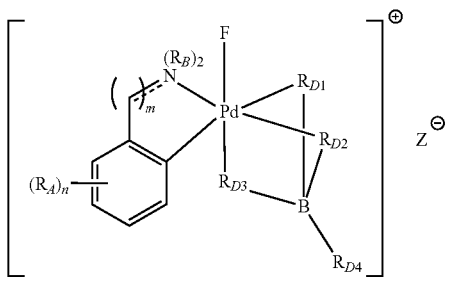

wherein the dashed line represents the presence or absence of a bond;

Pd has a valency of +4;

n is an integer between 0 and 4, inclusive;

m is an integer between 0 and 3, inclusive;

each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to form a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

$R_{D1}$, $R_{D2}$, $R_{D3}$, and $R_{D4}$ are each independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl;

$Z^-$ is an anion such as halide, acetate, tosylate, azide, tetrafluoroborate, tetraphenylborate, tetrakis(pentafluorophenyl)borate, $[B[3,5-(CF_3)_2C_6H_3]_4]^-$, hexafluorophosphate, phosphate, sulfate, perchlorate, trifluoromethanesulfonate or hexafluoroantimonate; and F comprises $^{18}F$ or $^{19}F$.

The counteranion $Z^-$ may be any suitable anion. In certain embodiments, the counteranion has a charge of −1. In certain embodiments, the counteranion has a charge of −2. In certain embodiments, the counteranion has a charge of −3. The counteranion may be an organic or inorganic anion. In certain embodiments, the counteranion is an inorganic anion such as phosphate, hexafluorophosphate, hexafluoroantimonate, sulfate; perchlorate, azide, a halide such as fluoride, chloride, bromide or iodide, etc. In other embodiments, the counteranion is an organic anion such as a carboxylate (e.g., acetate), sulfonate, phosphonate, borate, etc. In certain embodiments, the counteranion is trifluoromethanesulfonate (triflate). In certain embodiments, the counteranion is tosylate. In certain embodiments, the counteranion is mesylate. In certain embodiments, the counteranion is hexafluorophosphate. In certain embodiments, the counteranion is tetraphenylborate. In certain embodiments, the counteranion is tetrafluoroborate. In certain embodiments, the counteranion tetrakis(pentafluorophenyl)borate. In certain embodiments, the counteranion is hexafluoroanimonate. In certain embodiments, the counterion is $[B[3,5-(CF_3)_2C_6H_3]_4]^-$, commonly abbreviated as $[BAr^F_4]^-$.

In certain embodiments, n is 0, in which case the phenyl ring is unsubstituted. In certain embodiments, n is 1. In certain embodiments, n is 2. In certain embodiments, n is 3. In certain embodiments, n is 4. For the case where n is 1 or more, the substituents on the phenyl ring may have any substitution pattern.

In certain embodiments, m is 0. In certain embodiments, m is 1. In certain embodiments, m is 2. In certain embodiments, m is 3.

In certain embodiments, the dashed line represents a bond, thus forming an imine moiety. In other embodiments, the dashed line represents the absence of a bond resulting in only a single bond between the carbon atom and nitrogen atom.

In certain embodiments, at least one $R_A$ is halogen. In certain embodiments, at least one occurrence of $R_A$ is aliphatic. In certain embodiments, at least one occurrence of $R_A$ is $C_1$-$C_6$ alkyl. In certain embodiments, at least one occurrence of $R_A$ is methyl. In certain embodiments, at least one occurrence of $R_A$ is ethyl. In certain embodiments, at least one occurrence of $R_A$ is propyl. In certain embodiments, at least one occurrence of $R_A$ is butyl. In certain embodiments, at least one occurrence of $R_A$ is heteroaliphatic. In certain embodiments, at least one occurrence of $R_A$ is acyl. In certain embodiments, at least one occurrence of $R_A$ is aryl. In certain embodiments, at least one occurrence of $R_A$ is heteroaryl. In certain embodiments, at least one occurrence of $R_A$ is —OR'. In certain embodiments, at least one occurrence of $R_A$ is —N(R')$_2$. In certain embodiments, at least one occurrence of $R_A$ is —SR'. In certain embodiments, at least one occurrence of $R_A$ is —NO$_2$. In certain embodiments, at least one occurrence of $R_A$ is —CN. In certain embodiments, at least one occurrence of $R_A$ is —SCN.

In certain embodiments, two occurrences of $R_A$ taken together form a cyclic moiety. Such a cyclic moeity may be carbocyclic or heterocyclic. In certain embodiments, the cyclic moiety is a substituted or unsubstituted phenyl moiety. In certain embodiments, the cyclic moiety is an unsubstituted phenyl moiety. In certain embodiments, the cyclic moiety is a substituted or unsubstituted heteroaryl moiety.

In certain embodiments, at least one occurrence of $R_B$ is hydrogen. In certain embodiments, both $R_B$ are hydrogen. In certain embodiments, at least one occurrence of $R_B$ is aliphatic. In certain embodiments, both occurrences of $R_B$ are aliphatic. In certain embodiments, both occurrences of $R_B$ are $C_1$-$C_6$ alkyl. In certain embodiments, both occurrences of $R_B$ are methyl. In certain embodiments, both occurrences of $R_B$ are ethyl. In certain embodiments, both occurrences of $R_B$ are propyl. In certain embodiments, both occurrences of $R_B$ are butyl. In certain embodiments, at least one occurrence of $R_B$ is heteroaliphatic. In certain embodiments, both occurrences of $R_B$ are heteroaliphatic. In certain embodiments, at least one occurrence of $R_B$ is acyl. In certain embodiments, at least one occurrence of $R_B$ is aryl. In certain embodiments, at least one occurrence of $R_B$ is heteroaryl.

In certain embodiments, both $R_B$ are the same. In certain embodiments, the two $R_B$ are different.

In certain embodiments, both $R_B$ are taken together to form a heterocyclic moiety. In certain embodiments, both $R_B$ are taken together to form a 5-membered heterocyclic moiety. In certain embodiments, both $R_B$ are taken together to form a 6-membered heterocyclic moiety. In certain embodiments, both $R_B$ are taken together to form an optionally substituted heteroaryl moiety.

In certain embodiments, one $R_B$ moiety is covalently attached to a methylene group connecting the phenyl ring to the N atom, thus forming a heterocyclic moiety. Such a heterocyclic moiety may be a heteroaryl moiety. For example, in certain embodiments, the heterocyclic moiety is a pyridinyl moiety.

In certain embodiments, $R_C$ is hydrogen. In certain embodiments, $R_C$ is aliphatic. In certain embodiments, $R_C$ is $C_1$-$C_6$ alkyl. In certain embodiments, $R_C$ is methyl. In certain embodiments, $R_C$ is ethyl. In certain embodiments, $R_C$ is propyl. In certain embodiments, $R_C$ is butyl. In certain embodiments, $R_C$ is heteroaliphatic. In certain embodiments, $R_C$ is heteroaliphatic. In certain embodiments, $R_C$ is acyl. In certain embodiments, $R_C$ is aryl. In certain embodiments, $R_C$ is heteroaryl. In certain embodiments, one $R_B$ and $R_C$ are taken together to form a heterocyclic moiety. In certain embodiments, one $R_B$ and $R^C$ are taken together to form a 5-membered heterocyclic moiety. In certain embodiments, one $R_B$ and $R_C$ are taken together to form a 6-membered heterocyclic moiety. In certain embodiments, one $R_B$ and $R_C$ are taken together to form an optionally substituted heteroaryl moiety.

In certain embodiments, $R_{D1}$, $R_{D2}$, $R_{D3}$ and $R_{D4}$ all represent optionally substituted heteroaryl moieties. In certain embodiments, at least one of $R_{D1}$, $R_{D2}$, $R_{D3}$ and $R_{D4}$ is an unsubstituted heteroaryl moiety. In certain embodiments, $R_{D1}$, $R_{D2}$, $R_{D3}$ and $R_{D4}$ are all unsubstituted heteroaryl moieties. In certain embodiments, $R_{D1}$, $R_{D2}$, $R_{D3}$ and $R_{D4}$ are all optionally substituted 5-membered heteroaryl moieties. In certain embodiments, $R_{D1}$, $R_{D2}$, $R_{D3}$ and $R_{D4}$ are all nitrogen-containing 5-membered heteroaryl moieties, which are optionally substituted. In certain embodiments, $R_{D1}$, $R_{D2}$, $R_{D3}$ and $R_{D4}$ are all optionally substituted pyrazolyl moieties. In certain embodiments, $R_{D1}$, $R_{D2}$, $R_{D3}$ and $R_{D4}$ are all optionally substituted imidazolyl moieties. In certain embodiments, $R_{D1}$, $R_{D2}$, $R_{D3}$ and $R_{D4}$ are all optionally substituted pyrrolyl moieties. In certain embodiments, $R_{D1}$, $R_{D2}$, $R_{D3}$ and $R_{D4}$ are all are optionally substituted thiazolyl moieties. In certain embodiments, $R_{D1}$, $R_{D2}$, $R_{D3}$ and $R_{D4}$ are all optionally substituted oxazolyl moieties. In certain embodiments, $R_{D1}$, $R_{D2}$, $R_{D3}$ and $R_{D4}$ are all optionally substituted 6-membered heteroaryl moieties. In certain embodiments, $R_{D1}$, $R_{D2}$, $R_{D3}$ and $R_{D4}$ are all nitrogen-containing 6-membered heteroaryl moieties, which are optionally substituted. In certain embodiments, $R_{D1}$, $R_{D2}$, $R_{D3}$ and $R_{D4}$ are all optionally substituted pyridinyl moieties. In certain embodiments, $R_{D1}$, $R_{D2}$, $R_{D3}$ and $R_{D4}$ are all optionally substituted pyrazinyl moieties. In certain embodiments, $R_{D1}$, $R_{D2}$, $R_{D3}$ and $R_{D4}$ are all optionally substituted pyrimidinyl moieties. In certain embodiments, $R_{D1}$, $R_{D2}$, $R_{D3}$ and $R_{D4}$ are all optionally substituted pyridazinyl moieties. In certain embodiments, all of $R_{D1}$, $R_{D2}$, $R_{D3}$ and $R_{D4}$ of the borate ligand are the same. In other embodiments, all of $R_{D1}$, $R_{D2}$, $R_{D3}$ and $R_{D4}$ of the borate ligand are not the same. For example, a combination of heterocycle may constitute the borate ligand. In certain embodiments, a combination of heteroaryl moieties may constitute the borate ligand.

In certain embodiments, the palladium complex comprises a bidentate ligand of one of the formulae:

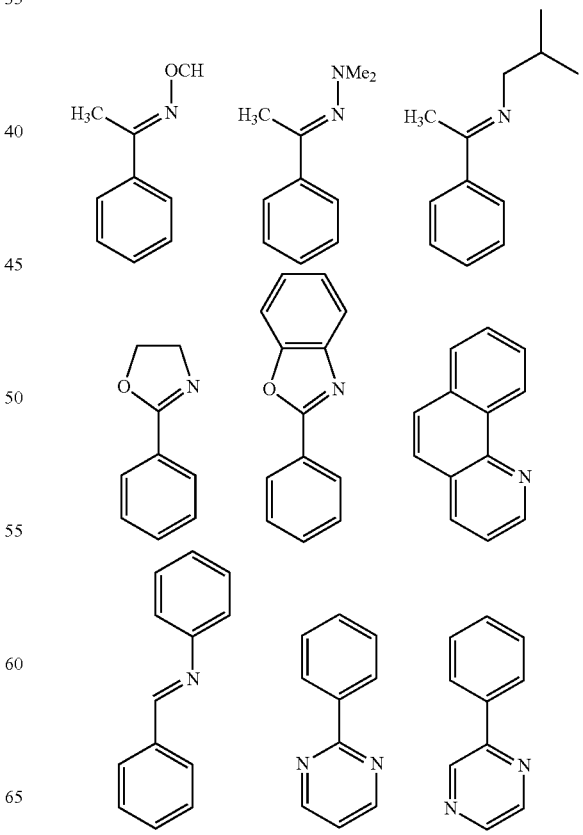

-continued

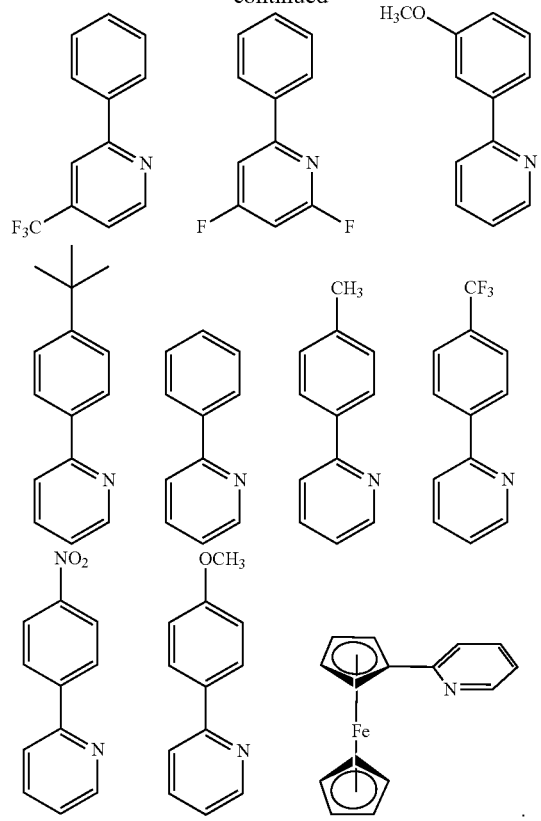

These ligands make a five-membered ring with the palladium atom with the nitrogen and a carbon coordinated to the central palladium.

In certain embodiments, the palladium complex is of the formula:

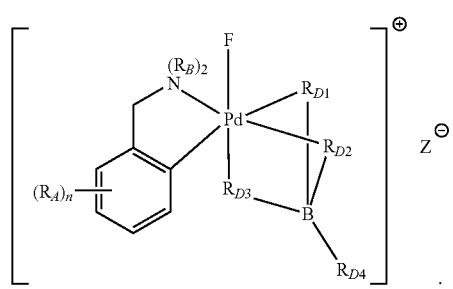

In certain embodiments, the palladium complex is of the formula:

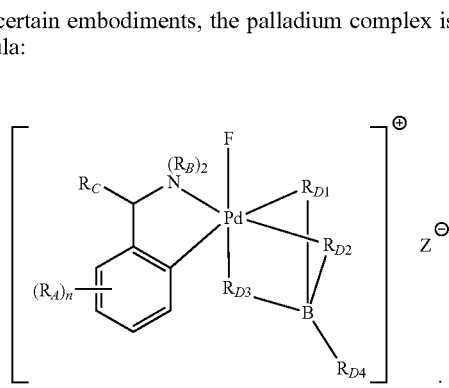

In certain embodiments, the palladium complex is of the formula:

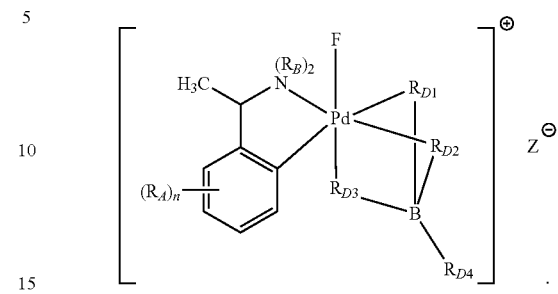

In certain embodiments, the palladium complex is of the formula:

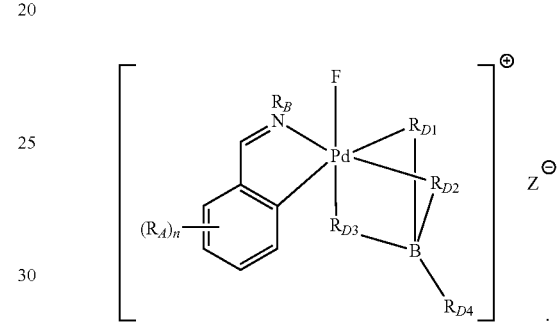

In certain embodiments, the palladium complex is of the formula:

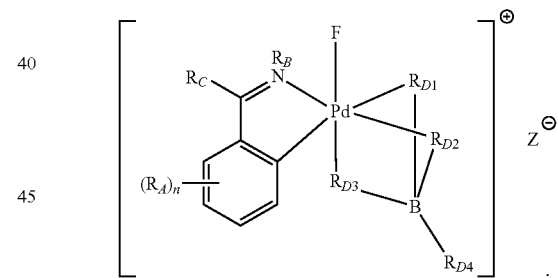

In certain embodiments, the palladium complex is of the formula:

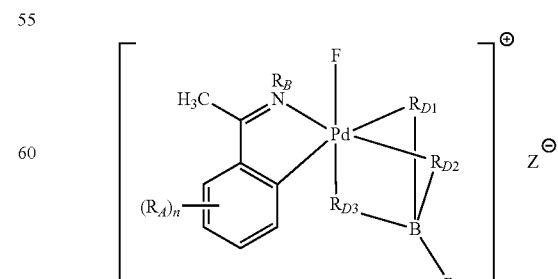

In certain embodiments, the palladium complex is of the formula:

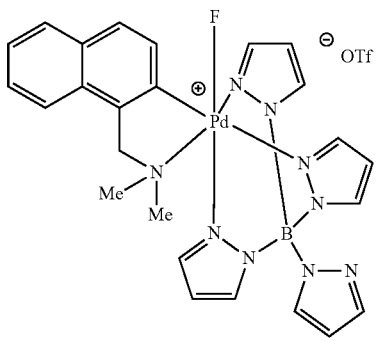

In certain embodiments, the palladium complex is of the formula:

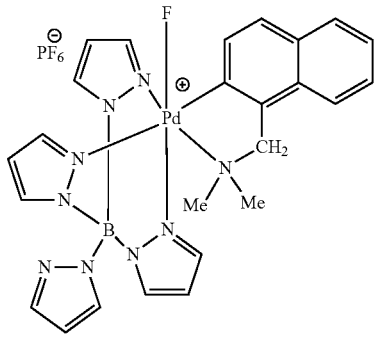

Preparation of High-Valent Palladium Fluoride Complexes

Figure 1:
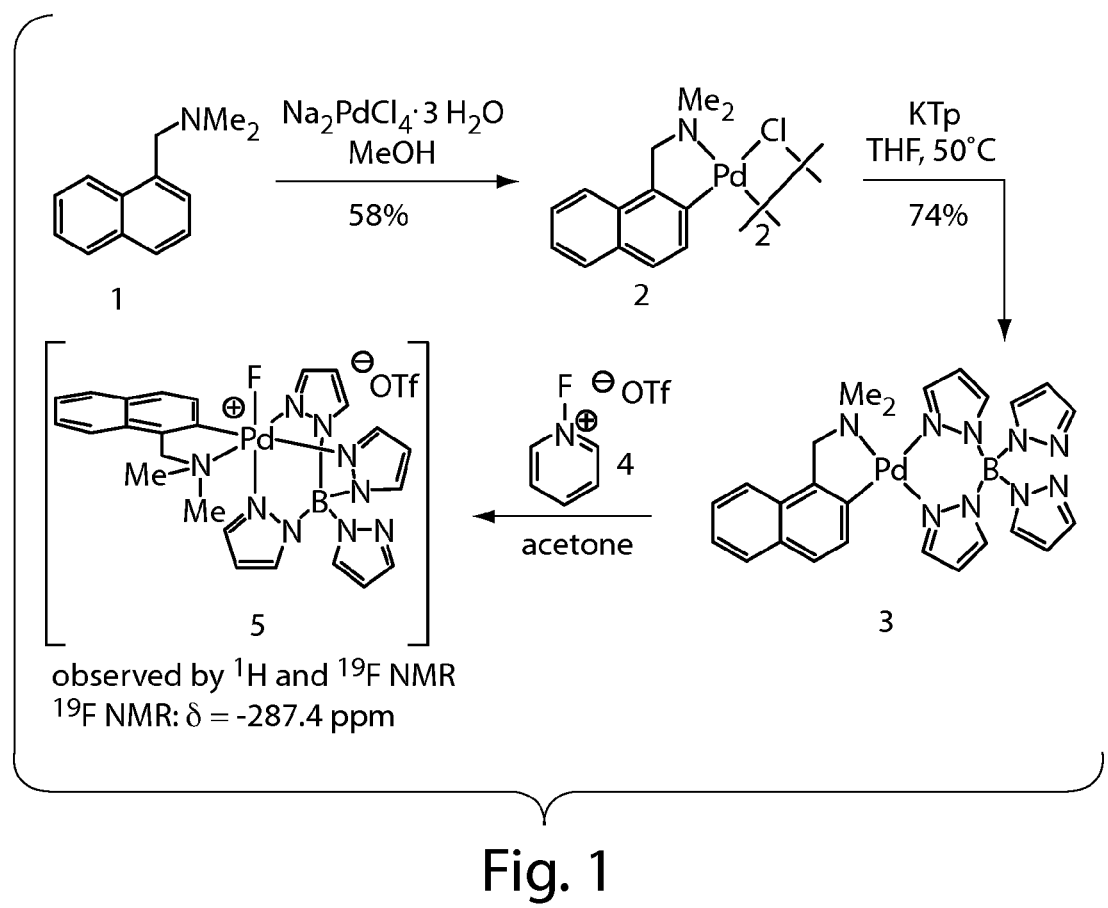
FIG. 1 is an exemplary synthesis of a palladium(IV) fluoride complex.

The inventive palladium complexes are typically prepared starting from disodium tetrachloropalladate. As would be appreciated by one of skill in the art, other palladium salts may also be used to prepare the inventive complexes. The starting material is subjected to cyclometallation to yield a palladium(II) chloride dimer. The chloride ligands are then substituted using the desired borate ligand to yield a palladium(II) borate, which is then oxidized with a fluorine-containing oxidizing reagent (e.g., 1-fluoro-pyridinium triflate, 2,4,6-trimethylpyridinium hexafluorophosphate, etc.) to yield the inventive palladium(IV) complex. An exemplary synthesis of a palladium(IV) fluoride complex is shown in FIG. 1.

In certain embodiments, the method of preparing an inventive palladium(IV) fluoride complex comprises (1) cyclometallating a palladium(II) salt with a bidentate ligand comprising a carbon-based with a carbon donor and a nitrogen donor to yield a palladium(II) chloride dimer; (2) reacting the palladium(II) dimer with a tridentate borate ligand under suitable conditions to yield a palladium(II) borate; and oxidizing the palladium(II) borate with a fluorinating reagent under suitable conditions to yield a palladium(IV) fluoride complex.

In certain embodiments, the bidentate ligand is of the formula:

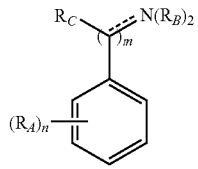

wherein
the dashed line represents the presence or absence of a bond;
n is an integer between 0 and 4, inclusive;
m is an integer between 0 and 3, inclusive;
each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two RA may be taken together to form a substituted or unsubstituted carbocyclic, heterocyclic, aryl or heteroaryl ring; and each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; and each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring.

In certain embodiments, the borate ligand is tetrapyrazolylborate. In certain embodiments, the borate ligand is phenyltris(methimazolyl)borate.

In certain embodiments, an intermediate in the synthesis of a palladium(IV) fluoride complex is of the formula:

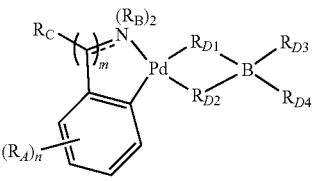

wherein
the dashed line represents the presence or absence of a bond;
Pd has a valency of +2;
n is an integer between 0 and 4, inclusive;
m is an integer between 0 and 3, inclusive;

each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to faun a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring; and $R_{D1}$, $R_{D2}$, $R_{D3}$, and $R_{D4}$ are each independently cyclic or acyclic, substituted or unsubstituted, branched or unbranched aliphatic; cyclic or acyclic, substituted or unsubstituted, branched or unbranched heteroaliphatic; substituted or unsubstituted, branched or unbranched aryl; substituted or unsubstituted, branched or unbranched heteroaryl.

In certain embodiments, n is 0, in which case the phenyl ring is unsubstituted. In certain embodiments, n is 1. In certain embodiments, n is 2. In certain embodiments, n is 3. In certain embodiments, n is 4. For the case where n is 1 or more, the substituents on the phenyl ring may have any substitution pattern.

In certain embodiments, m is 0. In certain embodiments, m is 1. In certain embodiments, m is 2. In certain embodiments, m is 3.

In certain embodiments, the dashed line represents a bond, thus forming an imine moiety. In other embodiments, the dashed line represents the absence of a bond resulting in only a single bond between the carbon atom and nitrogen atom.

In certain embodiments, at least one $R_A$ is halogen. In certain embodiments, at least one occurrence of $R_A$ is aliphatic. In certain embodiments, at least one occurrence of $R_A$ is $C_1$-$C_6$ alkyl. In certain embodiments, at least one occurrence of $R_A$ is methyl. In certain embodiments, at least one occurrence of $R_A$ is ethyl. In certain embodiments, at least one occurrence of $R_A$ is propyl. In certain embodiments, at least one occurrence of $R_A$ is butyl. In certain embodiments, at least one occurrence of $R_A$ is heteroaliphatic. In certain embodiments, at least one occurrence of $R_A$ is acyl. In certain embodiments, at least one occurrence of $R_A$ is aryl. In certain embodiments, at least one occurrence of $R_A$ is heteroaryl. In certain embodiments, at least one occurrence of $R_A$ is —OR'. In certain embodiments, at least one occurrence of $R_A$ is —N(R')$_2$. In certain embodiments, at least one occurrence of $R_A$ is —SR'. In certain embodiments, at least one occurrence of $R_A$ is —NO$_2$. In certain embodiments, at least one occurrence of $R_A$ is —CN. In certain embodiments, at least one occurrence of $R_A$ is —SCN.

In certain embodiments, two occurrences of $R_A$ taken together form a cyclic moiety. Such a cyclic moeity may be carbocyclic or heterocyclic. In certain embodiments, the cyclic moiety is a substituted or unsubstituted phenyl moiety. In certain embodiments, the cyclic moiety is an unsubstituted phenyl moiety. In certain embodiments, the cyclic moiety is a substituted or unsubstituted heteroaryl moiety.

In certain embodiments, at least one occurrence of $R_B$ is hydrogen. In certain embodiments, both $R_B$ are hydrogen. In certain embodiments, at least one occurrence of $R_B$ is aliphatic. In certain embodiments, both occurrences of $R_B$ are aliphatic. In certain embodiments, both occurrences of $R_B$ are $C_1$-$C_6$ alkyl. In certain embodiments, both occurrences of $R_B$ are methyl. In certain embodiments, both occurrences of $R_B$ are ethyl. In certain embodiments, both occurrences of $R_B$ are propyl. In certain embodiments, both occurrences of $R_B$ are butyl. In certain embodiments, at least one occurrence of $R_B$ is heteroaliphatic. In certain embodiments, both occurrences of $R_B$ are heteroaliphatic. In certain embodiments, at least one occurrence of $R_B$ is acyl. In certain embodiments, at least one occurrence of $R_B$ is aryl. In certain embodiments, at least one occurrence of $R_B$ is heteroaryl.

In certain embodiments, both $R_B$ are the same. In certain embodiments, the two $R_B$ are different.

In certain embodiments, both $R_B$ are taken together to form a heterocyclic moiety. In certain embodiments, both $R_B$ are taken together to form a 5-membered heterocyclic moiety. In certain embodiments, both $R_B$ are taken together to form a 6-membered heterocyclic moiety. In certain embodiments, both $R_B$ are taken together to form an optionally substituted heteroaryl moiety.

In certain embodiments, one $R_B$ moiety is covalently attached to a methylene group connecting the phenyl ring to the N atom, thus forming a heterocyclic moiety. Such a heterocyclic moiety may be a heteroaryl moiety. For example, in certain embodiments, the heterocyclic moiety is a pyridinyl moiety.

In certain embodiments, $R_{D1}$, $R_{D2}$, $R_{D3}$ and $R_{D4}$ all represent optionally substituted heteroaryl moieties. In certain embodiments, at least one of $R_{D1}$, $R_{D2}$, $R_{D3}$ and $R_{D4}$ is an unsubstituted heteroaryl moiety. In certain embodiments, $R_{D1}$, $R_{D2}$, $R_{D3}$ and $R_{D4}$ are all unsubstituted heteroaryl moieties. In certain embodiments, $R_{D1}$, $R_{D2}$, $R_{D3}$ and $R_{D4}$ are all optionally substituted 5-membered heteroaryl moieties. In certain embodiments, $R_{D1}$, $R_{D2}$, $R_{D3}$ and $R_{D4}$ are all nitrogen-containing 5-membered heteroaryl moieties, which are optionally substituted. In certain embodiments, $R_{D1}$, $R_{D2}$, $R_{D3}$ and $R_{D4}$ are all optionally substituted pyrazolyl moieties. In certain embodiments, $R_{D1}$, $R_{D2}$, $R_{D3}$ and $R_{D4}$ are all optionally substituted imidazolyl moieties. In certain embodiments, $R_{D1}$, $R_{D2}$, $R_{D3}$ and $R_{D4}$ are all optionally substituted pyrrolyl moieties. In certain embodiments, $R_{D1}$, $R_{D2}$, $R_{D3}$ and $R_{D4}$ are all are optionally, substituted thiazolyl moieties. In certain embodiments, $R_{D1}$, $R_{D2}$, $R_{D3}$ and $R_{D4}$ are all optionally substituted oxazolyl moieties. In certain embodiments, $R_{D1}$, $R_{D2}$, $R_{D3}$ and $R_{D4}$ are all optionally substituted 6-membered heteroaryl moieties. In certain embodiments, $R_{D1}$, $R_{D2}$, $R_{D3}$ and $R_{D4}$ are all nitrogen-containing 6-membered heteroaryl moieties, which are optionally substituted. In certain embodiments, $R_{D1}$, $R_{D2}$, $R_{D3}$ and $R_{D4}$ are all optionally substituted pyridinyl moieties. In certain embodiments, $R_{D1}$, $R_{D2}$, $R_{D3}$ and $R_{D4}$ are all optionally substituted pyrazinyl moieties. In certain embodiments, $R_{D1}$, $R_{D2}$, $R_{D3}$ and $R_{D4}$ are all optionally substituted pyrimidinyl moieties. In certain embodiments, $R_{D1}$, $R_{D2}$, $R_{D3}$ and $R_{D4}$ are all optionally substituted pyridazinyl moieties. In certain embodiments, all of $R_{D1}$, $R_{D2}$, $R_{D3}$ and $R_{D4}$ of the borate ligand are the same. In other embodiments, all of $R_{D1}$, $R_{D2}$, $R_{D3}$ and $R_{D4}$ of the borate ligand are not the same. For example, a combination of heterocycle may constitute the borate ligand. In certain embodiments, a combination of heteroaryl moieties may constitute the borate ligand.

In certain embodiments, the intermediate comprises a bidentate ligand of one of the formulae:

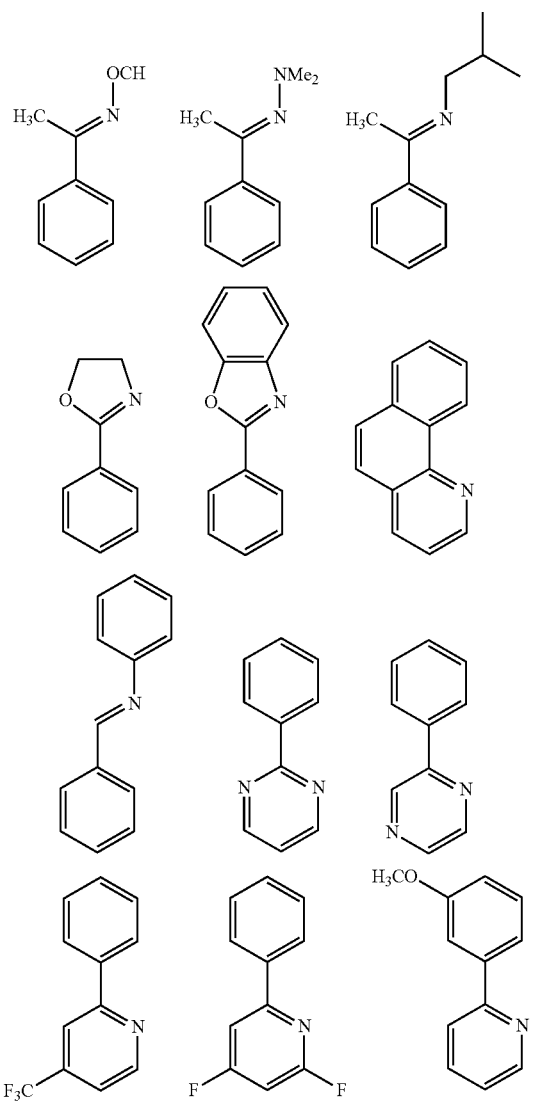

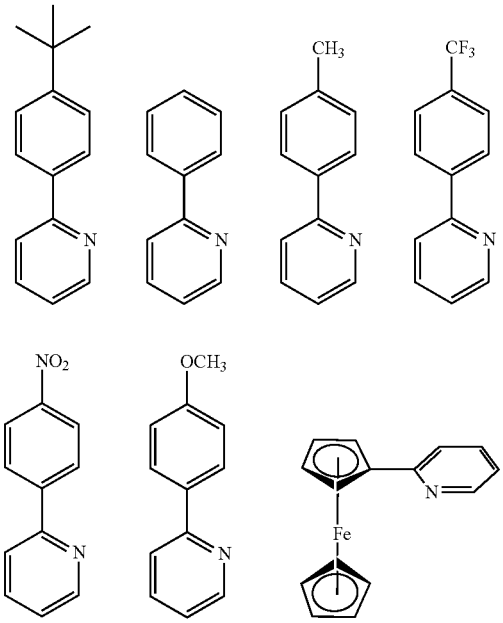

These ligands make a five-membered ring with the palladium atom with the nitrogen and a carbon coordinated to the central palladium.

In certain embodiments, the intermediate is of the formula:

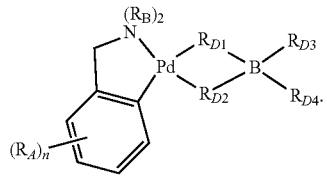

In certain embodiments, the intermediate is of the formula:

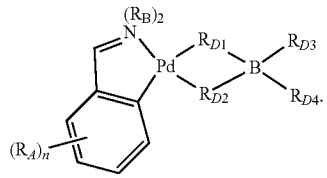

In certain embodiments, the intermediate is of the formula:

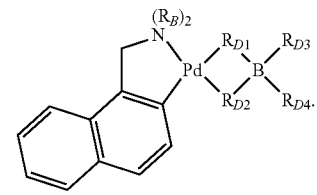

In certain embodiments, the intermediate is of the formula:

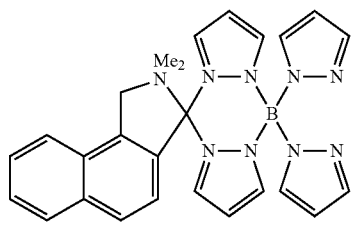

Fluorinating Agents

As generally described above, the process for preparing the high-valent palladium(IV) fluoride complexes utilizes a fluorinating agent. In certain embodiments, the fluorinating agent is an electrophilic fluorinating agent. In certain embodiments, the fluorinating agent is commercially available. In certain embodiments, the electrophilic fluorinating agent is an inorganic fluorinating agent. Exemplary electrophilic fluorinating agents include, but are not limited to, N-fluoropyridinium triflate, N-fluoro-2,4,6-trimethylpyridinium triflate, N-fluoro-2,4,6-trimethylpyridinium tetrafluoroborate, N-fluoro-2,6-dichloropyridinium tetrafluoroborate, N-fluoro-2,6-dichloropyridinium triflate, N-fluoropyridinium pyridine heptafluorodiborate, N-fluoropyridinium tetrafluoroborate, N-fluoropyridinium triflate, fluoroarylsulfonimide (e.g., N-fluorobenzenesulfonimide), N-chloromethyl-N'-fluorotriethylenediammonium bis(tetrafluoroborate) (Selectfluor®), and $XeF_2$. In certain embodiments, the fluorinating agent is Selectfluor®. In certain embodiments, the fluorinating agent is N-fluoropyridinium triflate. In certain embodiments, the fluorinating agent is N-fluoro-2,4,6-trimethylpyridinium triflate. In certain embodiments, the fluorinating agent is N-fluoro-2,4,6-trimethylpyridinium tetrafluoroborate. In certain embodiments, the fluorinating agent is N-fluoro-benzenesulfonimide. In certain embodiments, the fluorinating agent is xenon difluoride. In certain embodiments, the fluorinating agent is N-chloromethyl-N'-fluorotriethylenediammonium bis(tetrafluoroborate) (Selectfluor®).

The fluorinating agent may be enriched with a particular isoptope of fluorine. In certain embodiments, the fluorinating agent is labeled with $^{19}F$ (i.e., transfers an $^{19}F$ fluorine substituent to the organic compound). In certain embodiments, reaction of the $^{19}F$ fluorinating agent in the inventive process provides a fluorinated $^{19}F$-labeled organic compound.

In certain embodiments, the fluorinating agent is labeled with $^{18}F$ (i.e., transfers an $^{18}F$ fluorine substituent to the organic compound). In certain embodiments, reaction of the $^{18}F$ fluorinating agent in the inventive process provides a fluorinated $^{18}F$-labeled organic compound.

However, in certain embodiments, the fluorinating agent is labeled with a mixture of $^{18}F$ and $^{19}F$. In certain embodiments, reaction of the fluorinating agent with a mixture of $^{19}F$ and $^{18}F$ in the inventive process provides a mixture of fluorinated $^{19}F$-labeled organic compound and fluorinated $^{18}F$-labeled organic compound. In certain embodiments, the portion of each of $^{19}F$ and $^{18}F$ in the mixture is known. Any of the above fluorinated agents may be labeled with $^{19}F$ or $^{18}F$.

For example, in certain embodiments, the fluorinating agent is $^{19}F$-labeled N-chloromethyl-N'-fluorotriethylenediammonium bis(tetrafluoroborate) (Selectfluor®) or $^{19}F$-labeled $XeF_2$. In certain embodiments, the fluorinating agent is $^{19}F$-labeled N-chloromethyl-N'-fluorotriethylenediammonium bis(tetrafluoroborate) (Selectfluor®). In certain embodiments, the fluorinating agent is $^{19}F$-labeled $XeF_2$.

In certain embodiments, the fluorinating agent is $^{18}F$-labeled $XeF_2$.

The inventive high-valent palladium(IV) fluoride complexes may also be prepared using nucleophilic fluoride rather than electrophilic fluorinating reagent. In general, this may be accomplished by first preparing the analogous high-valent palladium(IV) chloride (or other halogen) complex and subjecting the complex to halogen metathesis using AgF as shown in the scheme below.

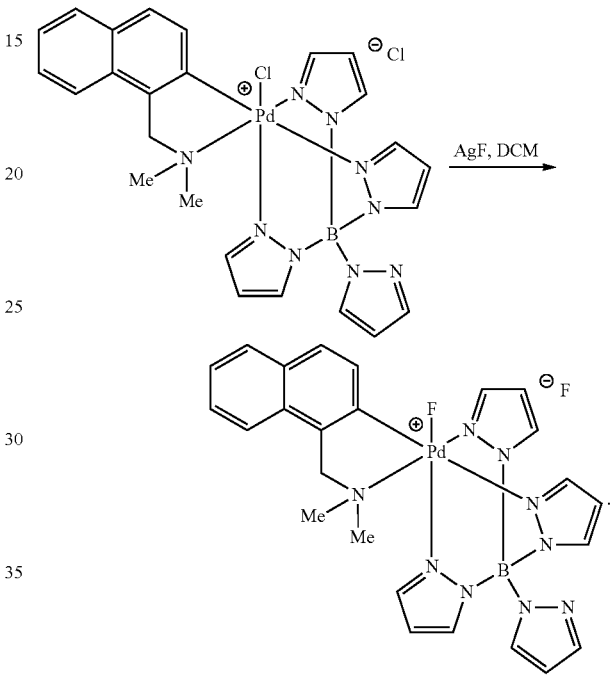

Oxidation of the palladium(II) intermediate with $PhICl_2$ affords the Pd (IV) chloride complex. Reaction of the Pd (IV) chloride complex with AgF under suitable conditions then yields the Pd (IV) fluoride complex.

Uses

The inventive high-valent palladium(IV) fluoride complexes possess an electrophilic fluoride and thus are reactive toward nucleophiles such as palladium(II) complexes (e.g., palladium(II) aryl complexes), $PPh_3$, enamines, and enol silyl ethers. Although electrophilic fluorinating reagents including acetyl hypofluorites, xenon difluoride, and nitrogen fluorides are commercially available, they are expensive and tend to be poorly regioselective. The inventive complexes may also be useful in fluorination reactions by providing electrophilic $F^+$. In particular, the high valent palladium complexes may be useful in conjunction with other transition metal reagents or catalysts for transferring the electrophilic F to an organic compound.

In certain embodiments, the inventive high-valent palladium fluoride complexes described herein are used in conjunction with the palladium(II)-mediated fluorination reactions described in U.S. provisional patent application, U.S. Ser. No. 61/063,096, filed Jan. 31, 2008, and U.S. Ser. No. 61/050,446, filed May 5, 2008. Such reactions are particularly useful in preparing aryl fluorides.

In certain embodiments, the inventive high-valent palladium fluoride complexes are reacted with enol silyl ethers under suitable conditions to yield alpha-fluorinated carbonyl compounds. In certain embodiments, the starting material is cyclohexanone enol trimethylsilyl ether. In certain embodiments, the inventive high-valent palladium fluoride complexes are reacted with enamines under suitable conditions to yield fluorinated compounds.

Organic Compounds

As generally described above, the invention provides a process for fluorinating an organic or organometallic compound using a high-valent palladium(IV) fluoride complex. In certain embodiments, the organic or organometallic compound has a particular substituent that is replaced with the fluoride from the complex.

The organic compound utilized in the inventive process includes, but is not limited to, small organic molecules and/or large organic molecules. A small organic molecule include any molecule having a molecular weight of less than 1000 g/mol, of less than 900 g/mol, of less than 800 g/mol, of less than 700 g/mol, of less than 600 g/mol, of less than 500 g/mol, of less than 400 g/mol, of less than 300 g/mol, of less than 200 g/mol or of less than 100 g/mol. A large organic molecule include any molecule of between 1000 g/mol to 5000 g/mol, of between 1000 g/mol to 4000 g/mol, of between 1000 g/mol to 3000 g/mol, of between 1000 g/mol to 2000 g/mol, or of between 1000 g/mol to 1500 g/mol. Organic compounds include, but are not limited to, aryl compounds, heteroaryl compounds, carbocyclic compounds, heterocyclic compounds, aliphatic compounds, heteroaliphatic compounds, as well as polymers, peptides, glycopeptides, and the like.

In certain embodiments, the organic compound is an optionally substituted aliphatic, optionally substituted heteroaliphatic, optionally substituted aryl, or optionally substituted heteroaryl compound. In certain embodiments, the organic compound is an aryl-containing compound.

In certain embodiments, an organic compound is a polymer.

In certain embodiments, an organic compound is a peptide.

In certain embodiments, an organic compound is biologically active.

For example, in certain embodiments, the organic compound is an agrochemical. In certain embodiments, the organic compound is an insecticide or a pheromone of insect origin.

In certain embodiments, the organic compound is pharmaceutical agent. For example, in certain embodiments, the pharmaceutical agent is an anti-emetic, anti-coagulant, anti-platelet, anti-arrhythmic, anti-herpertensive, anti-anginal, a lipid-modifying drug, sex hormone, anti-diabetic, antibiotic, anti-viral, anti-fungal, anti-cancer, immunostimulant, immunosuppressant, anti-inflammatory, anti-rheumatic, anesthetic, analgesic, anticonvulsant, hypnotic, anxiolytic, antipsychotic, barbituate, antidepressant, sedative, anti-obesity, antihistime, anti-eleptic, anti-manic, opioid, anti-Parkinson, anti-Alzheimers, anti-dementia, an anti-substance dependance drug, cannabinoid, 5HT-3 antagonist, monoamine oxidase inhibitor (MAOI), selective serotonin reuptake inhibitor (SSRI), or stimulant. In certain embodiments, the pharmaceutical agent is a psychotropic agent. In certain embodiments, the pharmaceutical agent is any pharmaceutical agent approved by the United States Food and Drug Administration (FDA) for administration to a human (see, e.g., www.accessdata.fda.gov/scripts/cder/drugsatfda).

In certain embodiments, the pharmaceutical agent is an antibiotic. In certain embodiments, the pharmaceutical agent is a lipid modifying drug. In certain embodiments, the pharmaceutical agent is a CNS drug (i.e., drug acting on the Central Nervous System). CNS drugs include, but are not limited to, hypnotics, anxiolytics, antipsychotics, barbituates, antidepressants, antiobesity, antihistimes, antilepetics, antimanics, opioids, analgesics, anti-Parkinson, anti-Alzheimers, anti-dementia, anti-substance dependance drugs, cannabinoids, 5HT-3 antagonists, monoamine oxidase inhibitors (MAOIs), selective serotonin reuptake inhibitors (SSRIs) and stimulants. Exemplary antibiotics, lipid modifying drugs and CNS drugs are provided below in Table 1.

TABLE 1

| TYPE | CLASS | TRADE NAME |
|---|---|---|
| Antibiotic | Beta-lactam | AMOXICILLIN |
| Antibiotic | aminoglycoside | AMIKACIN |
| Antibiotic | Beta-lactam | AMPICILLIN |
| Antibiotic | Beta-lactam | AZTREONAM |
| Antibiotic | Carboxypenicillin | CARBENICILLIN |
| Antibiotic | $2^{nd}$ generation cephalosporin | CEFACLOR |
| Antibiotic | cephalosporin | CEFAMANDOLE |
| Antibiotic | cephalosporin | CEFAZOLIN |
| Antibiotic | cephalosporin | CEFEPIME |
| Antibiotic | $3^{rd}$ generation cephalosporin | CEFIXIME |
| Antibiotic | cephamycin | CEFMETAZOLE |
| Antibiotic | $2^{nd}$ generation cephalosporin | CEFONICID |
| Antibiotic | $3^{rd}$ generation cephalosporin | CEFOPERAZONE |
| Antibiotic | $3^{rd}$ generation cephalosporin | CEFOTAXIME |
| Antibiotic | $2^{nd}$ generation cephalosporin | CEFOXITIN |
| Antibiotic | $3^{rd}$ generation cephalosporin | CEFTAZIDIME |
| Antibiotic | cephalosporin | CEFTIZOXIME |
| Antibiotic | $3^{rd}$ generation cephalosporin | CEFTRIAXONE |
| Antibiotic | $2^{nd}$ generation cephalosporin | CEFUROXIME |
| Antibiotic | cephalosporin | CEPHALOTHIN |
| Antibiotic | fluoroquinolone | CIPROFLOXACIN |
| Antibiotic | lincosamide | CLINDAMYCIN |
| Antibiotic | cephalosporin | CEFOTETAN |
| Antibiotic | macrolide | ERYTHROMYCIN |
| Antibiotic | aminoglycoside | GENTAMICIN |
| Antibiotic | Beta-lactam | IMIPENEM |
| Antibiotic | aminoglycoside | KANAMYCIN |
| Antibiotic | Beta-lactam | MEROPENEM |
| Antibiotic | beta-lactam | METHICILLIN |
| Antibiotic | nitroimidazole | METRONIDAZOLE |
| Antibiotic | beta-lactam | NAFCILLIN |
| Antibiotic | quinolone | NALIDIXIC ACID |
| Antibiotic | aminoglycoside | NETILMICIN |
| Antibiotic | | NITROFURANTOIN |
| Antibiotic | fluoroquinolone | NORFLOXACIN |
| Antibiotic | fluoroquinolone | OFLOXACIN |
| Antibiotic | beta-lactam | OXACILLIN |
| Antibiotic | beta-lactam | PIPERACILLIN |
| Antibiotic | rifamycin | RIFAMPIN |
| Antibiotic | sulfa drug | SULFISOXAZOLE |
| Antibiotic | glycopeptide | TRIMETHOPRIM |
| Antibiotic | glycopeptide | TEICOPLANIN |
| Antibiotic | carboxypenicillin | TICARCILLIN |
| Antibiotic | glycopeptide | TEICOPLANIN |
| Antibiotic | tetracyclines | TETRACYCLINE |
| Antibiotic | carboxypenicillin | TICARCILLIN |
| Antibiotic | aminoglycoside | TOBRAMYCIN |
| Antibiotic | glycopeptide | VANCOMYCIN |
| Lipid modifying | Statins | ATORVASTATIN (LIPITOR) |
| Lipid modifying | Statins | CERIVASTATIN (LIPOBAY) |
| Lipid modifying | Statins | FLUVASTATIN (LESCOL) |
| Lipid modifying | Statins | LOVASTATIN (STATOSAN) |
| Lipid modifying | Statins | PITAVASTATIN |

TABLE 1-continued

| TYPE | CLASS | TRADE NAME |
|---|---|---|
| Lipid modifying | Statins | PRAVASTATIN (PRAVACHOL) |
| Lipid modifying | Statins | ROSUVASTATIN (CRESTOR) |
| Lipid modifying | Statins | SIMVASTATIN (ZOCOR) |
| Lipid modifying | Fibrates | CLOFIBRATE |
| Lipid modifying | Fibrates | GEMFIBROZIL (LOPID) |
| Lipid modifying | Fibrates | FENOFIBRATE (TRICORE) |
| Lipid modifying | Fibrates | SIMFIBRATE |
| Lipid modifying | Fibrates | RONIFIBRATE |
| Lipid modifying | Fibrates | CIPROFIBRATE |
| Lipid modifying | Fibrates | CLOFIBRIDE |
| Lipid modifying | Bile acid sequestrants | COLESTYRAMINE (QUESTRAN) |
| Lipid modifying | Bile acid sequestrants | COLESTIPOL |
| Lipid modifying | Bile acid sequestrants | COLEXTRAN |
| Lipid modifying | Bile acid sequestrants | COLESEVELAM |
| Lipid modifying | Niacin | NIACIN |
| Lipid modifying | Niacin derivative | NICOFURANOSE |
| Lipid modifying | Other | DEXTROTHYROXINE |
| Lipid modifying | Other | PROBUCOL |
| Lipid modifying | Other | TIADENOL |
| Lipid modifying | Other | BENFLUOREX |
| Lipid modifying | Other | MEGLUTOL |
| Lipid modifying | Other | MAGNESIUM PYRIDOXAL 5-PHOSPHATE GLUTAMATE |
| Lipid modifying | Other | EZETIMIBE (ZETIA) |
| CNS | Hypnotics | NITRAZEPAM |
| CNS | Hypnotics | NITRAZEPAM |
| CNS | Hypnotics | FLUNITRAZEPAM |
| CNS | Hypnotics | FLURAZEPAM |
| CNS | Hypnotics | LOPRAZOLAM |
| CNS | Hypnotics | TEMAZEPAM |
| CNS | Hypnotics | ZALEPLON |
| CNS | Hypnotics | ZOLPIDEM TARTRATE |
| CNS | Hypnotics | ZOPICLONE |
| CNS | Hypnotics | CHLORAL HYDRATE |
| CNS | Hypnotics | CLOMETHIAZOLE |
| CNS | Hypnotics | PROMETHAZINE HYDROCHLORIDE |
| CNS | Anxiolytics | DIAZEPAM |
| CNS | Anxiolytics | ALPRAZOLAM |
| CNS | Anxiolytics | CHLORDIAZEPOXIDE |
| CNS | Anxiolytics | CLORAZEPATE DIPOTASSIUM |
| CNS | Anxiolytics | LORAZEPAM |
| CNS | Anxiolytics | OXAZEPAM |
| CNS | Anxiolytics | BUSPIRONE HYDROCHLORIDE |
| CNS | Anxiolytics | MEPROBAMATE |
| CNS | Anxiolytics | BETA-BLOCKERS |
| CNS | Barbiturates | BARBITURATES |
| CNS | Barbiturates | BARBITURATES |
| CNS | Barbiturates | BARBITURATES |
| CNS | Antipsychotic drugs | BENPERIDOL |
| CNS | Antipsychotic drugs | CHLORPROMAZINE HYDROCHLORIDE |
| CNS | Antipsychotic drugs | FLUPENTIXOL |
| CNS | Antipsychotic drugs | FLUPHENAZINE HYDROCHLORIDE |
| CNS | Antipsychotic drugs | FLUPHENAZINE HYDROCHLORIDE |
| CNS | Antipsychotic drugs | HALOPERIDOL |
| CNS | Antipsychotic drugs | LEVOMEPROMAZINE/ METHOTRIMEPRAZINE |
| CNS | Antipsychotic drugs | LOXAPINE |
| CNS | Antipsychotic drugs | OXYPERTINE |
| CNS | Antipsychotic drugs | PERICYAZINE |
| CNS | Antipsychotic drugs | PERPHENAZINE |
| CNS | Antipsychotic drugs | PIMOZIDE |
| CNS | Antipsychotic drugs | PROCHLORPERAZINE |
| CNS | Antipsychotic drugs | PROMAZINE HYDROCHLORIDE |
| CNS | Antipsychotic drugs | SULPIRIDE |
| CNS | Antipsychotic drugs | THIORIDAZINE |
| CNS | Antipsychotic drugs | TRIFLUOPERAZINE |
| CNS | Antipsychotic drugs | ZUCLOPENTHIXOL ACETATE |
| CNS | Antipsychotic drugs | ZUCLOPENTHIXOL DIHYDROCHLORIDE |
| CNS | Atypical antipsychotics | AMISULPRIDE |
| CNS | Atypical antipsychotics | CLOZAPINE |
| CNS | Atypical antipsychotics | OLANZAPINE |
| CNS | Atypical antipsychotics | QUETIAPINE |
| CNS | Atypical antipsychotics | RISPERIDONE |
| CNS | Atypical antipsychotics | ZOTEPINE |
| CNS | Antipsychotic | FLUPENTIXOL DECANOATE |
| CNS | Antipsychotic | HALOPERIDOL DECANOATE |
| CNS | Antipsychotic | PIPOTIAZINE PALMITATE |
| CNS | Antipsychotic | ZUCLOPENTHIXOL DECANOATE |
| CNS | Antipsychotic | ZUCLOPENTHIXOL DECANOATE |
| CNS | Antipsychotic | ZYPREXA |
| CNS | Antimanic drugs | BENZODIAZEPINES |
| CNS | Antimanic drugs | ANTIPSYCHOTIC DRUGS |
| CNS | Antimanic drugs | CARBAMAZEPINE |
| CNS | Antimanic drugs | VALPROIC ACID |
| CNS | Tricyclic antidepressant drugs | AMITRIPTYLINE HYDROCHLORIDE |
| CNS | Tricyclic antidepressant drugs | AMOXAPINE |
| CNS | Tricyclic antidepressant drugs | CLOMIPRAMINE HYDROCHLORIDE |
| CNS | Tricyclic antidepressant drugs | DOSULEPIN HYDROCHLORIDE/ DOTHIEPIN HYDROCHLORIDE |
| CNS | Tricyclic antidepressant drugs | DOXEPIN |
| CNS | Tricyclic antidepressant drugs | IMIPRAMINE HYDROCHLORIDE |
| CNS | Tricyclic antidepressant drugs | IMIPRAMINE HYDROCHLORIDE |
| CNS | Tricyclic antidepressant drugs | LOFEPRAMINE |
| CNS | Tricyclic antidepressant drugs | NORTRIPTYLINE |
| CNS | Tricyclic antidepressant drugs | TRIMIPRAMINE |
| CNS | Related antidepressant | MAPROTILINE HYDROCHLORIDE |
| CNS | Related antidepressant | MIANSERIN HYDROCHLORIDE |
| CNS | Related antidepressant | TRAZODONE HYDROCHLORIDE |
| CNS | Related antidepressant | TRAZODONE HYDROCHLORIDE |
| CNS | Antidepressant | ESCITALOPRAM OXALATE (LEXPRO) |
| CNS | Monoamine-oxidase inhibitors (MAOIs) | PHENELZINE |
| CNS | Monoamine-oxidase inhibitors (MAOIs) | ISOCARBOXAZID |
| CNS | Monoamine-oxidase inhibitors (MAOIs) | TRANYLCYPROMINE |

TABLE 1-continued

| TYPE | CLASS | TRADE NAME |
|---|---|---|
| CNS | Reversible MAOIs | MOCLOBEMIDE |
| CNS | Selective serotonin re-uptake inhibitors | CITALOPRAM |
| CNS | Selective serotonin re-uptake inhibitors | FLUOXETINE |
| CNS | Selective serotonin re-uptake inhibitors | FLUVOXAMINE MALEATE |
| CNS | Selective serotonin re-uptake inhibitors | PAROXETINE (Paxil) |
| CNS | Selective serotonin re-uptake inhibitors | SERTRALINE |
| CNS | Other antidepressant drugs | FLUPENTIXOL |
| CNS | Other antidepressant drugs | MIRTAZAPINE |
| CNS | Other antidepressant drugs | NEFAZODONE HYDROCHLORIDE |
| CNS | Other antidepressant drugs | REBOXETINE |
| CNS | Other antidepressant drugs | TRYPTOPHAN (L-Tryptophan) |
| CNS | Other antidepressant drugs | VENLAFAXINE |
| CNS | Central nervous system stimulants | DEXAMFETAMINE SULPHATE |
| CNS | Central nervous system stimulants | METHYLPHENIDATE HYDROCHLORIDE |
| CNS | Central nervous system stimulants | METHYLPHENIDATE HYDROCHLORIDE |
| CNS | Central nervous system stimulants | MODAFINIL |
| CNS | Anti-obesity drugs acting on the gastro-intestinal tract | ORLISTAT |
| CNS | Anti-obesity drugs (Centrally acting appetite suppressants) | SIBUTRAMINE HYDROCHLORIDE |
| CNS | Antihistamines | CINNARIZINE |
| CNS | Antihistamines | CYCLIZINE |
| CNS | Antihistamines | MECLOZINE HYDROCHLORIDE |
| CNS | Antihistamines | PROMETHAZINE HYDROCHLORIDE |
| CNS | Antihistamines | PROMETHAZINE TEOCLATE |
| CNS | Phenothiazines and related drugs | CHLORPROMAZINE HYDROCHLORIDE |
| CNS | Phenothiazines and related drugs | PERPHENAZINE |
| CNS | Phenothiazines and related drugs | PROCHLORPERAZINE |
| CNS | Phenothiazines and related drugs | TRIFLUOPERAZINE |
| CNS | Domperidone and metoclopramide | DOMPERIDONE |
| CNS | Domperidone and metoclopramide | METOCLOPRAMIDE HYDROCHLORIDE |
| CNS | Domperidone and metoclopramide | METOCLOPRAMIDE HYDROCHLORIDE |
| CNS | 5HT3 antagonists | GRANISETRON |
| CNS | 5HT3 antagonists | ONDANSETRON |
| CNS | 5HT3 antagonists | TROPISETRON |
| CNS | Cannabinoid | NABILONE |
| CNS | Non-opioid analgesics | ASPIRIN (Acetylsalicylic Acid) |
| CNS | Non-opioid analgesics | PARACETAMOL (Acetaminophen) |
| CNS | Opioid analgesics | MORPHINE |
| CNS | Opioid analgesics | BUPRENORPHINE |
| CNS | Opioid analgesics | CODEINE PHOSPHATE |
| CNS | Opioid analgesics | DEXTROMORAMIDE |
| CNS | Opioid analgesics | DEXTROPROPOXYPHENE HYDROCHLORIDE |
| CNS | Opioid analgesics | DIAMORPHINE HYDROCHLORIDE (Heroin Hydrochloride) |
| CNS | Opioid analgesics | DIHYDROCODEINE TARTRATE |
| CNS | Opioid analgesics | DIPIPANONE HYDROCHLORIDE |
| CNS | Opioid analgesics | FENTANYL |
| CNS | Opioid analgesics | HYDROMORPHONE HYDROCHLORIDE |
| CNS | Opioid analgesics | MEPTAZINOL |
| CNS | Opioid analgesics | METHADONE HYDROCHLORIDE |
| CNS | Opioid analgesics | NALBUPHINE HYDROCHLORIDE |
| CNS | Opioid analgesics | OXYCODONE HYDROCHLORIDE |
| CNS | Opioid analgesics | PENTAZOCINE |
| CNS | Opioid analgesics | PETHIDINE HYDROCHLORIDE |
| CNS | Opioid analgesics | PETHIDINE HYDROCHLORIDE |
| CNS | Opioid analgesics | PHENAZOCINE HYDROBROMIDE |
| CNS | Opioid analgesics | TRAMADOL HYDROCHLORIDE |
| CNS | Neuropathic pain | DEXTROPROPOXYPHENE |
| CNS | Neuropathic pain | METHADONE |
| CNS | Neuropathic pain | OXYCODONE |
| CNS | Neuropathic pain | AMITRIPTYLINE |
| CNS | Neuropathic pain | NORTRIPTYLINE |
| CNS | Neuropathic pain | GABAPENTIN |
| CNS | Neuropathic pain | SODIUM VALPROATE |
| CNS | Neuropathic pain | PHENYTOIN |
| CNS | Neuropathic pain | KETAMINE |
| CNS | Neuropathic pain (Trigeminal neuralgia) | CARBAMAZEPINE |
| CNS | Neuropathic pain (Trigeminal neuralgia) | OXCARBAZEPINE |
| CNS | Neuropathic pain (Trigeminal neuralgia) | GABAPENTIN |
| CNS | Neuropathic pain (Trigeminal neuralgia) | LAMOTRIGINE |
| CNS | Neuropathic pain (Trigeminal neuralgia) | FOSPHENYTOIN SODIUM |
| CNS | Neuropathic pain (Postherpetic neuralgia) | AMITRIPTYLINE |
| CNS | Neuropathic pain (Postherpetic neuralgia) | GABAPENTIN |
| CNS | Analgesics | MEPROBAMATE |
| CNS | Analgesics | PARACETAMOL |
| CNS | Analgesics | METHIONINE (CO-METHIAMOL) |
| CNS | Analgesics | DIHYDROCODEINE TARTRATE |
| CNS | Analgesics | IBUPROFEN |
| CNS | Analgesics | FLURBIPROFEN |
| CNS | Analgesics | DICLOFENAC POTASSIUM |
| CNS | Analgesics | NAPROXEN |
| CNS | Analgesics | TOLFENAMIC ACID |
| CNS | 5HT1 agonists | ALMOTRIPTAN |
| CNS | 5HT1 agonists | NARATRIPTAN |
| CNS | 5HT1 agonists | RIZATRIPTAN |
| CNS | 5HT1 agonists | SUMATRIPTAN |
| CNS | 5HT1 agonists | ZOLMITRIPTAN |
| CNS | Ergot alkaloids | ERGOTAMINE TARTRATE |
| CNS | Ergot alkaloids | ERGOTAMINE TARTRATE |
| CNS | Other drugs | ISOMETHEPTENE MUCATE |
| CNS | Other drugs | Pizotifen |
| CNS | Other drugs | PIZOTIFEN |
| CNS | Other drugs | CLONIDINE HYDROCHLORIDE |
| CNS | Other drugs | METHYSERGIDE |
| CNS | Antiepileptics (control of Epilepsy) | CARBAMAZEPINE |
| CNS | Antiepileptics (control of Epilepsy) | CARBAMAZEPINE |
| CNS | Antiepileptics (control of Epilepsy) | OXCARBAZEPINE |
| CNS | Antiepileptics (control of Epilepsy) | ETHOSUXIMIDE |
| CNS | Antiepileptics (control of Epilepsy) | ETHOSUXIMIDE |

TABLE 1-continued

| TYPE | CLASS | TRADE NAME |
|---|---|---|
| CNS | Antiepileptics (control of Epilepsy) | GABAPENTIN |
| CNS | Antiepileptics (control of Epilepsy) | LAMOTRIGINE |
| CNS | Antiepileptics (control of Epilepsy) | LEVETIRACETAM |
| CNS | Antiepileptics (control of Epilepsy) | PHENOBARBITAL (Phenobarbitone) |
| CNS | Antiepileptics (control of Epilepsy) | PRIMIDONE |
| CNS | Antiepileptics (control of Epilepsy) | PHENYTOIN |
| CNS | Antiepileptics (control of Epilepsy) | TIAGABINE |
| CNS | Antiepileptics (control of Epilepsy) | TOPIRAMATE |
| CNS | Antiepileptics (control of Epilepsy) | SODIUM VALPROATE |
| CNS | Antiepileptics (control of Epilepsy) | SODIUM VALPROATE |
| CNS | Antiepileptics (control of Epilepsy) | VALPROIC ACID |
| CNS | Antiepileptics (control of Epilepsy) | VIGABATRIN |
| CNS | Antiepileptics (control of Epilepsy) | CLOBAZAM |
| CNS | Antiepileptics (control of Epilepsy) | CLONAZEPAM |
| CNS | Antiepileptics (control of Epilepsy) | ACETAZOLAMIDE |
| CNS | Antiepileptics (control of Epilepsy) | PIRACETAM |
| CNS | Antiepileptics (control of Status Epilepticus) | DIAZEPAM |
| CNS | Antiepileptics (control of Status Epilepticus) | CLONAZEPAM |
| CNS | Antiepileptics (control of Status Epilepticus) | FOSPHENYTOIN SODIUM |
| CNS | Antiepileptics (control of Status Epilepticus) | LORAZEPAM |
| CNS | Antiepileptics (control of Status Epilepticus) | PARALDEHYDE |
| CNS | Antiepileptics (control of Status Epilepticus) | PHENYTOIN |
| CNS | Antiepileptics (control of Status Epilepticus) | PHENYTOIN |
| CNS | Dopaminergic drugs used in parkinsonism | LEVODOPA |
| CNS | Dopaminergic drugs used in parkinsonism | CO-BENELDOPA |
| CNS | Dopaminergic drugs used in parkinsonism | CO-CARELDOPA |
| CNS | Dopaminergic drugs used in parkinsonism | AMANTADINE HYDROCHLORIDE |
| CNS | Dopaminergic drugs used in parkinsonism | BROMOCRIPTINE |
| CNS | Dopaminergic drugs used in parkinsonism | BROMOCRIPTINE |
| CNS | Dopaminergic drugs used in parkinsonism | CABERGOLINE |
| CNS | Dopaminergic drugs used in parkinsonism | ENTACAPONE |
| CNS | Dopaminergic drugs used in parkinsonism | LISURIDE MALEATE (Lysuride Maleate) |
| CNS | Dopaminergic drugs used in parkinsonism | PERGOLIDE |
| CNS | Dopaminergic drugs used in parkinsonism | PRAMIPEXOLE |
| CNS | Dopaminergic drugs used in parkinsonism | ROPINIROLE |
| CNS | Dopaminergic drugs used in parkinsonism | SELEGILINE HYDROCHLORIDE |
| CNS | Antimuscarinic drugs used in parkinsonism | BENZATROPINE MESILATE |
| CNS | Antimuscarinic drugs used in parkinsonism | BIPERIDEN HYDROCHLORIDE |
| CNS | Antimuscarinic drugs used in parkinsonism | ORPHENADRINE HYDROCHLORIDE |

TABLE 1-continued

| TYPE | CLASS | TRADE NAME |
|---|---|---|
| CNS | Antimuscarinic drugs used in parkinsonism | ORPHENADRINE HYDROCHLORIDE |
| CNS | Antimuscarinic drugs used in parkinsonism | PROCYCLIDINE HYDROCHLORIDE |
| CNS | Antimuscarinic drugs used in parkinsonism | TRIHEXYPHENIDYL HYDROCHLORIDE/ BENZHEXOL HYDROCHLORIDE |
| CNS | Drugs used in essential tremor, chorea, tics, and related disorders | HALOPERIDOL |
| CNS | Drugs used in essential tremor, chorea, tics, and related disorders | PIRACETAM |
| CNS | Drugs used in essential tremor, chorea, tics, and related disorders | RILUZOLE |
| CNS | Drugs used in essential tremor, chorea, tics, and related disorders | TETRABENAZINE |
| CNS | Alcohol dependence | ACAMPROSATE CALCIUM |
| CNS | Alcohol dependence | DISULFIRAM |
| CNS | Cigarette smoking | BUPROPION |
| CNS | Cigarette smoking | NICOTINE |
| CNS | Opioid dependence | BUPRENORPHINE |
| CNS | Opioid dependence | LOFEXIDINE HYDROCHLORIDE |
| CNS | Opioid dependence | METHADONE HYDROCHLORIDE |
| CNS | Opioid dependence | NALTREXONE HYDROCHLORIDE |
| CNS | Drugs for dementia | DONEPEZIL HYDROCHLORIDE |
| CNS | Drugs for dementia | GALANTAMINE |
| CNS | Drugs for dementia | RIVASTIGMINE |

In certain embodiments, the organic compound, after fluorination, is biologically active. In certain embodiments, the organic compound, prior to fluorinated, is also biologically active.

In certain embodiments, the process provides after fluorination of the organic compound a known biologically active fluorinated compound, such as a fluorinated agrochemical or fluorinated pharmaceutical agent.

For example, in certain embodiments, the process provides after fluorination of the organic compound the known fluorinated pharmaceutical agent LIPITOR:

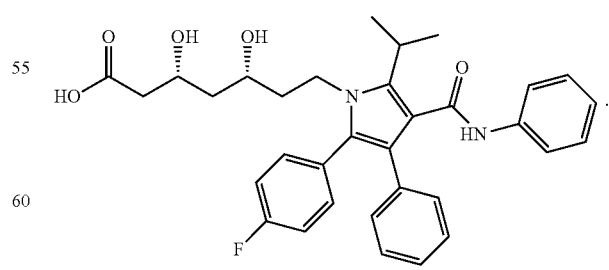

In certain embodiments, the process provides after fluorination of the organic compound the known fluorinated pharmaceutical agent PAXIL:

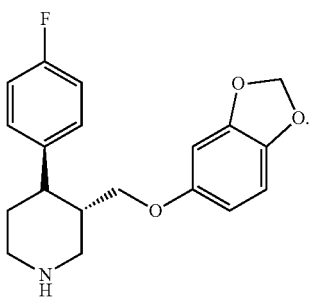

In certain embodiments, the process provides after fluorination of the organic compound the known fluorinated pharmaceutical agent LEXAPRO:

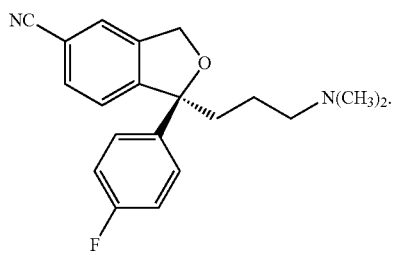 [SMILES: CN(C)CCC[C@@]1(c2ccc(F)cc2)OCc2cc(C#N)ccc21]

However, in certain embodiments, the process provides after fluorination of the organic compound a new biologically active fluorinated compound, such as a fluorinated derivative of a known agrochemical or pharmaceutical agent. In this context, a "fluorinated derivative of a known compound" is a known compound which is labeled with fluorine (i.e., one or more substituents of a known compound are replaced with fluorine).

For example, in certain embodiments, the process provides after fluorination of the organic compound a fluorinated derivative of the pharmaceutical agent vancomycin:

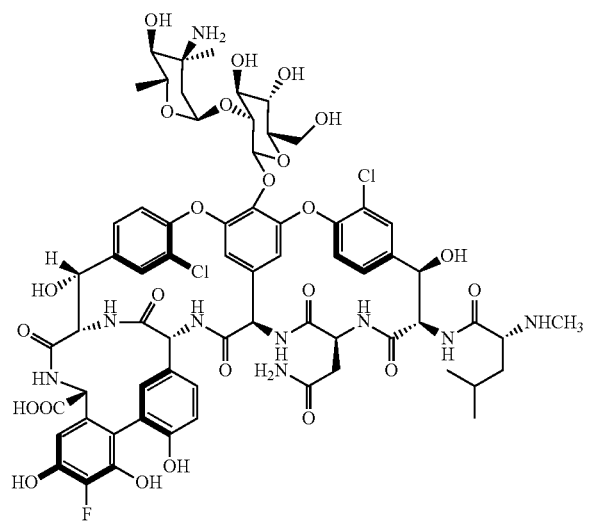

In certain embodiments, the process provides after fluorination of the organic compound a fluorinated derivative of the pharmaceutical agent MORPHINE:

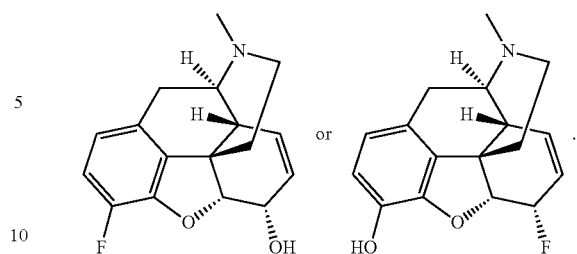

In certain embodiments, the process provides after fluorination of the organic compound the known fluorinated pharmaceutical agent ZYPREXA:

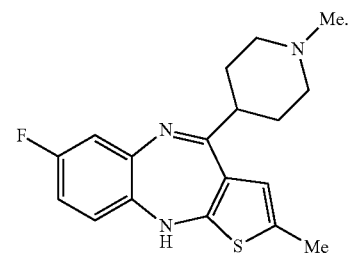 [SMILES: Cc1cc2c(s1)Nc1ccc(F)cc1N=C2C1CCN(C)CC1]

In certain embodiments, the process provided after fluorination of the organic compound a fluorinated derivative of the pharmaceutical agent tetracycline:

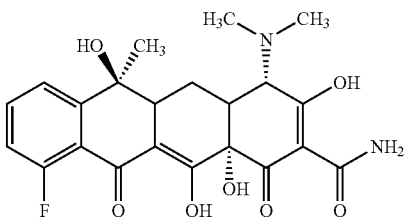 [SMILES: CN(C)[C@@H]1C(O)=C(C(N)=O)C(=O)[C@@]2(O)C(O)=C3C(=O)c4c(F)cccc4[C@@](C)(O)C3CC12]

Exemplary Reaction Conditions

Described herein are compositions comprising a palladium complex described herein, including a reaction mixture, e.g., a reaction mixture that is present during a method or process described herein. As defined generally herein, in certain embodiments, the process comprises mixing a substrate and a palladium(IV) complex described herein, under conditions sufficient to fluorinate the organic compound, to thereby provide a fluorinated organic compound.

In other embodiments, the process requires mixing a palladium(II) complex described herein with a fluorinating agent and a substrate, under conditions sufficient to fluorinate the substrate, thereby providing a fluorinated organic compound. In certain embodiments, the palladium(II) complex is combined with the fluorinating agent prior to addition of the substrate. In certain embodiments, this step results in formation of an intermediate palladium(IV) complex, which may or may not be isolated.

In certain embodiments, the palladium complex is bound to a solid support.

The substrate may be an organic compound comprising an enol silyl ether, or an organometallic compound such as a palladium(II) aryl complex or an arylsilver complex.

In certain embodiments, the method further comprises a solvent. In certain embodiments, the solvent is an organic solvent. In certain embodiments, the solvent is an aprotic solvent. Exemplary organic solvents include, but are not limited to, benzene, toluene, xylenes, methanol, ethanol, isopropanol, acetonitrile, acetone, ethyl acetate, ethyl ether, tetrahydrofuran, methylene chloride, dichloroethane and chloroform, or a mixture thereof. In certain embodiments, the solvent is acetonitrile. In certain embodiments, the solvent is methylene chloride. In certain embodiments, the solvent is tetrahydrofuran. In certain embodiments, the solvent is dichloroethane. In certain embodiments, the solvent is benzene.

In certain embodiments, the reaction further comprises heating. In certain embodiments, the reaction takes place under an inert atmosphere (e.g, an atmosphere of an inert gas such as nitrogen or argon). In certain embodiments, the reaction takes place under anhydrous conditions (e.g., conditions that are substantially free of water).

Applications

The present invention provides a process for fluorination of organic compounds, and, as such, has many useful applications. In certain embodiments, the fluorination reaction is regiospecific.

Introduction of fluorine into a certain position of bioactive compound such as a pharmaceutical agent and an agricultural chemical may remarkably reduce the toxicity of the compound. This is due to the mimic and blocking effect characterized by fluorine. Many compounds, such as 5-fluorouracil, have been reported as successful examples.

Attempts to efficiently synthesize fluorine-containing compounds are performed in many fields. Methods to introduce fluorine into a certain position through the use of fluorinating agents or the use of fluorine-containing building blocks have been reported (see, for example, Liu et al., *J. Am. Chem. Soc.* (1981) 103:7195; Lovey et al., *J. Med. Chem.* (1982) 25:71; and Kikuchi et al., *Yuki Gosei Kagaku Kyokaishi* (1997) 55:88).

Organofluorine compounds are emerging as chemical specialties of significant and increasing commercial interest. A major driver has been the development of fluorine-containing bio-active molecules for use as medicinal and plant-protection agents. Other new applications involving organofluorine chemistry are in the synthesis of liquid crystals, surface active agents, specialty coatings, reactive dyes, and even olefin polymerization catalysts.

$^{19}$F-fluorinated organic compounds may be useful for magnetic resonance imaging (MRI) technology. MRI is a is primarily a medical imaging technique most commonly used in radiology to visualize the structure and function of the body. It provides detailed images of the body in any plane. MRI contrast agents are a group of contrast media used to improve the visibility of internal body structures in MRI. Contrast agents alter the relaxation times of tissues and body cavities where they are present, which depending on the image weighting can give a higher or lower signal. Fluorine-containing contrast agents may be especially useful due to the lack of fluorine chemistry in the human body. This could, for example provide a detailed view of acidic regions, such as those containing cancer cells. $^{19}$F-labeled MRI contrast agents may add chemical sensitivity to MRI and could be used to track disease progression without the need to take tissue or fluid samples.

$^{19}$F-fluorinated organic compounds may also be useful as probes for nuclear magnetic resonance (NMR) spectroscopy. Fluorine has many advantages as a probe for NMR spectroscopy of biopolymers. $^{19}$F has a spin of one-half, and its high gyromagnetic ratio contributes to its high sensitivity (approximately 83% of the sensitivity of $^{1}$H). It also facilitates long-range distance measurements through dipolar-dipolar coupling. Moreover, the near-nonexistence of fluorine atoms in biological systems enables $^{19}$F NMR studies without background signal interference. Furthermore, the chemical shift of $^{19}$F has been shown to be very sensitive to its environment.

$^{18}$F-fluorinated organic compounds are particularly useful for positron-emission tomography (PET) imaging technology. PET is a noninvasive imaging technology that is currently used in the clinic to image cancers and neurological disorders at an early stage of illness. PET tracers are molecules which incorporate a PET-active nucleus and can therefore be visualized by their positron emission in the body. The fluorine isotope $^{18}$F is the most common nucleus for PET imaging because of its superior properties to other nuclei.

A commonly used PET tracer is 2-deoxy-2-fluoroglucose (FDG), which behaves like glucose in the body and is transported to sites of high metabolism such as cancer cells. FDG is not itself metabolized and therefore accumulates in cancer tissues, which in turn can be visualized. The non-invasive nature and the high sensitivity render PET a powerful method for early cancer identification using FDG.

The $^{18}$F radioisotope has a half-life of 109 minutes. The short half-life dictates restrictions on chemical synthesis of PET tracers, because introduction of the fluorine atom has to take place at a very late stage of the synthesis to avoid the unproductive decay of $^{18}$F before it is injected into the body. Fluoride ion is the most common reagent to introduce $^{18}$F but the specific chemical properties of the fluoride ion currently limit the available pool of PET tracers. Due to the narrow functional group compatibility of the strongly basic fluoride ion, only a limited set of chemical reactions can be employed for fluorination, and hence the synthesis of PET tracers is limited to fairly simple molecules such as FDG. The field of PET imaging would benefit from the availability of a new method that is capable of introducing radiolabeled fluoride into structurally more complex organic molecules. An easy access to drug-based PET tracers would simplify determining the fate of such drugs in the body and thereby help to identify and understand their mode of action, bioavailability and time-dependent biodistribution.

Methods of Treatment

A fluorinated compound described herein, such as a fluorinated pharmaceutical agent, can be administered to cells in culture, e.g. in vitro or ex vivo, or to a subject, e.g., in vivo, to treat, prevent, and/or diagnose a variety of disorders, including those described herein below. In some embodiments, the fluorinated compound is made by a method described herein.

As used herein, the term "treat" or "treatment" is defined as the application or administration of a compound, alone or in combination with, a second compound to a subject, e.g., a patient, or application or administration of the compound to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

As used herein, an amount of a compound effective to treat a disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to prevent a disorder, or a "a prophylactically effective amount" of the compound refers to an amount effective, upon single- or multiple-dose administration to the subject, in preventing or delaying the occurrence of the onset or recurrence of a disorder or a symptom of the disorder. As used herein, the term "subject" is intended to include human and non-human animals. Exemplary human subjects include a human patient having a disorder, e.g., a disorder described herein or a normal subject. The term "non-human animals" of the invention includes all vertebrates, e.g., non-mammals (such as chickens, amphibians, reptiles) and mammals, such as non-human primates, domesticated and/or agriculturally useful animals, e.g., sheep, dog, cat, cow, pig, etc.

Described herein are compounds and compositions useful in the treatment of a disorder. In general, the compounds described herein are fluorinated derivatives of a pharmaceutical agent (e.g., a fluorinated estrone). Also envisioned herein are other compounds, wherein one or more fluorine moieties have been added to the pharmaceutical agent, e.g., replacing a hydrogen or functional group such as an —OH with a fluorine.

Compositions and Routes of Administration

The compositions delineated herein include the fluorinated compounds delineated herein, such as fluorinated pharmaceutical agents, as well as additional therapeutic agents if present, in amounts effective for achieving a modulation of disease or disease symptoms, including those described herein. In some embodiments, the fluorinated compound is made by a method described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

A compound described herein (e.g., a palladium complex described herein, an organic compound, a fluorinating agent, or a fluorinated compound, such as a fluorinated pharmaceutical agent) may be provided in a kit. The kit includes (a) a compound used in a method described herein, and, optionally (b) informational material. The informational material can be descriptive, instructional, marketing or other material that relates to the methods described herein and/or the use of the compounds for the methods described herein. In some embodiments, the palladium complex is bound to a solid support.

The informational material of the kits is not limited in its form. In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance, a dye or coloring agent, for example, to tint or color one or more components in the kit, or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

In some embodiments, the components of the kit are stored under inert conditions (e.g., under Nitrogen or another inert gas such as Argon). In some embodiments, the components of the kit are stored under anhydrous conditions (e.g., with a desiccant). In some embodiments, the components are stored in a light blocking container such as an amber vial.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

EXAMPLES

The examples below are included merely for purposes of illustration of certain aspects and embodiments of the present invention and is not intended to limit the invention.

Example 1

Synthesis and Characterization of a Palladium(IV) Fluoride

High-valent palladium fluorides are potential intermediates and reagents for the synthesis of aryl fluorides, which are important as pharmaceuticals and as tracers for positron-emission tomography (Müller, K.; Faeh, C.; Diederich, F. *Science* 2007, 317, 1881-1886; Lasne, M. C.; Perrio, C.; Rouden, J.; Bane, L.; Roeda, D.; Dolle, F.; Crouzel, C., Chemistry of beta(+)-emitting compounds based on fluorine-18. In Contrast Agents II, 2002; Vol. 222, pp 201-258; each of which is incorporated herein by reference). We have recently reported the palladium-mediated fluorination of arylboronic acids to form functionalized fluoroarenes and speculated on the intermediacy of discrete high-valent palladium fluorides. High-valent palladium fluoride complexes have also been suggested in other carbon-fluorine bond formations. In 2006, Sanford published the palladium-catalyzed fluorination of phenylpyridine derivatives and related substrates using electrophilic fluorination sources as oxidants under microwave irradiation at 100-150° C. (Hull, K. L.; Anani, W. Q.; Sanford, M. S. *J. Am. Chem. Soc.* 2006, 128, 7134-7135; incorporated herein by reference). While high-valent palladium complexes may be intermediates in this transformation, none have been reported to date. In 2008, Vigalok and Vedernikov communicated the formation of fluorobenzene and iodobenzene in 10% and 90% yield, respectively, upon treatment of a diphosphine arylpalladium iodide with 1-fluoro-2,4,6-trimethylpyridinium tetrafluoroborate (Yahav-Levi, A.; Goldberg, I.; Vigalok, A.; Vedernikov, A. N. *J. Am. Chem. Soc.* 2008, 130, 724-731; incorporated herein by reference). The transient formation of a palladium(IV) fluoride followed by either carbon-iodine or carbon-fluorine bond formation via reductive elimination is a potential mechanistic pathway that would explain the observed products. Although discrete high-valent palladium fluorides are potential intermediates in all three examples—Sanford's, Vigalok's, and our own—electrophilic palladium-carbon bond cleavage is a mechanistic alternative which has not been ruled out in any of these examples; in no instance has a high-valent palladium fluoride been observed. In 1992, Canty reported the reaction of a palladium(IV) bromide with silver (I) fluoride to presumably generate a benzyldimethylpalladium(IV) fluoride that was observed by $^1$H NMR (Canty, A. J.; Traill, P. R.; Skelton, B. W.; White, A. H. *J. Organomet. Chem.* 1992, 433, 213-222; incorporated herein by reference). While hundreds of early transition metal fluorides have been structurally characterized (Murphy, E. F.; Murugavel, R.; Roesky, H. W. *Chem. Rev.* 1997, 97, 3425-3468; incorporated herein by reference), only eight palladium complexes with terminal fluoride ligands can be found in the Cambridge Structural Database, none of which contain a palladium center in an oxidation state other than +II (Fraser, S. L.; Antipin, M. Y.; Khroustalyov, V. N.; Grushin, V. V. *J. Am. Chem. Soc.* 1997, 119, 4769-4770; Marshall, W. J.; Thorn, D. L.; Grushin, V. V. *Organometallics* 1998, 17, 5427-5430; Roe, D. C.; Marshall, W. J.; Davidson, F.; Soper, P. D.; Grushin, V. V. *Organometallics* 2000, 19, 4575-4582; Grushin, V. V.; Marshall, W. J. *Angew. Chem., Int. Eel.* 2002, 41, 4476-4479; Yahav, A.; Goldberg, I.; Vigalok, A. *J. Am. Chem. Soc.* 2003, 125, 13634-13635; Jasim, N. A.; Perutz, R. N.; Whitwood, A. C.; Braun, T.; Izundu, J.; Neumann, B.; Rothfeld, S.; Stammler, H.-G. *Organometallics* 2004, 23, 6140-6149; Grushin, V. V.; Marshall, W. J. *J. Am. Chem. Soc.* 2006, 128, 12644-12645; Kaspi, A. W.; Yahav-Levi, A.; Goldberg, I.; Vigalok, A. *Inorg. Chem.* 2008, 47, 5-7; each of which is incorporated herein by reference).

In this Example, the synthesis of a well-defined organometallic palladium(IV) fluoride and its characterization are described. To our knowledge, no high-valent palladium fluoride has previously been characterized by either $^{19}$F NMR or X-ray crystallography. Three structural design elements were considered to synthesize a stable palladium(IV) fluoride. Firstly, we targeted complexes containing a single carbon-based ligand. Carbon-based ligands are strong σ-donors and can thus stabilize high-valent palladium centers, but the presence of multiple carbon-based ligands can result in carbon-carbon reductive elimination with concurrent reduction of the metal center (Canty, A. J.; Traill, P. R.; Skelton, B. W.; White, A. H. *J. Organomet. Chem.* 1992, 433, 213-222; incorporated herein by reference). Similarly, other X-type ligands, such as amido and alkoxide ligands, can support high-valent metal centers by both σ- and π-donation, but also participate in reductive elimination from palladium(IV) to form carbon-X bonds (Dick, A. R.; Kampf, J. W.; Sanford, M. S. *J. Am. Chem. Soc.* 2005, 127, 12790-12791; Pawlikowski, A. V.; Getty, A. D.; Goldberg, K. I. *J. Am. Chem. Soc.* 2007, 129, 10382-10393; each of which is incorporated herein by reference). Secondly, neutral nitrogenous donors were selected because they are known to stabilize high-valent metal centers and typically do not participate in reductive elimination (Berry, J. F.; Bill, E.; Bothe, E.; George, S. D.; Mienert, B.; Neese, F.; Wieghardt, K. *Science* 2006, 312, 1937-1941; incorporated herein by reference). Finally, we envisioned rigid ligand scaffolds would stabilize the anticipated octahedral coordination sphere of palladium(IV) and thus disfavor reductive elimination and other reductive pathways from an octahedral $d^6$ palladium(IV) to a square planar $d^8$ palladium (II) (Cámpora, J.; Palma, P.; del Rio, D.; López, J. A.; Álvarez, E.; Connelly, N. G. Organometallics 2005, 24, 3624-3628; incorporated herein by reference). Tetrapyrazolylborate (Tp) ligands position three neutral nitrogen donor atoms in a facial geometry for chelation to a transition metal (Trofimenko, S. J. Am. Chem. Soc. 1967, 89, 3170-3177; Trofimenko, S. Acc. Chem. Res. 1971, 4, 17-22; Trofimenko, S. Chem. Rev. 1993, 93, 943-980; each of which is incorporated herein by reference). The Tp ligand has been used in organometallic chemistry to stabilize octahedral complexes due to the three N-Metal-N bond angles near 90°. The N,N-dimethylaminonaphthyl ligand was selected because it can be installed on palladium by cyclometallation to form a rigid, electron-rich five-membered chelate.

Cyclometallation of N,N-dimethyl-1-naphthylmethanamine (1) with disodium tetrachloropalladate afforded the palladium(II) chloride dimer (2) in 58% yield (FIG. 1). The chloride ligands were subsequently substituted using one equivalent of potassium tetrapyrazolylborate per palladium to afford the palladium(II) borate 3 in 74% yield. Line broadening in the $^1$H and $^{13}$C NMR spectra of 3 at room temperature is consistent with previously observed dynamic coordination/dissociation of the pyrazolyl ligands of the Tp ligand to palladium (Onishi, M.; Ohama, Y.; Sugimura, K.; Hiraki, K. Chem. Lett. 1976, 955-958; incorporated herein by reference); sharper resonances could be observed at –50° C. Oxidation of 3 with commercially available 1-fluoro-pyridinium triflate (4) afforded a discrete new compound by $^1$H and $^{19}$F NMR. A $^{19}$F NMR fluorine resonance was observed at –287.4 ppm; no other values for $^{19}$F NMR resonances of high-valent palladium fluorides are available, but $^{19}$F NMR shifts of palladium(II) fluorides have been reported in a range from –268 to –301 ppm (Fraser, S. L.; Antipin, M. Y.; Khroustalyov, V. N.; Grushin, V. V. J. Am. Chem. Soc. 1997, 119, 4769-4770; Grushin, V. V.; Marshall, W. J. J. Am. Chem. Soc. 2006, 128, 12644-12645; each of which is incorporated herein by reference). Additionally, the line broadening in the NMR spectra observed for 3 was not observed for the new compound 5. The palladium fluoride 5 was unstable toward water and when heated in an acetone solution to 50° C.; purification, isolation or structural characterization of 5 was not pursued.

The more stable palladium(IV) fluoride 7 could be prepared when using 1-fluoro-2,4,6-trimethylpyridinium hexafluorophosphate (6), an electrophilic fluorination reagent specifically prepared for this purpose (eq 1). The palladium(IV) fluoride complex 7 with a hexafluorophosphate counteranion is more stable than the palladium triflate 5. High-valent palladium fluoride 7 is a moisture- and air-stable orange solid that can be stored in ambient atmosphere without decomposition for at least one week. The solution structure of 7 was characterized by five NMR-active nuclei. Similar to the $^{19}$F NMR resonance observed for 5, a $^{19}$F NMR resonance for 7 is observed is at –294.0 ppm in addition to the hexafluorophosphate resonance at –72.7 ppm. The NMR data is consistent with a cationic octahedral palladium(IV) fluoride complex in which three of the four pyrazolyl substituents of the Tp ligand are complexed to palladium. A $^4J_{F-H}$ coupling of 3.4 Hz from one benzyl hydrogen to the terminal fluoride in the $^1$H NMR of 7 was observed. In addition, a coupling constant of 6.5 Hz was observed in the $^{13}$C NMR spectrum for one of the carbon atoms of the two amine methyl groups that we attribute to a $^3J_{F-C}$ coupling. An H-F HSQC NMR experiment was performed which both confirmed the $^4J_{F-H}$ coupling and demonstrated the simultaneous coordination of the dimethylamino ligand and the fluoride ligand to palladium in solution.

Figure 2:
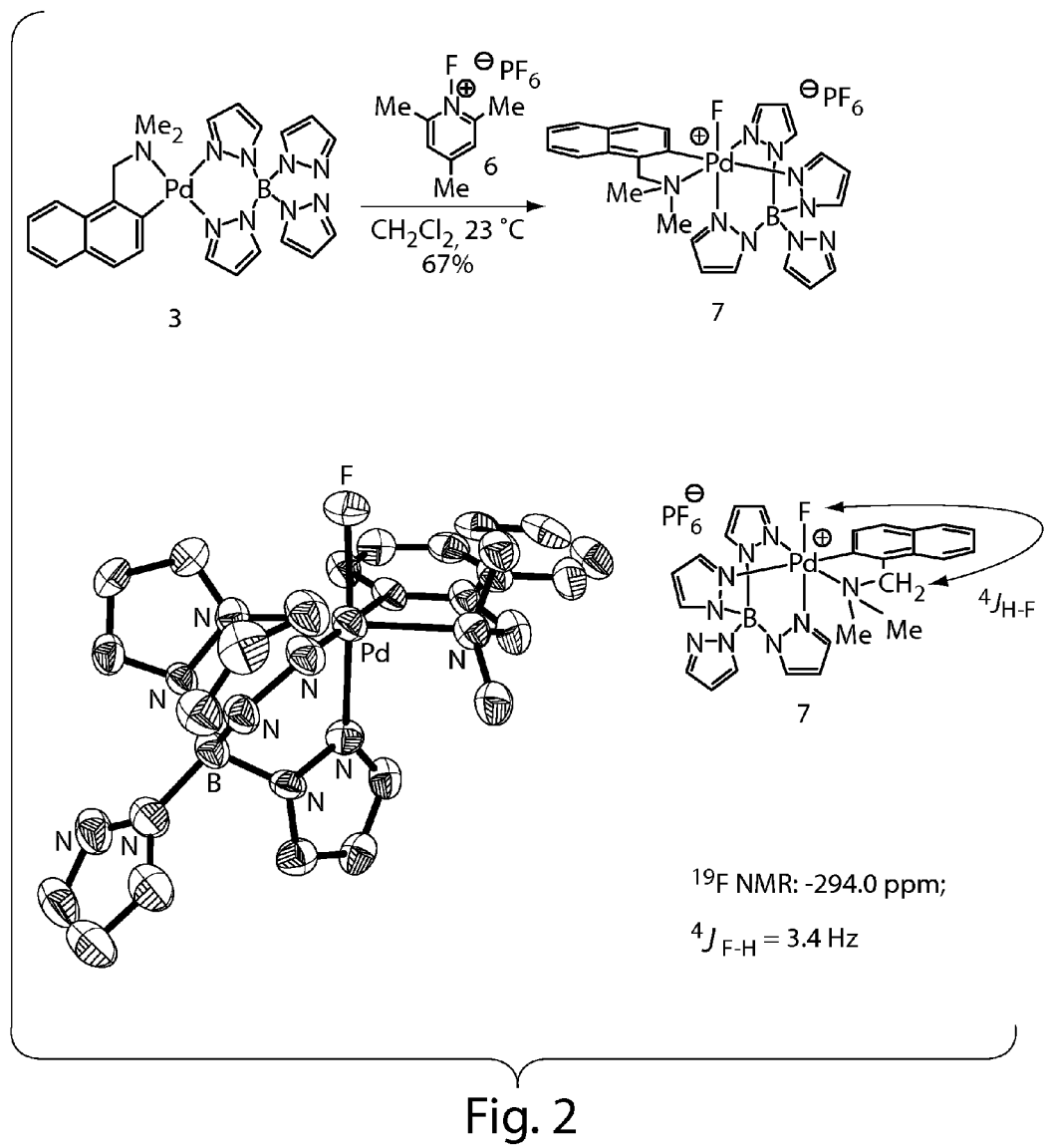
FIG. 2 is an ORTEP drawing of a palladium(IV) fluoride complex with ellipsoids drawn at 50% probability. Hydrogen atoms, the $PF_6^-$ counterion, and solvent molecules are omitted for clarity. Representative bond lengths [Å]: Pd(1)-F(1), 1.923 (4); Pd(1)-N(2), 2.005 (6); Pd(1)-C(2), 2.024 (8); Pd(1)-N(6), 2.031 (7); Pd(1)-N(1), 2.089 (7); Pd(1)-N(4), 2.154 (7). Representative angles [°]: F(1)-Pd(1)-N(2), 175.4 (2); F(1)-Pd(1)-C2, 88.4(3); F(1)-Pd(1)-N(6), 87.5 (3); F(1)-Pd(1)-N(1), 91.1 (2); F(1)-Pd(1)-N(4), 89.8 (2); N(2)-Pd(1)-C(2), 90.4 (3); C(2)-Pd(1)-N(6), 98.2 (3); N(2)-Pd(1)-N(1), 93.1 (3); N(6)-Pd(1)-N(1), 178.0 (3); C(2)-Pd(1)-N(4), 177.6 (3).
Figure 3:
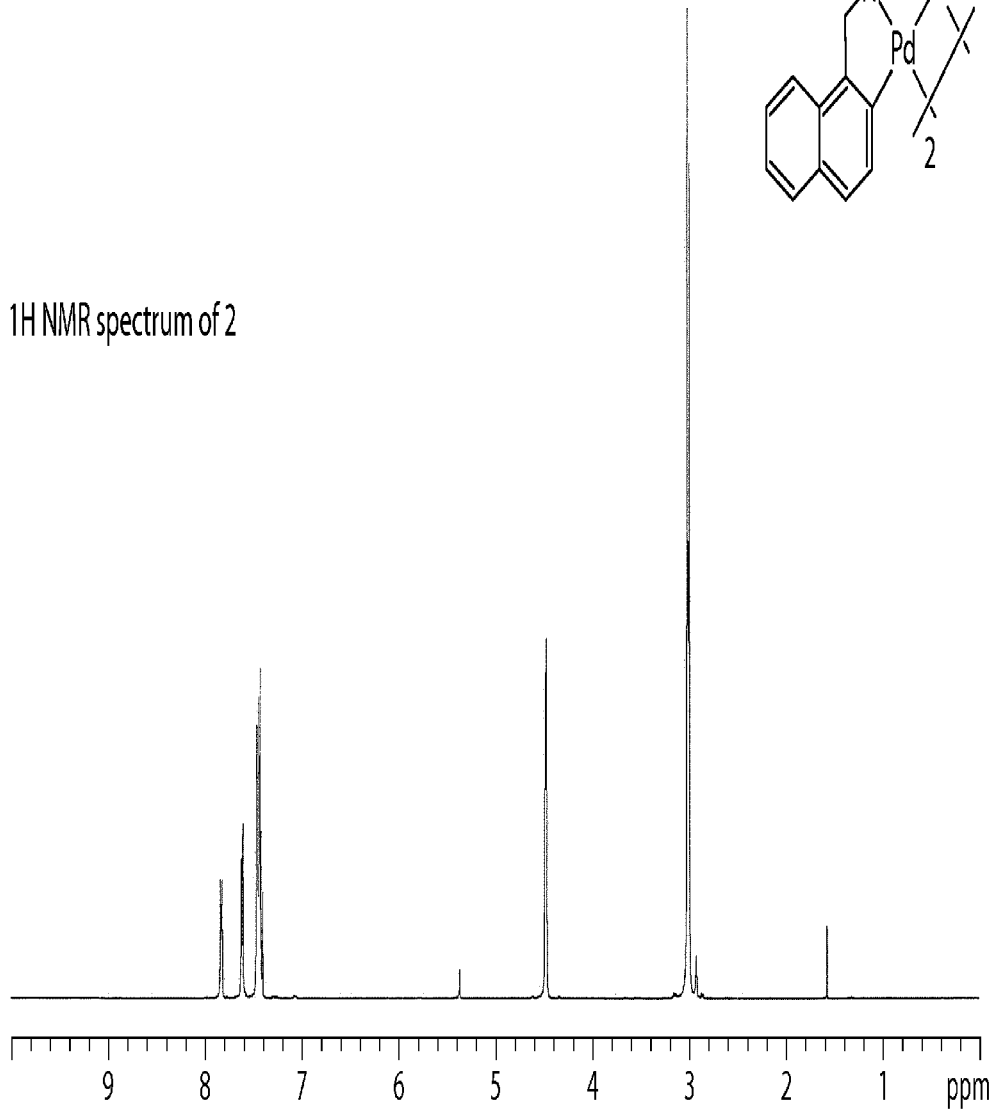
FIG. 3 is a $^1H$ NMR spectrum of the palladium(II) chloride dimer.

To unambiguously establish the connectivity of 7, crystals suitable for X-ray crystallographic analysis were obtained by cooling a solution of 7 that was heated at reflux in methylene chloride/hexane/benzene. The compound crystallized as orange-yellow plates in the triclinic space group P$\bar{1}$. Disorder was observed only for the hexafluorophosphate counteranion, which was treated with a two-site disorder model [P(1), F(2), F(3), F(4), F(5), F(6), F(7)] and [P(1'), F(2'), F(3'), F(4'), F(5'), F(6'), F(7')] with refined site occupancy factors of 0.80 (2) and 0.20 (2), respectively. The disorder model was included in the least-squares refinement with mild rigid-bond, similar $U_{ij}$, 1,2- and 1,3-distance restraints. The cationic palladium fragment of the complex was fully ordered. The solid state structure of 7 confirmed the solution structure as a palladium(IV) complex with a terminal fluoride ligand (FIG. 2). The palladium-fluorine bond distance is 1.923(4) Å, which is the shortest palladium-fluorine bond observed to date. The other bond lengths and angles are within the expected values of a $d^6$ octahedral palladium(IV) complex supported by a Tp ligand.

In conclusion, we report the synthesis and characterization of an organometallic palladium(IV) fluoride complex. The complex is stable to air and moisture and thermally stable to at least 60° C.

Materials and Methods

All reactions were carried out under an ambient atmosphere. Reactions were magnetically stirred and monitored by thin layer chromatography (TLC) using EMD TLC plates pre-coated with 250 nm thickness silica gel 60 F254 plates and visualized by fluorescence quenching under UV light. In addition, TLC plates were stained using eerie ammonium molybdate or potassium permanganate stain. Flash chromatography was performed on Dynamic Adsorbents Silica Gel 40-63 μm particle size using a forced flow of eluant at 0.3-0.5 bar pressure (Still, W. C.; Kahn, M.; Mitra, A. J. Org. Chem. 1978, 43, 2925-2927; incorporated herein by reference). Concentration under reduced pressure was performed by rotary evaporation at 25-30° C. at appropriate pressure. Purified compounds were further dried under high vacuum (0.01-0.05 Ton). Yields refer to purified and spectroscopically pure compounds. Melting points were measured on a Buchi 510 apparatus. All melting points were measured in open capillaries and are uncorrected. NMR spectra were recorded on either a Varian Unity/Inova 600 spectrometer operating at 600 MHz for $^1$H acquisitions, a Varian Unity/Inova 500 spectrometer operating at 500 MHz and 125 MHz for $^1$H and $^{13}$C acquisitions, respectively, a Varian Mercury 400 spectrometer operating at 375 MHz and 160 MHz for $^{19}$F and $^{31}$P acquisitions, respectively, or a Varian Mercury 300 spectrometer operating at 100 MHz for $^{11}$B acquisitions. Chemical shifts are reported in ppm with the solvent resonace as the internal standard. Data is reported as follows: s=singlet, br=broad, d=doublet, t=triplet, q=quartet, quin=quintet, m=multiplet; coupling constants in Hz; integration. High-resolution mass spectra were obtained on Jeol AX-505 or SX-102 spectrometers at the Harvard University Mass Spectrometry Facilities. Na$_2$PdCl$_4$.3H$_2$O and KBH$_4$ were purchased from Strem. 1-Naphthaldehyde, Me$_2$NH.HCl, and NH$_4$PF$_6$ were purchased from Alfa Aesar. Pyrazole was obtained from Aldrich and 1-fluoro-2,4,6-trimethylpyridinium triflate was purchased from TCI America and used as received.

Experimental Data

Experimental Procedures and Compound Characterization

Potassium tetra(1H-pyrazol-1-yl)borate

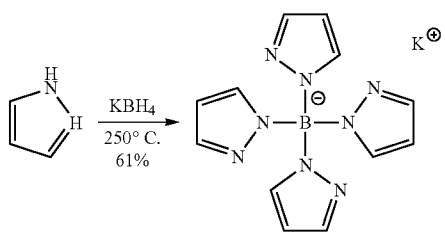

As solids, $KBH_4$ (1.00 g, 18.6 mmol, 1.00 equiv) and pyrazole (7.61 g, 112 mmol, 6.00 equiv) are combined. This mixture is heated to 250° C. for 16 hours, after which time the melt is cooled to room temperature. The residue is triturated with $Et_2O$ (100 mL) and isolated by filtration. Washing with additional $Et_2O$ (2×50 mL) affords 3.60 g of the title compound as a colorless solid (61% yield).

Melting Point: 248-249° C. NMR Spectroscopy: $^1$H NMR (600 MHz, $D_2O$, 23° C., δ): 7.49 (s, 4H), 7.19 (d, J=2.0 Hz, 4H), 6.14 (s, 4H). $^{13}$C NMR (125 MHz, $D_2O$, 23° C., δ): 138.85, 132.84, 102.42. $^{11}$B NMR (100 MHz, $D_2O$, 23° C., δ): −1.30. Mass Spectrometry: LRMS-FIA (m/z): 279.1. These spectroscopic data correspond to reported data (Niedenzu, K.; Niedenzu, P. M. *Inorg. Chem.* 1984, 23, 3713-3716; incorporated herein by reference).

1-Fluoro-2,4,6-trimethylpyridinium hexafluorophosphate (6)

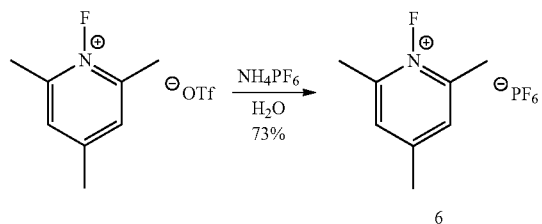

To 1-fluoro-2,4,6-trimethylpyridinium triflate (1.00 g, 3.46 mmol, 1.00 equiv) in 30 mL $H_2O$ is added $NH_4PF_6$ (1.13 g, 6.91 mmol, 2.00 equiv) in one portion at 23° C. The suspension is stirred for 1.5 hours before the solid is isolated by filtration. Recrystallization from hexanes/acetone (30 mL, 1:1 (v/v)) affords 722 mg of the title compound as a colorless solid (73% yield)

Melting Point: 182-184° C. NMR Spectroscopy: $^1$H NMR (500 MHz, acetonitrile-d3, 23° C., δ): 7.64 (d, J=6.6 Hz, 2H), 2.74 (d, J=4.1 Hz, 6H), 2.54 (s, 3H). $^{13}$C NMR (125 MHz, acetonitrile-d3, 23° C., δ): 160.15 (d, J=2.7 Hz), 148.06 (d, J=2.7 Hz), 129.30 (d, J=3.7 Hz), 21.76 (s), 16.32 (d, J=6.4 Hz). $^{19}$F NMR (375 MHz, acetonitrile-d3, 23° C., δ): 15.53 (br s), −73.36 (d, J=705.6 Hz). $^{31}$P (160 MHz, acetonitrile-d3, 23° C., δ): −143.55 (quin, J=705.9 Hz). Mass Spectrometry: HRMS-FIA (m/z): calcd for [M-$PF_6$], 140.0870. Found, 140.0867.

N,N-dimethyl(naphthalene-1-yl)methanamine (1)

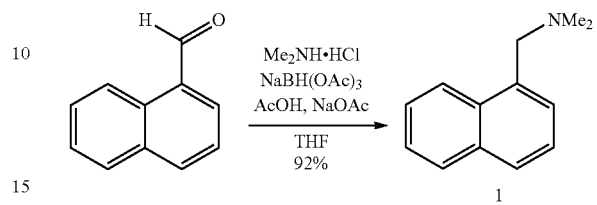

To 1-naphthaldehyde (1.50 g, 9.62 mmol, 1.00 equiv) in 40 mL THF is added NaOAc (0.79 g, 9.62 mmol, 1.00 equiv), $Me_2NH\cdot HCl$ (863 mg, 10.6 mmol, 1.10 equiv), and AcOH (0.11 mL, 1.9 mmol, 0.20 equiv) at 23° C. $NaBH(OAc)_3$ (4.08 g, 19.3 mmol, 2.00 equiv) is added in three portions over five minutes. The suspension is stirred for 12 hours before solvent is removed in vacuo. To the residue is added 10 mL sat. $NaHCO_{3(aq)}$ and 10 mL $CH_2Cl_2$. The phases are separated and the aqueous phase is extracted with $CH_2Cl_2$ (3×10 mL). The combined organic phase is concentrated in vacuo. The residue is purified by chromatography on silica gel eluting with hexanes/EtOAc 3:2 (v/v) to afford 1.64 g of the title compound as a colorless liquid (92% yield).

$R_f$=0.38 (hexane/EtOAc 2:3 (v/v)). NMR Spectroscopy: $^1$H NMR (600 MHz, $CDCl_3$, 23° C., δ): 8.27 (d, J=8.5 Hz, 1H), 7.85 (d, J=8.2 Hz, 1H), 7.79 (dd, J=6.7 Hz, 2.9 Hz, 1H), 7.53 (ddd, J=8.0 Hz, 6.5 Hz, 1.0 Hz, 1H), 7.48 (ddd, J=6.5 Hz, 5.5 Hz, 1.0 Hz, 1H), 7.43-7.40 (m, 2H), 3.82 (s, 2H), 2.31 (s, 6H). $^{13}$C NMR (125 MHz, $CDCl_3$, 23° C., δ): 134.85, 133.84, 132.52, 128.40, 127.95, 127.38, 125.98, 125.56, 125.06, 124.49, 62.60, 45.69. Mass Spectrometry: HRMS-FIA (m/z): calcd for [$C_{13}H_{15}N$+H], 186.1277. Found, 186.1286. These spectroscopic data correspond to reported data (Gay, R. L.; Hauser, C. R. *J. Am. Chem. Soc.* 1967, 89, 2297-2303; incorporated herein by reference).

Di-µ-chloro-bis(N,N-dimethyl-1-naphthylamine-8-C,N)dipalladium(II)(2)

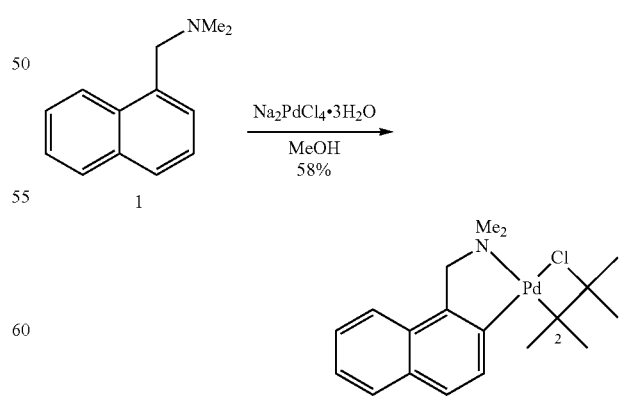

To N,N-dimethyl(naphthalene-1-yl)methanamine (1) (284 mg, 1.53 mmol, 1.00 equiv) in 15 mL MeOH is added Na₂PdCl₄·3H₂O (554 mg, 1.53 mmol, 1.00 equiv) in one portion at 23° C. A red precipitate is immediately observed. After stirring for three hours, the solid is isolated by filtration and is subsequently washed with MeOH. The solid is suspended in 30 mL benzene and heated to reflux. The suspension is filtered through celite and the filtrate is cooled to room temperature. Upon addition of 30 mL hexanes, precipitation of the title compound is observed. Filtration affords 579 mg of the title compound as an orange solid (58% yield).

Melting Point: 220-221° C. (decomp.). NMR Spectroscopy: ¹H NMR (500 MHz, CD₂Cl₂, 23° C., δ): 7.79 (d, J=7.1 Hz, 1H), 7.58-7.56 (m, 1H), 7.42-7.36 (m, 4H), 4.47 (d, J=5.5 Hz, 2H), 3.00 (d, J=9.5 Hz, 6H). ¹³C NMR (125 MHz, CD₂Cl₂, 23° C., δ): 143.25, 143.19, 141.75, 132.03, 131.83, 131.39, 129.27, 128.90, 128.65, 126.04, 125.00, 124.85, 124.63, 123.84, 71.88, 71.63, 53.80, 53.58. Mass Spectrometry: LRMS-FIA (m/z): 650.0. These spectroscopic data correspond to reported data (Julia, M.; Duteil, M.; Lallemand, *J. Organomet. Chem.* 1975, 102, 239-243; Cope, A. C.; Friedrich, E. C. *J. Am. Chem. Soc.* 1968, 90, 909-913; each of which is incorporated herein by reference).

(N,N-dimethyl[naphthalen-1-yl]methanamino)(tetrapyrazolylborate)palladium(II)(3)

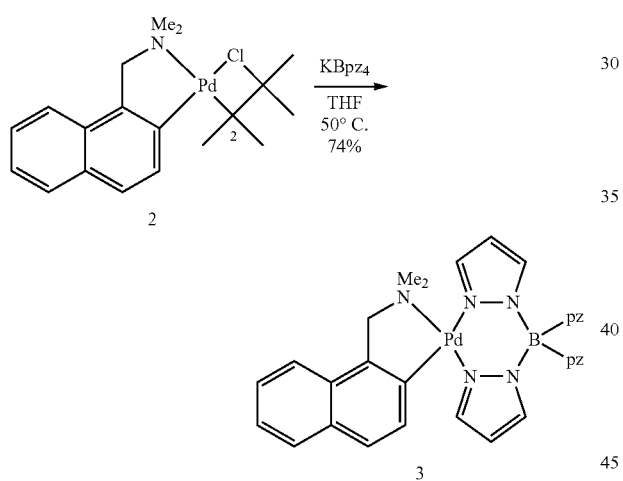

To di-μ-chloro-bis(N,N-dimethyl-1-naphthylamine-8-C, N)dipalladium(II) (2) (252 mg, 0.387 mmol, 1.00 equiv) in 7 mL THF is added potassium tetra(1H-pyrazol-1-yl)borate (KBpz₄) (246 mg, 0.774 mmol, 2.00 equiv) in one portion at 23° C. The orange suspension is heated at 50° C. for 8 hours at which time a white suspension is observed. Solvent is removed in vacuo and the residue is dissolved in 15 mL CH₂Cl₂. The suspension is filtered through celite and solvent is removed in vacuo. Trituration with Et₂O (100 mL) and filtration affords 326 mg of the title compound as a colorless solid (74%).

R_f=0.40 (EtOAc). Melting Point: 194-195° C. (decomp.). NMR Spectroscopy: ¹H NMR (500 MHz, CDCl₃, −50° C., δ): 7.86 (s, 1H), 7.82 (d, J=7.6 Hz, 1H), 7.71 (br s, 1H), 7.66 (br s, 1H), 7.59 (d, J=8.0 Hz), 7.55-7.40 (m, 8H), 6.81 (d, J=8.5 Hz, 1H), 6.76 (br s, 1H), 6.36 (br s, 1H), 6.32 (s, 1H), 6.29 (s, 1H), 6.13 (s, 1H), 4.72 (d, J=14 Hz, 1H), 4.09 (d, J=14 Hz, 1H), 2.90 (s, 3H), 2.17 (s, 3H). ¹³C NMR (125 MHz, CDCl₃, −50° C., δ): 147.94, 144.03, 142.13, 141.20, 140.83, 136.65 (br), 136.40 (br), 136.25 (br), 135.40, 134.23, 132.53, 130.82, 128.40, 128.24, 128.06, 125.58, 124.73, 124.14, 123.22, 106.43, 105.47, 104.96, 71.13, 52.86, 50.99. ¹¹B NMR (100 MHz, CDCl₃, 23° C., δ): 1.14. Mass Spectrometry: HRMS-FIA (m/z): calcd for [C₂₅H₂₆BN₉Pd+H], 570.1512. Found, 570.1492.

(N,N-dimethyl)naphthalene-1-yl]methanamino)(tetrapyrazolylborate) palladium(IV) fluoride hexafluorophosphate (7)

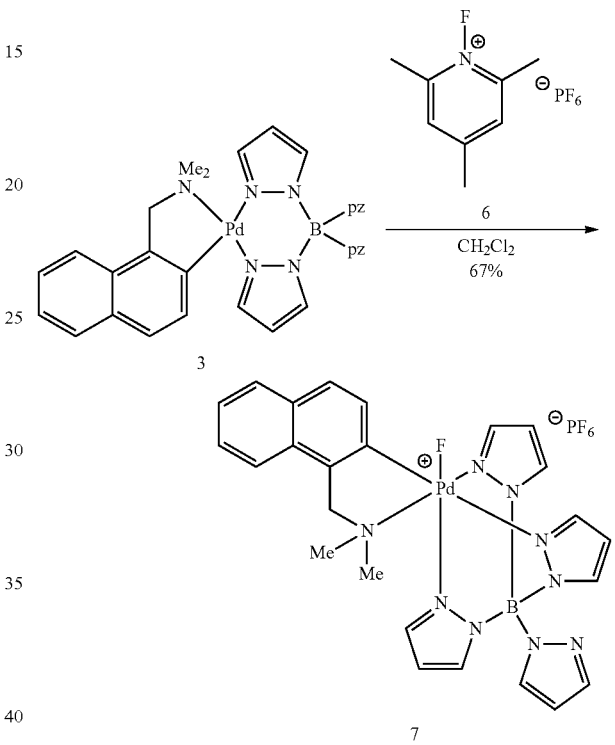

To (N,N-dimethyl[naphthalen-1-yl]methanamino)(tetrapyrazolylborate)palladium(II) (3) (148 mg, 0.260 mmol, 1.00 equiv) suspended in 4.0 mL CH₂Cl₂ is added 1-fluoro-2,4,6-trimethylpyridinium hexafluorophosphate (6) (74.2 mg, 0.260 mmol, 1.00 equiv) in one portion at 23° C. After two hours, solvent is removed in vacuo. Trituration with Et₂O (5 mL) followed by recrystallization from CH₂Cl₂/benzene affords 128 mg of the title compound as an orange solid (67%).

Melting Point: 142-144° C. NMR Spectroscopy: ¹H NMR (500 MHz, CDCl₃, 23° C., δ): 8.80 (d, J=2.6 Hz, 1H), 8.25 (d, J=2.2 Hz, 1H), 8.18 (d, J=2.1 Hz, 1H), 8.13 (d, J=2.5 Hz, 1H), 8.03 (d, J=1.5 Hz, 1H), 8.01 (d, J=8.5 Hz, 1H), 7.94 (d, J=8.1 Hz, 1H), 7.76 (br s, 1H), 7.72 (dd, J=7.3 Hz, 7.0 Hz, 1H), 7.69-7.64 (m, 2H), 7.15 (d, J=2.2 Hz, 1H), 6.77 (dd, J=2.1 Hz, 2.1 Hz, 1H), 6.66 (d, J=9.5 Hz, 1H), 6.61 (dd, J=2.3 Hz, 2.2 Hz, 1H), 6.54-6.53 (m, 2H), 6.33 (dd, J=2.3 Hz, 2.2 Hz, 1H), 5.46 (d, J=15.0 Hz, 1H), 4.87 (d, J_{H,H}=15.0 Hz, J_{H,F}=3.4 Hz, 1H), 3.54 (d, J_{H,F}=2.1 Hz, 3H), 3.06 (s, 3H). ¹⁹F NMR (375 MHz, CDCl₃, 23° C., δ): −72.65 (d, J=712.6 Hz), −293.96 (s). ³¹P NMR (160 MHz, CDCl₃, 23° C., δ): −143.22 (quin, J=713.3 Hz). ¹¹B NMR (100 MHz, CDCl₃, 23° C., δ): 1.64. Mass Spectrometry: HRMS-FIA (m/z): calcd for [M-PF₆⁻], 588.1418. Found, 588.1419. Crystal structure is shown in the X-ray Crystallographic Analysis section.

(N,N-dimethyl)naphthalene-1-yl]methanamino)(tetrapyrazolylborate) palladium(IV) fluoride triflate (5)

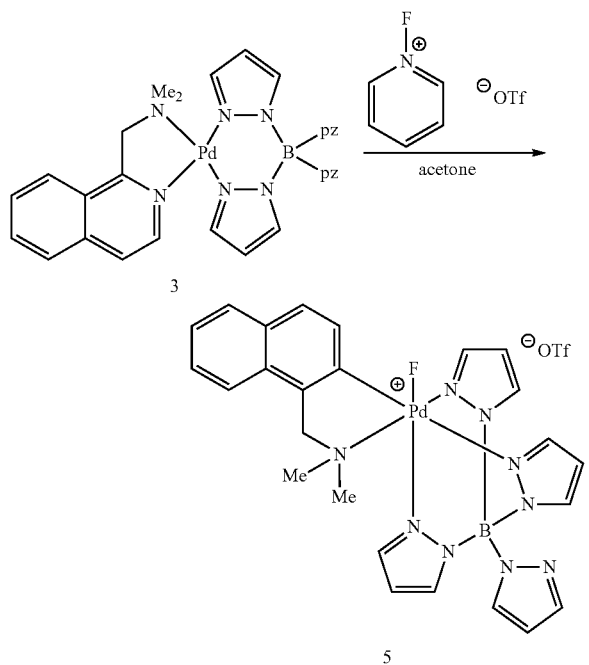

To (N,N-dimethyl[naphthalen-1-yl]methanamino)(tetrapyrazolylborate)palladium(II) (3) (5.7 mg, 0.010 mmol, 1.0 equiv) suspended in 0.5 mL acetone-d6 is added 1-fluoropyridinium triflate (2.5 mg, 0.010 mmol, 1.0 equiv) in one portion at 0° C. After stirring 20 minutes at 0° C., the reaction mixture is warmed to 23° C. and further stirred for 30 minutes.

NMR Spectroscopy: $^1$H NMR (500 MHz, acetone-d6, 23° C., δ): 8.79 (d, J=2.0 Hz, 1H), 8.64-8.58 (m, 2H), 8.50 (d, J=1.5 Hz, 1H), 8.47 (d, J=1.5 Hz, 1H), 8.45 (d, J=2.0 Hz, 1H), 8.12-8.07 (m, 3H), 8.00 (br s, 1H), 7.86-7.80 (m, 2H), 7.79 (d, J=2.0 Hz, 1H), 7.68 (ddd, J=7.5 Hz, 7.0 Hz, 2.0 Hz, 1H), 7.59 (dd, J=7.5 Hz, 7.0 Hz, 1H), 7.41 (dd, J=6.0 Hz, 4.5 Hz, 1H), 6.82 (dd, J=1.5 Hz, 1.5 Hz, 1H), 6.72 (dd, J=2.0 Hz, 2.0 Hz, 1H), 6.70 (dd, J=2.0 Hz, 2.0 Hz, 1H), 6.63 (d, J=2.0 Hz, 1H), 6.49 (dd, J=2.0 Hz, 2.0 Hz, 1H), 5.50 (d, J=12.5 Hz, 1H), 4.87 (d, $J_{H,H}$=12.5 Hz, $J_{H,F}$=4.5 Hz, 1H), 3.62 (s, 3H), 3.24 (s, 3H). $^{19}$F NMR (375 MHz, acetone-d6, 23° C., δ): −79.5 (s, 3F), −287.4 (s, 1F).

X-ray Crystallographic Analysis
Experimental

The compound was crystallized from a dichloromethane/benzene/hexape solution as orange-yellow plates. A crystal 0.050 mm×0.075 mm×0.100 mm in size was selected, mounted on a nylon loop with Paratone-N oil, and transferred to a Bruker SMART APEX II diffractometer equipped with an Oxford Cryosystems 700 Series Cryostream Cooler and Mo Kα radiation (λ=0.71073 Å). A total of 1855 frames were collected at 193 (2) K with an oscillation range of 0.5°/frame, and an exposure time of 30 s/frame using the APEX2 suite of software. (Bruker AXS, 2006a) Data were collected to $θ_{max}$=22.50° rather than the routine value of $θ_{max}$=27.50° because the crystal examined did not exhibit usable diffraction beyond 22.50°. Unit cell refinement on all observed reflections, and data reduction with corrections for Lp and decay were performed using SAINT. (Bruker AXS, 2006b) Scaling and a numerical absorption correction were done using SADABS. (Bruker AXS, 2004) The minimum and maximum transmission factors were 0.9237 and 0.9608, respectively. A total of 18585 reflections were collected, 4559 were unique ($R_{int}$=0.0763), and 3098 had I>2σ(I). The lack of systematic absences was consistent with the compound having crystallized in the triclinic space group P1 or P1̄. The centrosymmetric space group P1̄ (No. 2) was selected. The observed mean |E$^2$−1| value was 0.867 (versus the expectation values of 0.968 and 0.736 for centric and noncentric data, respectively).

The structure was solved by direct methods and refined by full-matrix least-squares on F$^2$ using SHELXTL. (Bruker AXS, 2001) The asymmetric unit was found to contain one (fluoro)[1-{(dimethyl-amino)-methyl}naphthalenyl](tetrapyrazoylborate)palladium(IV) cation, one hexafluorophosphate anion, a half-molecule of benzene, and one dichloromethane. All of the nonhydrogen atoms were refined with anisotropic displacement coefficients. The hydrogen atoms were assigned isotropic displacement coefficients U(H)=1.2 U(C) or 1.5 U ($C_{methyl}$), and their coordinates were allowed to ride on their respective carbons. The hexafluorophosphate anion was treated with a two-site disorder model [P(1), F(2), F(3), F(4), F(5), F(6), F(7)] and [P(1'), F(2'), F(3'), F(4'), F(5'), F(6), F(7')] with refined site occupany factors of 0.80 (2) and 0.20 (2), respectively, and included in the least-squares refinement with mild rigid-bond, similar $U_{ij}$, 1,2- and 1,3-distance restraints. The refinement converged to R(F)=0.0603, wR(F$^2$)=0.1534, and S=1.079 for 3098 reflections with I>2σ(I), and R(F)=0.1011, wR(F$^2$)=0.1783, and S=1.079 for 4559 unique reflections, 517 parameters, and 252 restraints. The maximum |Δ/σ| in the final cycle of least-squares was less than 0.001, and the residual peaks on the final difference-Fourier map ranged from −0.864 to 1.312 eÅ$^{-3}$. Scattering factors were taken from the International Tables for Crystallography, Volume C. (Maslen et al., 1992, and Creagh & McAuley, 1992)

REFERENCES

Bruker AXS (2001). *SHELXTL* v6.12. Bruker Analytical X-ray Systems Inc., Madison, Wis., USA.
Bruker AXS (2004). *SADABS*. Bruker Analytical X-ray Systems Inc., Madison, Wis., USA.
Bruker AXS (2006a). *APEX*2 v2.1-0. Bruker Analytical X-ray Systems Inc., Madison, Wis., USA.
Bruker AXS (2006b). *SAINT V*7.34A. Bruker Analytical X-ray Systems Inc., Madison, Wis., USA.
Creagh, D. C. & McAuley, W. J. (1992). *International Tables for Crystallography: Mathematical, Physical and Chemical Tables*, Vol C, edited by A. J. C. Wilson, pp. 206-222. Dordrecht, The Netherlands: Kluwer.
Maslen, E. N., Fox, A. G. & O'Keefe, M. A. (1992). *International Tables for Crystallography: Mathematical, Physical and Chemical Tables*, Vol C, edited by A. J. C. Wilson, pp. 476-516. Dordrecht, The Netherlands: Kluwer.

R(F)=R1=Σ||F$_o$|−|F$_c$||/Σ|F$_o$|, wR(F$^2$)=wR2=[Σw(F$_o^2$−F$_c^2$)$^2$/Σw(F$_o^2$)$^2$]$^{1/2}$, and S=Goodness-of-fit on F$^2$=[Σw(F$_o^2$−F$_c^2$)$^2$/(n−p)]$^{1/2}$, where n is the number of reflections and p is the number of parameters refined.

TABLE 2

Crystal data and structure refinement for 7

| | |
|---|---|
| Identification code | 7 = [PdF(C12H12BN8)(C13H14N)](PF6)•0.5(C6H6)•CH2Cl2 |
| Empirical formula | C29 H31 B Cl2 F7 N9 P Pd |
| Formula weight | 857.71 |
| Temperature | 193(2) K |
| Wavelength | 0.71073 Å |
| Crystal system | Triclinic |
| Spacegroup | P −1 |
| Unit cell dimensions | a = 11.7615(6) Å  α = 66.456(3)°. |
| | b = 11.9764(6) Å  β = 86.013(4)°. |
| | c = 13.5288(7) Å  γ = 89.291(4)°. |
| Volume | 1742.56(15) Å$^3$ |
| Z | 2 |
| Density (calculated) | 1.635 Mg/m$^3$ |
| Absorption coefficient | 0.806 mm$^{-1}$ |
| F(000) | 862 |
| Crystal size | 0.100 × 0.075 × 0.050 mm$^3$ |
| Theta range for data collection | 1.65 to 22.50°. |
| Index ranges | −12 <= h <= 11, −12 <= k <= 12, −14 <= l <= 14 |
| Reflections collected | 18585 |
| Independent reflections | 4559 [R(int) = 0.0763] |
| Completeness to theta = 22.50° | 100.0% |
| Absorption correction | Numerical |
| Max. and min. transmission | 0.9608 and 0.9237 |
| Refinement method | Full-matrix least-squares on F$^2$ |
| Data/restraints/parameters | 4559/252/517 |
| Goodness-of-fit on F$^2$ | 1.079 |
| Final R indices [I > 2sigma(I)] | R1 = 0.0603, wR2 = 0.1534 |
| R indices (all data) | R1 = 0.1011, wR2 = 0.1783 |
| Largest diff. peak and hole | 0.525 and −0.543 e.Å$^{-3}$ |

OTHER EMBODIMENTS

The foregoing has been a description of certain embodiments of the invention. Those of ordinary skill in the art will appreciate that various changes and modifications to this description may be made without departing from the spirit or scope of the present invention, as defined in the following claims.

The invention claimed is:

1. A palladium complex of formula (I):

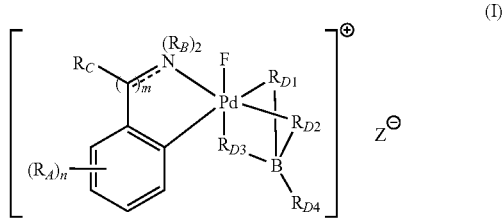

(I)

wherein:
the dashed line represents the presence or absence of a bond;
Pd has a valency of +4;
n is an integer between 0 and 4, inclusive;
m is an integer between 0 and 3, inclusive;
each occurrence of $R_A$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to form a substituted or unsubstituted carbocyclic, heterocyclic, aryl or heteroaryl ring;

each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;

each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring;

$R_{D1}$, $R_{D2}$, $R_{D3}$, and $R_{D4}$ are each a substituted or unsubstituted pyrazolyl ring;

Z$^-$ is an anion such as halide, acetate, tosylate, azide, tetrafluoroborate, tetraphenylborate, tetrakis(pentafluorophenyl)borate, [B[3,5-(CF$_3$)$_2$C$_6$H$_3$]$_4$]$^-$, hexafluorophosphate, phosphate, sulfate, perchlorate, trifluoromethanesulfonate or hexafluoroantimonate; and F comprises $^{18}$F or $^{19}$F.

2. The palladium complex of claim 1, wherein $R_C$ is hydrogen.

3. The palladium complex of claim 1, wherein n is 2.

4. The palladium complex of claim 1, wherein two $R_A$ are taken together to form an aryl ring.

5. The palladium complex of claim 4, wherein two $R_A$ are taken together to form a phenyl ring.

6. The palladium complex of claim 1, wherein m is 1.

7. The palladium complex of claim 1, wherein at least one $R_B$ is $C_1$-$C_6$ alkyl.

8. The palladium complex of claim 1, wherein both $R_B$ are methyl.

9. The palladium complex of claim 1, wherein the dashed line represents the absence of a bond.

10. The palladium complex of claim 1, wherein $R_{D1}$, $R_{D2}$, $R_{D3}$ and $R_{D4}$ are each an unsubstituted pyrazolyl ring.

11. The palladium complex of claim 1, wherein the anion is trifluoromethanesulfonate.

12. The palladium complex of claim 1, wherein the anion is hexafluorophosphate.

13. The palladium complex of claim 1, wherein the anion is a halide.

14. The palladium complex of claim 1, wherein the complex has the following formula:

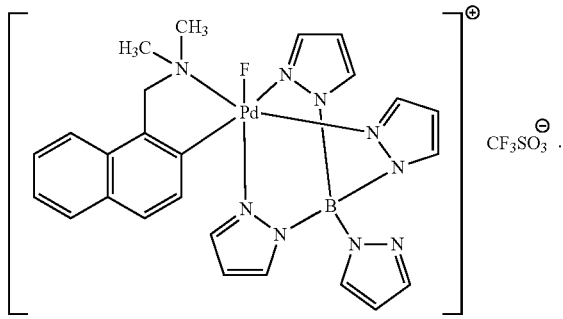

15. The palladium complex of claim 1, wherein the complex has the following formula:

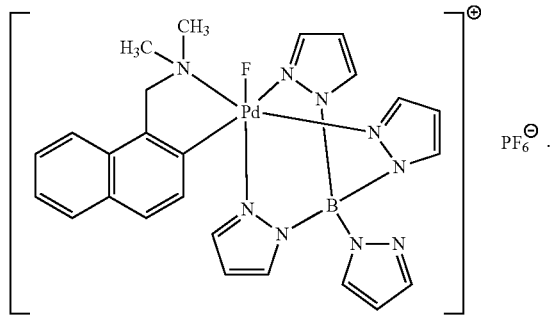

16. A method of fluorinating an organic compound, the method comprising mixing a palladium complex of formula (I) of claim 1 with a substrate under conditions sufficient to fluorinate the substrate, thereby providing a fluorinated organic compound.

17. The method of claim 16, wherein the fluorinated organic compound comprises $^{18}$F or $^{19}$F.

18. The method of claim 16, wherein the substrate is an organic compound comprising an enol silyl ether, and the fluorinated organic compound is an α-fluorinated ketone.

19. The method of claim 16, wherein the substrate is a palladium(II) aryl complex, and the fluorinated organic compound is a fluorinated aryl compound.

20. The method of claim 16, wherein the substrate is an arylsilver complex, and the fluorinated organic compound is a fluorinated aryl compound.

21. The method of claim 16, wherein the fluorinated organic compound comprises an aryl group.

22. The method of claim 16, wherein the fluorinated organic compound is a pharmaceutically acceptable compound or a prodrug thereof.

23. A composition comprising a palladium complex of formula (I) of claim 1 and an additional component.

24. A kit comprising a palladium complex of formula (I) of claim 1 and a container.

25. A method of making a fluorinated Pd(IV) complex of claim 1, the method comprising reacting a palladium complex of formula (II)

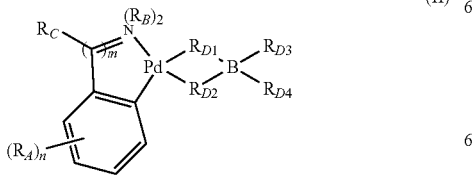

(II)

wherein
the dashed line represents the presence or absence of a bond;
Pd has a valency of +2;
n is an integer between 0 and 4, inclusive;
m is an integer between 0 and 3, inclusive;
each occurrence of $R_A$ independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR'; —C(=O)R'; —CO$_2$R'; —CN; —SCN; —SR'; —SOR'; —SO$_2$R'; —NO$_2$; —N(R')$_2$; —NHC(O)R'; or —C(R')$_3$; wherein each occurrence of R' is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety; wherein two $R_A$ may be taken together to form a substituted or unsubstituted carbocyclic, heterocyclic, aryl or heteroaryl ring;
each occurrence of $R_B$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; —OR"; —C(=O)R"; —CO$_2$R"; —CN; —SCN; —SR"; —SOR"; —SO$_2$R"; —NO$_2$; —N(R")$_2$; —NHC(O)R"; or —C(R")$_3$; wherein each occurrence of R" is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety;
each occurrence of $R_C$ is independently hydrogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted aryl; substituted or unsubstituted heteroaryl; wherein $R_C$ and $R_B$ may be taken together to form a substituted or unsubstituted heterocyclic or heteroaryl ring; and wherein $R_C$ and $R_A$ may be taken together to form a substituted or unsubstituted carbocyclic, heterocyclic, aryl or heteroaryl ring; and
$R_{D1}$, $R_{D2}$, $R_{D3}$ and $R_{D4}$ are each a substituted or unsubstituted pyrazolyl ring; with a fluorinating agent, to provide the fluorinated Pd(IV) complex of claim 1.

26. The method of claim 25, wherein the fluorinating agent comprises $^{18}$F or $^{19}$F.

27. A method of preparing a palladium fluoride complex of formula:

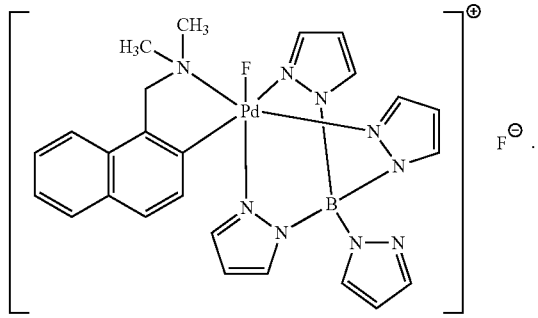

the method comprising steps of:
reacting a palladium chloride complex of formula:
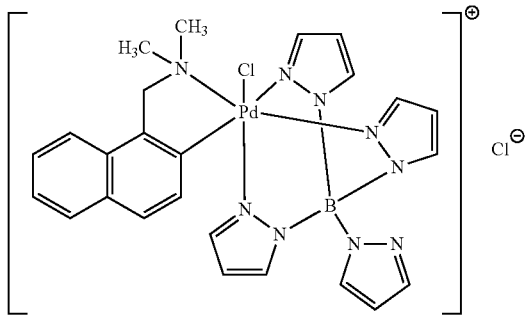
with nucleophilic F⁻ under suitable conditions to yield a complex of formula:
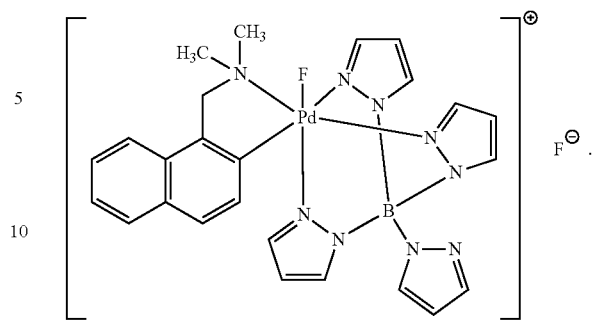
28. The method of claim 27, wherein the nucleophilic F⁻ is provided by AgF.
29. The method of claim 27, wherein the nucleophilic F is $^{18}$F⁻.
* * * * *